US007361658B2

(12) United States Patent
Sugasawa et al.

(10) Patent No.: US 7,361,658 B2
(45) Date of Patent: Apr. 22, 2008

(54) 2-ACYLAMINOTHIAZOLE DERIVATIVE OR SALT THEREOF

(75) Inventors: Keizo Sugasawa, Tokyo (JP); Yuji Koga, Tokyo (JP); Kazuyoshi Obitsu, Tokyo (JP); Takao Okuda, Tokyo (JP); Koichiro Harada, Tokyo (JP); Hideki Kubota, Tokyo (JP); Fukushi Hirayama, Tokyo (JP); Masaki Abe, Tokyo (JP); Ken-ichi Suzuki, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 64 days.

(21) Appl. No.: 10/564,520

(22) PCT Filed: Jul. 15, 2004

(86) PCT No.: PCT/JP2004/010440

§ 371 (c)(1),
(2), (4) Date: Jan. 13, 2006

(87) PCT Pub. No.: WO2005/007651

PCT Pub. Date: Jan. 27, 2005

(65) Prior Publication Data

US 2006/0194844 A1 Aug. 31, 2006

(30) Foreign Application Priority Data

Jul. 17, 2003 (JP) ............................ 2003-275718

(51) Int. Cl.

| | |
|---|---|
| *A61K 31/4427* | (2006.01) |
| *A61K 31/4523* | (2006.01) |
| *A61K 31/496* | (2006.01) |
| *C07D 403/12* | (2006.01) |
| *C07D 401/12* | (2006.01) |
| *C07D 211/26* | (2006.01) |
| *C07D 401/14* | (2006.01) |

(52) U.S. Cl. ................. 514/252.13; 514/326; 514/336; 514/318; 544/359; 546/209; 546/193; 546/207; 546/268.1

(58) Field of Classification Search ................ 548/195; 544/359; 546/209, 193, 207, 268.1; 514/252.13, 514/326, 336, 318
See application file for complete search history.

(56) References Cited

U.S. PATENT DOCUMENTS

| | | | | |
|---|---|---|---|---|
| 5,256,675 | A | 10/1993 | Matsuo et al. | |
| 5,369,107 | A | 11/1994 | Matsuo et al. | |
| 5,380,736 | A * | 1/1995 | Boigegrain et al. | 544/369 |
| 2003/0195231 | A1 | 10/2003 | Hiroshi et al. | |
| 2004/0077697 | A1 | 4/2004 | Koshio et al. | |
| 2005/0153977 | A1 | 7/2005 | Sugasawa et al. | |

FOREIGN PATENT DOCUMENTS

| | | | |
|---|---|---|---|
| EP | 1 207 155 | A1 | 5/2002 |
| JP | 3-68567 | | 3/1991 |
| WO | WO 01/07423 | A1 | 2/2001 |
| WO | WO 01/53267 | A1 | 7/2001 |
| WO | WO 02/062775 | A1 | 8/2002 |
| WO | WO 03/062233 | A1 | 7/2003 |

OTHER PUBLICATIONS

International Search Report.

* cited by examiner

*Primary Examiner*—Rebecca L Anderson
*Assistant Examiner*—Michael P Barker
(74) *Attorney, Agent, or Firm*—Finnegan, Henderson, Farabow, Garrett & Dunner, L.L.P.

(57) ABSTRACT

2-Acylaminothiazole derivatives or salts thereof which have a platelet increasing activity based on an excellent human c-mpl-Ba/F3 cell growth function and a function of accelerating formation of megakaryocytic colonies and which are useful for treating thrombocytopenia are provided.

32 Claims, No Drawings

2-ACYLAMINOTHIAZOLE DERIVATIVE OR SALT THEREOF

TECHNICAL FIELD

The present invention relates to novel 2-acylaminothiazole derivatives or salts thereof which are useful as medicaments, especially a thrombocytopenia treating agent, and medicaments comprising one or more said compounds as active ingredients.

BACKGROUND ART

Platelets are non-nucleated blood cells which play a main role in physiological hemostasis and pathologic thrombus generation. Platelets are constantly produced in vivo from megakaryocytes, precursor cells. Platelets are, like other blood cells, produced from multipotential stem cells. Multipotential stem cells become megakaryocytic precursor cells, from which megakaryoblasts, promegakaryoblasts and megakaryocytes are formed in this order. During maturation of the megakaryocytes, immature megakaryocytes conduct DNA synthesis only without cell division to form polyploids. Thereafter, maturation of cytoplasms begins to form platelet separation membranes, and the cytoplasms are split to release platelets.

Meanwhile, a decrease in platelets due to various hematopoietic disorders in chemotherapy, radiotherapy or the like of anemia, myelodysplastic syndrome or malignant tumor induces serious conditions such as invitation of bleeding tendency. Therefore, various attempts of technical development for increasing platelets have been made for the purpose of treating the same. At present, a potent method for treating thrombocytopenia is platelet transfusion. However, a sufficient amount of platelets is not yet supplied, and life of platelets transfused is short. For these reasons, it is hard to satisfactorily improve thrombocytopenia. Moreover, platelet transfusion involves problems such as viral infection, production of alloantibody and graft versus host disease (GVHD). Accordingly, the development of medications for relaxing an inhibitory state of a hematopoietic function induced by various diseases or therapies and accelerating recovery of the number of platelets has been expected.

Under these circumstances, it has been reported that thrombopoietin (hereinafter referred to as TPO) which is a main factor participating in division to megakaryocytic cells and is a c-Mpl ligand is cloned to stimulate division and growth of megakaryocytic cells and accelerate production of platelets (Kaushansky K. et al., Nature, 369, 568-571, 1994; Non-patent Document 1). TPO has already been subjected to a clinical test as a platelet increasing agent, and usefulness and tolerance in humans are being confirmed. However, in a clinical test of PEG-rHuMGDF (TPO whose 163rd amino acid seen from the N-terminal has been modified with polyethylene glycol) which is a type of TPO, a neutralizing antibody has been confirmed (Li J. et. al., Blood, 98, 3241-3248, 2001: Non-patent Document 2, and Basser R. L. et al., Blood, 99, 2599-2602, 2002: Non-patent Document 3). Accordingly, there is a fear of TPO immunogenicity. Further, since TPO is a protein, it is decomposed in digestive organs, and is thus not practical as an oral administration drug. For the same reason, a low-molecular peptide is not considered either to be practical as an oral administration drug. Under these circumstances, the development of an orally administrable non-peptide c-Mpl ligand with less immunogenicity has been under way for treatment of thrombocytopenia.

As the foregoing compounds, benzodiazepine derivatives (Patent Document 1), acylhydrazone derivatives (Patent Document 2), diazonaphthalene derivatives (Patent Document 3), pyrrocarbazole derivatives (Patent Document 4), pyrrophenanthridine derivatives (Patent Document 5) and pyrrophthalimide derivatives (Patent Document 6) have been known.

WO 01/07423 (Patent Document 7) describes that compounds represented by the following general formula (VII) have a platelet increasing function.

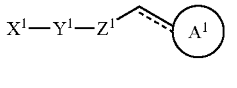

(VII)

(As to symbols in the formula, refer to the document.)

The document describes the compounds containing thiazole which may be substituted as $X^1$ and —NHCO— as $Y^1$. In the present invention, however, $R^3$ in the compounds of the invention is not substituted with a substituent having an $A^1$ group such as a thiazolyl group in the document. Moreover, regarding compounds in which the 5-position of thiazole is substituted with a lower alkyl substituted with a nitrogen atom, there is not any concrete disclosure by Examples or the like in the document.

WO 01/53267 (Patent Document 8) describes that compounds represented by the following general formula (VIII) have a platelet increasing function.

$$X^1—Y^1\text{-}Z^1\text{-}W^1 \qquad \text{(VIII)}$$

(As to symbols in the formula, refer to the document.)

The document describes the compounds containing thiazole which may be substituted as $X^1$ and —NHCO— as $Y^1$. In the present invention, however, $R^3$ in the compounds of the present invention is not substituted with a substituent having a $W^1$ group in the document. Regarding compounds in which the 5-position of thiazole is substituted with a lower alkyl substituted with a nitrogen atom, there is not any concrete disclosure by Examples or the like in the document.

WO 02/62775 (Patent Document 9) describes that compounds represented by the following general formula (IX) have a platelet increasing function.

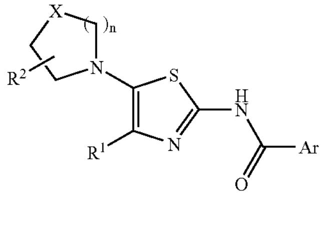

(IX)

(As to symbols in the formula, refer to the document.)

The document describes the compounds in which the 5-position of 2-acylaminothiazole is directly substituted with a nitrogen atom. However, it does not describe compounds in which the 5-position of thiazole is substituted with a lower alkyl substituted with a nitrogen atom in the present invention.

WO 03/062233 (Patent Document 10) describes that compounds represented by the following general formula (X) have a platelet increasing function.

(X)

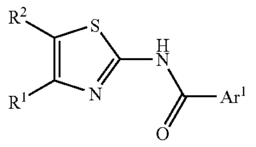

(As to symbols in the formula, refer to the document.)

The document describes the compounds in which the 5-position of 2-acylaminothiazole is directly substituted with a nitrogen atom. However, it does not describe compounds in which the 5-position of thiazole is substituted with a lower alkyl substituted with a nitrogen atom in the present invention.

In addition to the foregoing Patent Documents 7 to 10, 2-acylaminothiazole compounds are described as cholecystokinin and gastrin receptor antagonists in U.S. Pat. No. 3,199,451 (Patent Document 11) or as compounds having antiinflammatory characteristics in Chemical and Pharmaceutical Bulletin, 25, 9, 2292-2299, 1977 (Non-patent Document 4). However, none of them indicate at all the platelet increasing function in the present invention.

Under such circumstances, the development of an orally administrable non-peptide c-Mpl ligand with less antigenicity has been in demand for treatment of thrombocytopenia.

| | |
|---|---|
| [Patent Document 1] | JP-A-11-152276 |
| [Patent Document 2] | WO 99/11262 pamphlet |
| [Patent Document 3] | WO 00/35446 pamphlet |
| [Patent Document 4] | WO 98/09967 pamphlet |
| [Patent Document 5] | JP-A-10-212289 |
| [Patent Document 6] | JP-A-2000-44562 |
| [Patent Document 7] | WO 01/07423 pamphlet |
| [Patent Document 8] | WO 01/53267 |
| [Patent Document 9] | WO 02/62775 pamphlet |
| [Patent Document 10] | WO 03/062233 pamphlet |
| [Patent Document 11] | Patent No. 3199451 |
| [Non-Patent Document 1] | Nature, 1994, No. 369, p. 568-571 |
| [Non-Patent Document 2] | Blood, 2001, vol. 98, p. 3241-3248 |
| [Non-Patent Document 3] | Blood, 2002, vol. 99, p. 2599-2602 |
| [Non-Patent Document 4] | Chemical and Pharmaceutical Bulletin, 1977, vol. 25, No. 9, p. 2292-2299 |

[Non-patent Document 1] Nature, 1994, No. 369, p. 568-571

[Non-patent Document 2] Blood, 2001, vol. 98, p. 3241-3248

[Non-patent Document 3] Blood, 2002, vol. 99, p. 2599-2602

[Non-patent Document 4] Chemical and Pharmaceutical Bulletin, 1977, vol. 25, No. 9, p. 2292-2299

DISCLOSURE OF THE INVENTION

The present inventors have assiduously conducted investigations on compounds having a platelet increasing function, and have found that novel 2-acylaminothiazole derivatives have an excellent platelet increasing function. They have thus completed the present invention.

That is, according to the present invention, the following (1) to (15) are provided.

(1) A platelet increasing agent comprising a 2-acylaminothiazole derivative represented by the formula (I) or a pharmaceutically acceptable salt thereof as an active ingredient.

(I)

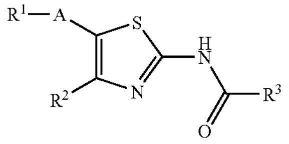

[Symbols in the formula have the following meanings.

A: a lower alkylene $R^1$: a group represented by the formula (II), or cyclic amino which may be substituted.

(II)

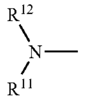

[Symbols in the formula have the following meanings.

$R^{11}$: H, a lower alkyl which may be substituted, or a cycloalkyl which may be substituted. When A represents methylene, $R^{11}$ may be present as methylene which is bridged to thienyl or phenyl represented by $R^2$. When A represents methylene, $R^{11}$ may be present as a lower alkylene which may be substituted and which forms a ring closed at the methylene represented by A.

$R^{12}$: a lower alkyl, a cycloalkyl or a non-aromatic heterocycle, each of which may be substituted.]

$R^2$: thienyl or phenyl, each of which may be substituted.

$R^3$: an aromatic heterocycle, an aryl or cyclic amino, each of which may be substituted.]

(2) The pharmaceutical composition of (1), wherein A is methylene.

(3) The pharmaceutical composition of (2), wherein $R^2$ is thienyl or phenyl, each of which is substituted with one or more groups selected from the group consisting of a lower alkyl which may be substituted with one or more halogens, and a halogen.

(4) The pharmaceutical composition of any of (1) to (3), which is a thrombocytopenia treating agent.

(5) The pharmaceutical composition of any of (1) to (3), which is a c-Mpl ligand.

(6) A 2-acylaminothiazole derivative represented by the formula (III) or a pharmaceutically acceptable salt thereof.

(III)

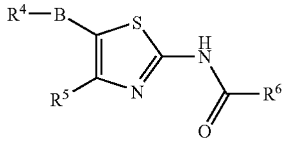

[Symbols in the formula have the following meanings.

B: a group represented by A according to (1).

$R^4$: a group represented by $R^1$ according to (1).

$R^5$: a group represented by $R^2$ according to (1).

$R^6$: a group represented by $R^3$ according to (1), provided that unsubstituted phenyl and indole which may be substituted are excluded.]

(7) The compound of (6), wherein B is methylene.

(8) The compound of (7), wherein $R^5$ is thienyl or phenyl, each of which is substituted with one or more groups selected from the group consisting of a lower alkyl which may be substituted with one or more halogens, and a halogen.

(9) The compound of (8), wherein $R^6$ is pyridyl which may be substituted, or phenyl which is substituted.

(10) The compounds of (8), wherein $R^6$ is pyridin-3-yl whose 5-position is substituted with a group selected from the group consisting of chloro and fluoro, and whose 6-position is substituted, or phenyl whose 3-position is substituted with a group selected from the group consisting of chloro and fluoro, whose 5-position is substituted with a group selected from the group consisting of —H, chloro and fluoro, and whose 4-position is substituted.

(11) Compounds selected from the group consisting of compound group X and compound group Y, preferably compound group X, among the compounds of (6).

Here, "compound group X" is a compound group consisting of

1-{3-chloro-5-[(4-(4-chlorothiophen-2-yl)-5-{[cyclobutyl(methyl)amino]methyl}thiazol-2-yl)carbamoyl]-2-pyridyl}piperidine-4-carboxylic acid, 1-(5-{[5-{[butyl(methyl)amino]methyl}-4-(4-chlorothiophen-2-yl)thiazol-2-yl]carbamoyl}-3-chloro-2-pyridyl)piperidin-4-carboxylic acid, 1-{5-[(4-(4-chlorothiophen-2-yl)-5-{[(2R)-2-methylpyrrolidin-1-yl]methyl}thiazol-2-yl)carbamoyl]-3-fluoro-2-pyridyl}piperidin-4-carboxylic acid, 1-{3-chloro-5-[(4-(4-chlorothiophen-2-yl)-5-{[(2S)-2-methylpyrrolidin-1-yl]methyl}thiazol-2-yl)carbamoyl]-2-pyridyl}piperidine-4-carboxylic acid, 1-(3-chloro-5-{[4-(4-chlorothiophen-2-yl)-5-(dimethylaminomethyl)thiazol-2-yl]carbamoyl}-2-pyridyl)piperidine-4-carboxylic acid, 1-{3-chloro-5-[(4-(4-chlorothiophen-2-yl)-5-{[isopropyl(methyl)amino]methyl}thiazol-2-yl)carbamoyl]-2-pyridyl}piperidine-4-carboxylic acid, 4-[{3-chloro-5-[(4-(4-chlorothiophen-2-yl)-5-{[isopropyl(methyl)amino]methyl}thiazol-2-yl)carbamoyl]-2-pyridyl}(methyl)amino]butyric acid, 1-{3-chloro-5-[(4-(4-chlorothiophen-2-yl)-5-{[(3S)-3-methylpyrrolidin-1-yl]methyl}thiazol-2-yl)carbamoyl]-2-pyridyl}piperidine-4-carboxylic acid, 1-{3-chloro-5-[(4-(4-chlorothiophen-2-yl)-5-{[[(2S)-2-methoxypropyl](methyl)amino]methyl}thiazol-2-yl)carbamoyl]-2-pyridyl}piperidine-4-carboxylic acid, N-[5-{[butyl(methyl)amino]methyl}-4-(4-chlorothiophen-2-yl)thiazol-2-yl]-5-chloro-6-[(3-hydroxypropyl)amino]nicotinamide, N-[5-{[butyl(methyl)amino]methyl}-4-(4-chlorothiophen-2-yl)thiazol-2-yl]-5-chloro-6-(3-oxopiperazin-1-yl)nicotinamide and N-[5-{[butyl(methyl)amino]methyl}-4-(4-chlorothiophen-2-yl)thiazol-2-yl]-5-chloro-6-[4-(hydroxymethyl)piperidino]nicotinamide, and pharmaceutically acceptable salts thereof, and "compound group Y" is a compound group consisting of 1-{3-chloro-5-[(4-(4-chlorothiophen-2-yl)-5-{[(2R)-2-methylpyrrolidin-1-yl]methyl}thiazol-2-yl)carbamoyl]-2-pyridyl}piperidine-4-carboxylic acid, 4-[{3-chloro-5-[(4-(4-chlorothiophen-2-yl)-5-{[(2R)-2-methylpyrrolidin-1-yl]methyl}thiazol-2-yl)carbamoyl]-2-pyridyl}(methyl)amino]butyric acid, 4-[{3-chloro-5-[(4-(4-chlorothiophen-2-yl)-5-{[(2S)-2-methylpyrrolidin-1-yl]methyl}thiazol-2-yl)carbamoyl]-2-pyridyl}(methyl)amino]butyric acid, 1-{5-[(4-(4-chlorothiophen-2-yl)-5-{[(2S)-2-methylpyrrolidin-1-yl]methyl}thiazol-2-yl)carbamoyl]-3-fluoro-2-pyridyl}piperidine-4-carboxylic acid, (1-{3-chloro-5-[(4-(4-chlorothiophen-2-yl)-5-{[(2R)-2-methylpyrrolidin-1-yl]methyl}thiazol-2-yl)carbamoyl]-2-pyridyl}azetidin-3-yl)acetic acid, (1-{3-chloro-5-[(4-(4-chlorothiophen-2-yl)-5-{[(2S)-2-methylpyrrolidin-1-yl]methyl}thiazol-2-yl)carbamoyl]-2-pyridyl}azetidin-3-yl)acetic acid, 1-(3-chloro-5-{[5-{[isopropyl(methyl)amino]methyl}-4-(4-methylthiophen-2-yl)thiazol-2-yl]carbamoyl}-2-pyridyl)piperidine-4-carboxylic acid, 1-{3-chloro-5-[(4-(4-chlorothiophen-2-yl)-5-{[(3R)-3-methylpyrrrolidin-1-yl]methyl}thiazol-2-yl)carbamoyl]-2-pyridyl}piperidine-4-carboxylic acid, 1-{3-chloro-5-[(4-(4-chlorothiophen-2-yl)-5-{[[(2R)-2-methoxypropyl](methyl)amino]methyl}thiazol-2-yl)carbamoyl]-2-pyridyl}piperidine-4-carboxylic acid, 1-(5-{[5-(azepan-1-ylmethyl)-4-(4-chlorothiophen-2-yl)thiazol-2-yl]carbamoyl}-3-chloro-2-pyridyl)piperidine-4-carboxylic acid, 1-{3-chloro-5-[(4-(4-chlorothiophen-2-yl)-5-{[(2-methoxyethyl)(methyl)amino]methyl}thiazol-2-yl)carbamoyl]-2-pyridyl}piperidine-4-carboxylic acid, 1-(5-{[5-azocan-1-ylmethyl)-4-(4-chlorothiophen-2-yl)thiazole-2-yl]carbamoyl}-3-chloro-2-pyridyl)piperidine-4-carboxylic acid, 1-{3-chloro-5-[(4-(4-chlorothiophen-2-yl)-5-{[cyclohexyl(methyl)amino]methyl}thiazol-2-yl)carbamoyl]-2-pyridyl}piperidine-4-carboxylic acid and 1-{3-chloro-5-[(4-(4-chlorothiophen-2-yl)-5-{[cyclopropyl(methyl)amino]methyl}thiazol-2-yl)carbamoyl]-2-pyridyl}piperidine-4-carboxylic acid, and pharmaceutically acceptable salts thereof.

(12) A pharmaceutical composition comprising the compound according to any of (6) to (10) as an active ingredient.

(13) The pharmaceutical composition according to (11), which is a platelet increasing agent.

(14) The pharmaceutical composition according to (11), which is a thrombocytopenia treating agent.

(15) The pharmaceutical composition according to (11), which is a c-Mpl ligand.

A in the compounds represented by formula (I) and B in the compounds represented by formula (III) are preferably methylene.

$R^1$ in the compounds represented by formula (I) and $R^4$ in the compounds represented by formula (III) are preferably a group represented by formula (II) in which $R^{11}$ is lower alkyl and $R^{12}$ is lower alkyl or cycloalkyl which may be substituted respectively, or cyclic amino which may be substituted with lower alkyl; more preferably a group represented by formula (II) in which $R^{11}$ is methyl and $R^{12}$ is lower alkyl or cycloalkyl which may be substituted respectively, or cyclic amino which may be substituted with methyl.

$R^2$ in the compounds represented by formula (I) and $R^5$ in the compounds represented by formula (III) are preferably thienyl which may be substituted; more preferably thienyl substituted with one or more substituents selected from the group consisting of lower alkyl which may be substituted with one or more halogens, and halogen; further preferably thienyl substituted with one or more groups selected from the group consisting of chloro and methyl; especially preferably 4-chlorothiophen-2-yl or 4-methylthiophen-2-yl. In another embodiment, $R^2$ in the compounds represented by formula (I) and $R^5$ in the compounds represented by formula (III) can be preferably phenyl which may be substituted; more preferably phenyl substituted with one or more groups selected from the group consisting of lower alkyl which may be substituted with one or more halogens, and halogen; further preferably phenyl substituted with one or more groups selected from the group consisting of trifluoromethyl, chloro and fluoro; especially preferably 3-trifluoromethylphenyl, 4-fluorophenyl or 3-chlorophenyl.

$R^3$ in the compounds represented by formula (I) and $R^6$ in the compounds represented by formula (III) are preferably pyridyl which may be substituted; more preferably pyridyl substituted with at least one halogen; more preferably pyridin-3-yl whose 5-position is substituted with a group selected from the member consisting of chloro and fluoro and whose 6-position is substituted. Of these, preferable is pyridin-3-yl whose 6-position is substituted with a group selected from the group consisting of piperidin-1-yl or piperazin-1-yl, each of which may be substituted with one or more groups selected from the group consisting of lower alkyl substituted with substituent group W, substituent group W and oxo, —O-lower alkyl, —NH-lower alkyl or —N(lower alkyl)-lower alkyl which may be substituted with one or more groups selected from substituent group W respectively, and whose 5-position is substituted with a group selected from the member consisting of chloro and fluoro.

Here, "substituent group W" indicates a group consisting of —OH, —O—$R^Z$, —OCO—$R^Z$, carboxyl, —$CO_2$—$R^Z$, —CO—$R^Z$ and carbamoyl which may be substituted with one or two $R^Z$s (when carbamoyl is substituted with two $R^Z$s, they may be the same or different), cyano, amino which may be substituted with one or two $R^Z$s (when amino is substituted with two $R^Z$s, they may be the same or different), —NHCO—$R^Z$, —$NHSO_2$—$R^Z$, sulfamoyl which may be substituted with one or two $R^Z$s (when sulfamoyl is substituted with two $R^Z$s, they may be the same or different), —$SO_3H$, —$P(O)(OH)_2$, —P(O)(OH)(O$R^Z$), —$P(O)(OR^Z)_2$, aromatic heterocycle, non-aromatic heterocycle and $R^Z$. "$R^Z$" represents lower alkyl, cycloalkyl or non-aromatic heterocycle, each of which may be substituted with one or more groups selected from the group consisting of —OH, —O-lower alkyl (this lower alkyl may be substituted with one or more groups selected from the member consisting of —OH, —O-lower alkyl and amino), —OCO-lower alkyl, carboxyl, —$CO_2$-lower alkyl, —CO-lower alkyl, carbamoyl which may be substituted with one or two lower alkyls (when carbamoyl is substituted with two lower alkyls, they may be the same or different), cyano, amino which may be substituted with one or two lower alkyls (when amino is substituted with two lower alkyls, they may be the same or different), —NHCO-lower alkyl, —$NHSO_2$-lower alkyl, sulfamoyl which may be substituted with one or two lower alkyls (when sulfamoyl is substituted with two lower alkyls, they may be the same or different), —$SO_3H$, —$P(O)(OH)_2$, —P(O)(OH)(O-lower alkyl), —$P(O)(O\text{-lower alkyl})_2$, aromatic heterocycle, non-aromatic heterocycle and halogen (this applies to the following).

In another embodiment, $R^3$ in the compounds represented by formula (I) and $R^6$ in the compounds represented by formula (III) can be preferably phenyl which may be substituted; more preferably phenyl substituted with at least one halogen; further preferably phenyl whose 3-position is substituted with a group selected from the member consisting of chloro and fluoro, whose 5-position is substituted with a group selected from the member consisting of —H, chloro and fluoro and whose 4-position is substituted. Of these, preferable is phenyl whose 4-position is substituted with a group selected from the group consisting of piperidin-1-yl or piperazin-1-yl, each of which may be substituted with one or more groups selected from the member consisting of lower alkyl substituted with substituent group W, substituent group W and oxo, —O-lower alkyl, —NH-lower alkyl or —N(lower alkyl)-lower alkyl which may be substituted with one or more groups selected from substituent group W respectively, and whose 3-position is substituted with a group selected from the member consisting of chloro and fluoro, and whose 5-position is substituted with a group selected from the member consisting of —H, chloro and fluoro.

In $R^{11}$, "when A represents methylene, $R^{11}$ may be present as methylene which is bridged to thienyl or phenyl represented by $R^2$" specifically means, for example, a partial structure of compounds shown in Table 30.

In $R^{11}$, "when A represents methylene, $R^{11}$ may be present as a lower alkylene which may be substituted and which forms a ring closed at the methylene represented by A" specifically means, for example, a partial structure of compounds shown in Table 33.

The compounds of the present invention are 2-acylaminothiazole derivatives whose 2-position is substituted with an acylamino group and whose 5-position is substituted with lower alkyl substituted with a nitrogen atom, in which point the characteristic feature of a chemical structure lies. The compounds of the present invention exhibit a human c-mpl-Ba/F3 cell growth activity, an activity of accelerating division of human $CD34^+$ cells to megakaryocytes and a good oral activity in a mouse oral administration test. Consequently, the compounds have a pharmacological property in that they exhibit a platelet increasing function.

The compounds of the present invention are further described below.

In the present specification, the word "lower" means a linear or branched carbon chain having from 1 to 6 carbon atoms unless otherwise instructed.

Accordingly, "lower alkyl" indicates $C_{1-6}$ alkyl. Specific examples thereof include methyl, ethyl, propyl, isopropyl, butyl, isobutyl, sec-butyl, tert-butyl, pentyl, neopentyl, hexyl and the like. Methyl, ethyl, propyl and isopropyl, which are $C_{1-3}$ alkyl, are preferable.

"Lower alkylene" is a divalent group of $C_{1-6}$ alkyl. Methylene, ethylene, trimethylene, methylethylene, tetramethylene, dimethylmethylene and dimethylethylene, which are $C_{1-4}$ alkylene, are preferable. Methylene and ethylene are more preferable, and methylene is especially preferable.

"Cycloalkyl" means a $C_{3-8}$ carbon ring, and it may partially have one or more unsaturated bonds. Accordingly, specific examples thereof can include cyclopropyl, cyclobutyl, cyclopentyl, cyclohexyl, cyclooctyl, cyclobutenyl, cyclohexenyl, cyclooctadienyl and the like.

"Aryl" means a $C_{6-14}$ monocyclic to tricyclic aromatic ring. Phenyl and naphthyl are preferable, and phenyl is more preferable.

"Cyclic amino" means a monovalent group of a 3- to 8-membered non-aromatic cyclic amine which has at least one nitrogen atom and may have further one or more hetero atoms selected from the member consisting of nitrogen, oxygen and sulfur, provided when plural hetero atoms are provided, they may be the same or different and at least one nitrogen atom has a bonding site. Specific examples thereof can include monovalent groups of azetidine, pyrrolidine, piperidine, azepane, azocane, azonane, azecane, piperazine, homopiperazine, morpholine and thiomorpholine, and the like.

"Non-aromatic heterocycle" means a monovalent group of a non-aromatic heterocycle having one or more hetero atoms selected from the member consisting of nitrogen, oxygen and sulfur, provided when plural hetero atoms are provided, they may be the same or different. Specific examples thereof can include monovalent groups of tetrahydrofuran, tetrahydropyran, tetrahydrothiofuran, tetrahydrothiopyran, oxetane, azetidine, pyrrolidine, piperidine, azepane, piperazine, homopiperazine, morpholine and thiomorpholine, and the like.

"Aromatic heterocycle" means a monovalent group of a 5- or 6-membered aromatic heterocycle having one or more hetero atoms selected from the member consisting of nitrogen, oxygen and sulfur, provided plural hetero atoms are provided, they may be the same or different, or the heterocycle which is partially hydrogenated. Specific examples thereof can include monovalent groups of pyridine, pyrazine, pyrimidine, pyridazine, pyrrole, imidazole, oxazole, thiazole, thiophene and furan. These heterocycles may be condensed with a benzene ring.

Examples of "halogen" include fluoro, chloro, bromo and iodo, and fluoro and chloro are preferable.

In the present specification, with respect to permissible substituents of the terms "which may be substituted" and "substituted", any substituents are available so long as they are ordinarily used as substituents of the respective groups. One or more of these substituents may be present in the respective groups.

Regarding permissible substituents in "cyclic amino which may be substituted" in $R^1$ and $R^4$, "cycloalkyl which may be substituted" in $R^{11}$, "cycloalkyl or non-aromatic heterocycle which may be substituted respectively" in $R^{12}$ and "thienyl or phenyl which may be substituted respectively" in $R^2$ and $R^5$, the following groups (a) to (h) are listed.

(a) halogen;

(b) —OH, —O—$R^Z$, —O-aryl, —OCO—$R^Z$, oxo (=O);

(c) —SH, —S—$R^Z$, —S-aryl, —SO—$R^Z$, —SO-aryl, —$SO_2$—$R^Z$, —$SO_2$-aryl, sulfamoyl which may be substituted with one or two $R^Z$s;

(d) amino which may be substituted with one or two $R^Z$s, —NHCO—$R^Z$, —NHCO-aryl, —$HNCO_2$—$R^Z$, —NH-$CONH_2$, $NHSO_2$—$R^Z$, —$NHSO_2$-aryl, —$NHSO_2NH_2$, nitro;

(e) —CHO, —CO—$R^Z$, —$CO_2H$, —$CO_2$—$R^Z$, carbamoyl which may be substituted with one or two $R^Z$s, cyano;

(f) aryl or cycloalkyl, each of which may be substituted with one or more groups selected from the group consisting of —OH, —O-lower alkyl, amino which may be substituted with one or two lower alkyls, halogen and $R^Z$;

(g) aromatic heterocycle or non-aromatic heterocycle, each of which may be substituted with one or more groups selected from the group consisting of —OH, —O-lower alkyl, amino which may be substituted with one or two lower alkyls, halogen and $R^Z$; and (h) lower alkyl which may be substituted with one or more groups selected from substituents shown in (a) to (g).

Permissible substituents in "lower alkyl which may be substituted" and "lower alkylene which may be substituted" in $R^{11}$ and "lower alkyl which may be substituted" in $R^{12}$ include the groups listed in (a) to (g).

Examples of permissible substituents in "aromatic heterocycle, aryl or cyclic amino which may be substituted respectively" in $R^3$ and $R^6$ can include halogen, lower alkyl which may be substituted with one or more halogens, —OH, —O—$R^Z$, oxo, amino which may be substituted with one or two $R^Z$s and a group represented by formula (III). When the substituent is amino substituted with two $R^Z$s, the two $R^Z$s may be the same or different.

$$—X—Y\text{-}Z \qquad (III)$$

[Symbols in the formula have the following meanings.

X: cyclic aminediyl which may be substituted with one or more groups selected from the group consisting of —OH, —O-lower alkyl, halogen, oxo and $R^Z$.

Y: single bond, —O-lower alkylene or —N(lower alkyl)-lower alkylene.

Z: substituent group W, -cyclic aminediyl-substituent group W or —CO-cyclic aminediyl-substituent group W.]

"Cyclic aminediyl" means a divalent group of 3- to 8-membered non-aromatic cyclic amine which has at least one nitrogen atom and may have further one or more hetero atoms selected from the member consisting of nitrogen, oxygen and sulfur, provided when plural hetero atoms are provided, they may be the same or different and at least one nitrogen atom has a bonding site. Specific examples thereof can include divalent groups of azetidine, pyrrolidine, piperidine, azepane, azocane, azonane, azecane, piperazine, homopiperazine, morpholine and thiomorpholine.

The compounds represented by formula (I) which are an active ingredient of medications of the present invention or the compounds represented by formula (III) which are compounds of the present invention sometimes contain an asymmetric carbon atom according to the type of the substituent, and optical isomers may be present based on this. The present invention includes all of a mixture of these optical isomers and optical isomers which are isolated. Further, with respect to the compounds according to the present invention, tautomers sometimes exist. The present invention includes tautomers which are separated or a mixture thereof. Still further, the present invention includes labeled compounds, namely the compounds of the present invention with one or more atoms substituted with a radioactive isotope or a nonradioactive isotope.

The compounds according to the present invention are sometimes formed into salts which are included in the present invention so long as they are pharmaceutically acceptable salts. Specific examples thereof include acid addition salts with inorganic acids such as hydrochloric acid, hydrobromic acid, hydroiodic acid, sulfuric acid, nitric acid and phosphoric acid or organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid and glutamic acid, salts with inorganic bases containing metals such as sodium, potassium, calcium and magnesium or organic bases such as methylamine, ethylamine, ethanolamine, lysine and ornithine, ammonium salts and the like. The present invention also includes hydrates, solvates and polycrystalline substances of the compounds of the present invention and the pharmaceutically acceptable salts thereof. The present invention also includes all of compounds which are converted to the compounds represented by formula (I) or (III) or the salts thereof by being metabolized in vivo, so-called prodrugs. Groups that form the prodrugs of the present invention include groups described in Prog. Med. 5:2157-2161 (1985) and groups described in Hirokawa Shoten, 1990, "Iyakuhin no Kaihatsu", vol. 7, Bunshi Shekkei pp. 163-198.

(Process)

The compounds and the pharmaceutically acceptable salts thereof according to the present invention can be produced by utilizing characteristics based on the basic structure or the types of the substituents and applying various known synthesis processes. Typical processes are described below. Some types of functional groups are substituted with appropriate protective groups, namely groups easily convertible to the very functional groups in the stage of starting materials or intermediates, which is sometimes effective in the production technique. Thereafter, protective groups are removed, as required, to be able to obtain the desired compounds. Examples of such functional groups can include a hydroxyl group, a carboxyl group, an amino group and the like. Examples of the protective groups can include protective groups described in, for example, Green and Wuts, "Protective Groups in Organic Synthesis (third edition)". These may properly be used according to reaction conditions.

(First process)

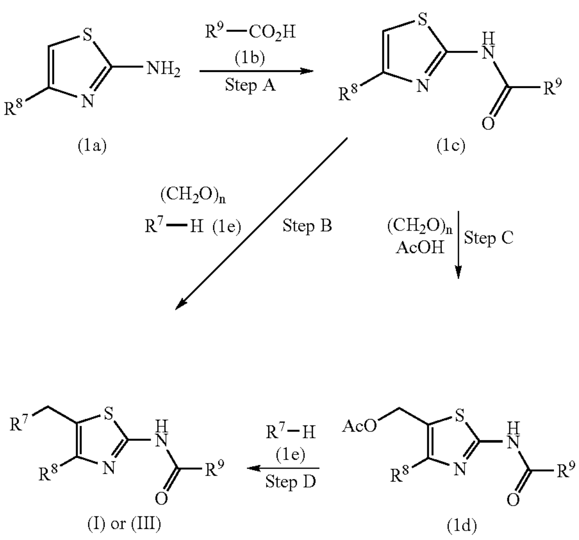

(1a) (1c) (1d) (I) or (III)

(wherein $R^7$ represents a group represented by the foregoing formula (II) in which $R^{11}$ is H, lower alkyl which may be substituted or cycloalkyl which may be substituted or represents a cyclic amino group which may be substituted; and $R^8$ represents the foregoing group represented by $R^2$ or $R^5$; $R^9$ represents the forgoing group represented by $R^3$ or $R^6$ or a group which is convertible to $R^3$ or $R^6$ by a method which can ordinarily be employed by a skilled person. This applies to the following.)

This process is a process for producing a compound, among the compounds of the present invention represented by formula (I) or (III), in which A is methylene, $R^1$ and $R^2$ (or $R^4$ and $R^5$) are not crosslinked, and $R^1$ or $R^4$ and A are not ring-closed.

(Step A)

This step is a step in which compound (1c) is produced by amidation of compound (1a) or its salt with compound (1b) or its reactive derivative in a usual manner and removing a protective group as required.

As the amidation in this step, amidation which can ordinarily be used by a skilled person is employable. Especially, a method in which phosphorus oxychloride is used in a pyridine solvent, and a method in which a condensing agent such as 1-ethyl-3-(3-dimethylaminopropyl)carbodiimide hydrochloride (WSC.HCl), dicyclohexylcarbodiimide, carbonyldiimidazole, diphenylphosphorylazide or diethylphosphorylcyanide is used in the presence of 1-hydroxybenzotriazole (HOBt) are advantageously used.

The reaction varies with reactive derivatives or a condensing agent used. Usually, the reaction is conducted in an organic solvent inactive to the reaction under cooling, under cooling to room temperature or under room temperature to heating, examples of the organic solvent including halogenated hydrocarbons such as dichloromethane, dichloroethane and chloroform, aromatic hydrocarbons such as benzene, toluene and xylene, ethers such as ether and tetrahydrofuran (THF), esters such as ethyl acetate (EtOAc), acetonitrile, N,N-dimethylformamide (DMF), dimethyl sulfoxide (DMSO) and the like.

(Step B)

This step is a step in which compound (I) or (III) of the present invention is produced by introducing an aminomethyl group in the 5-position of thiazole of compound (1c) using a Mannich reaction with compound (1e). A method described in Altertson, N. F.; J Am Chem Soc 1948, 70, 669 or Bhargava, P. N.; Sharma, S. C.; Bull Chem Soc Jpn 1965, 38, 909. or a method corresponding thereto can be employed.

(Step C, Step D)

These steps are steps in which compound (I) or (III) of the present invention is produced by introducing an acetoxymethyl group in the 5-position of thiazole of compound (1c) and then conducting a nucleophilic substitution reaction with compound (1e) under a basic condition.

The acetoxymethylation in step C can be conducted under room temperature to heating or under room temperature to reflux by reacting compound (1c) with a formaldehyde aqueous solution or a p-formaldehyde in an acetic acid solvent. The reaction may be conducted by adding acetic acid in a solvent inactive to the reaction, such as halogenated hydrocarbons, aromatic hydrocarbons or ethers instead of an acetic acid solvent. In this case, a reactivity tends to be decreased. Further, the reaction may be conducted by addition of acetic anhydride.

The nucleophilic substitution reaction in step D can be conducted by reacting compound (1d) with compound (1e) in an organic solvent inactive to the reaction, such as halogenated hydrocarbons, aromatic hydrocarbons, ethers, esters, acetonitrile, DMF or DMSO in the presence of an organic base such as triethylamine or diisopropylethylamine and/or an inorganic base such as potassium carbonate, sodium carbonate, cesium carbonate or sodium hydrogencarbonate. For acceleration of the reaction, a catalyst such as dimethylaminopyridine may be added. Instead of the organic base and/or the inorganic base, a larger amount of compound (1e) may be used. The reaction varies with the base used. It can be conducted under cooling to room temperature, under room temperature to heating or under room temperature to reflux.

(Second process)

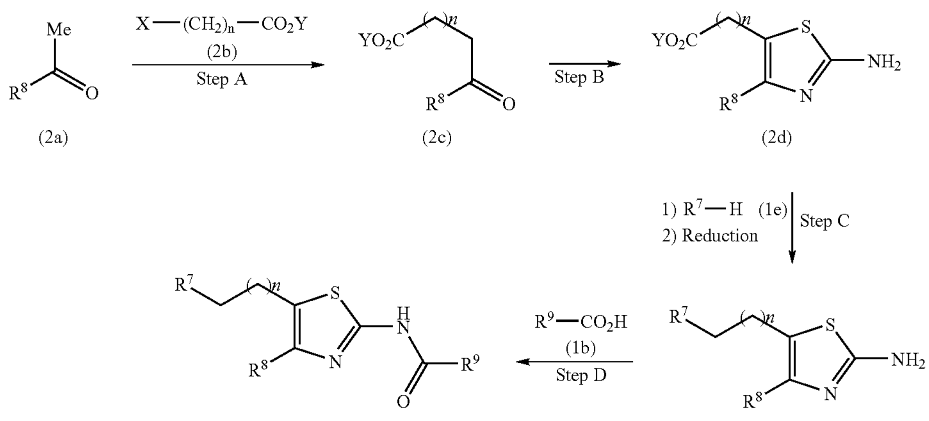

(2a) (2c) (2d) (2e) (I) or (III)

(wherein X represents a leaving group such as halogen; Y represents lower alkyl; and n represents an integer of from 1 to 6. This applies to the following.)

This process is a process for producing a compound, among the compounds of the present invention represented by formula (I) or (III), in which A or B is lower alkylene except methylene, $R^1$ and $R^2$ or $R^4$ and R are not crosslinked, and $R^1$ and A or $R^4$ and B are not ring-closed.

(Step A)

This step is a step in which compound (2c) is produced by condensing compound (2a) and compound (2b). A method described in HAND, E. S.; JOHNSON, S. C.; BAKER, D. C.; J Org Chem 1997, 62(5), 1348-1355 or a method corresponding thereto can be employed.

(Step B)

This step is a step in which the a-position of ketone in compound (2c) is halogenated and the compound is then reacted with thiourea to form a thiazole ring. A method described in Org. Syn. Coll. Vol. II, 1943, 32-32., and Maruzen, 1992, "Dai 4 han Jikken Kagaku Koza 19", pp. 431-435, or a method corresponding thereto can be employed.

(Step C)

This step is a step in which compound (2d) or the carboxylic acid compound subjected to hydrolysis as required is amidated according to step A in the first process and the amide bond is then converted to an aminomethylene bond by a reduction reaction. A method described in Maruzen, 1992, "Dai 4 han Jikken Kagaku Koza 26", pp. 227-228, or a method corresponding thereto can be employed.

(Step D)

This step is a step in which compound (I) or (III) of the present invention is produced by amidation of compound (2e) with compound (1b). The step can be conducted according to step A in the first process.

(Third process)

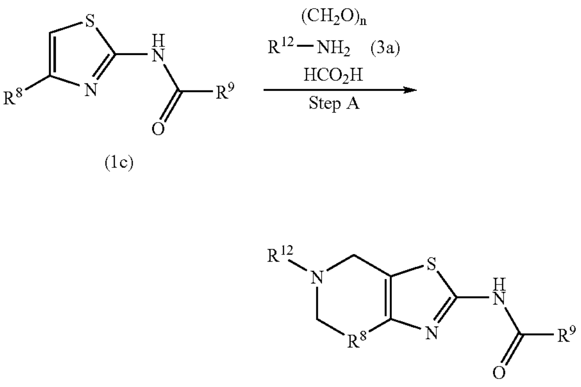

(1c) (I) or (III)

(wherein $R^{12}$ represents the foregoing group. This applies to the following.)

This process is a process for producing a compound, among the compounds of the present invention represented by formula (I) or (III), in which $R^1$ and $R^2$ (or $R^4$ and $R^5$) are crosslinked by $R^{11}$. $R^{11}$ is present as methylene crosslinked on $R^2$ or $R^5$ when A or B is methylene and $R^1$ or $R^4$ is a group represented by formula (II) according to the foregoing definition.

(Step A)

This step is a step in which an aminomethyl group is introduced into the 5-position of thiazole of compound (1c) using a Mannich reaction with compound (1c) and phenyl or thienyl represented by $R^2$ nucleophilically attacks iminium formed by the subsequent second-stage Mannich reaction to give a tricyclic compound, the compound of the present invention. The step can be conducted according to step B in the first process.

(Fourth process)

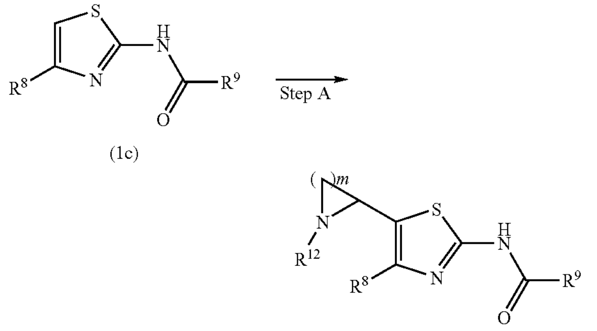

(1c)

(I) or (III)

(wherein m represents an integer of from 1 to 6. This applies to the following.)

This process is a process for producing a compound, among the compounds of the present invention represented by formula (I) or (III), in which $R^1$ and A (or $R^4$ and B) are ring-closed by $R^{11}$. $R^{11}$ is present as lower alkylene which may be substituted and which is ring-closed on A or B when A or B is methylene and $R^1$ or $R^4$ is a group represented by formula (II) according to the foregoing definition.

(Step A)

This step can be conducted according to a method of. Van Tamelin, E. E.; Knapp, G. C.; J. Am. Chem. Soc., 77, 1860, 1955.

In the first to fourth processes, the next step can proceed by converting a group represented by $R^9$ to $R^3$ or $R^6$ in an appropriate time of the foregoing step. As to the conversion method, for example, a method can be described in which in step A, 5,6-dichloropyridin-3-yl or 3,4,5-difluorophenyl is introduced as $R^9$, and ipso substitution is conducted by a nucleophilic reaction in an appropriate time, for example, before step B, before step C or before step D in the first process to convert the group to $R^3$ or $R^6$, a partial structure of the compounds according to the present invention.

Further, some compounds represented by formula (I) or (III) may be produced from the compounds of the present invention which have been obtained in the foregoing manner by arbitrarily combining steps that can ordinarily be employed by a skilled person, such as known alkylation, acylation, substitution reaction, oxidation, reduction and hydrolysis.

The thus-produced compounds according to the present invention are isolated and purified either in free form or as salts thereof by undergoing salt-forming treatment in a usual manner. Isolation and purification are performed by ordinary chemical procedures such as extraction, concentration, distillation, crystallization, filtration, recrystallization and various chromatographies.

Various isomers can be isolated in a usual manner by utilizing a difference in physicochemical properties between isomers. For example, a racemic mixture can be introduced into optically pure isomers by a general racemic compound resolution method, for example, a method in which the mixture is formed into a diastereomer salt with a general optically active acid such as tartaric acid to conduct optical resolution. A diastereo-mixture can be separated by, for example, fractional crystallization or various chromatographies. An optically active compound can be produced using an appropriate optically active starting material.

INDUSTRIAL APPLICABILITY

The compounds according to the present invention have an excellent platelet increasing function. Therefore, the compounds according to the present invention are useful for treating and/or preventing various thrombocytopenias such as thrombocytopenia in anemia and myelodysplastic syndrome, thrombocytopenia caused by chemotherapy and radiotherapy of malignant tumor, thrombocytopenia in idiopathic thrombocytopenic purpura, thrombocytopenia in hepatic diseases and thrombocytopenia caused by HIV. When there is a possibility of causing thrombocytopenia by chemotherapy or radiotherapy, previous administration is also possible before conducting these therapies.

Pharmacological functions of the compounds according to the present invention were confirmed by the following tests.

(i) Human c-mpl-Ba/F3 Cell Growth Test

In a 96-well microplate, $2\times10^5$ cells/ml of human c-mpl-Ba/F3 cells were cultured at 37° C. in 10% fetal bovine serum-containing RPMI1640 medium (100 μl/well) containing each test compound at each concentration. After 24 hours from the start-up of culture, 10 μl/well of WST-1/1-methoxy PMS (cell counting kit, Dojin) was added. Immediately after addition and 2 hours after addition, absorbance of A450/A650 was measured with a microplate reader (Model 3350: Bio-Rad), and an increase in absorbance for 2 hours was defined as a growth activity of each test compound. The results are shown in Table 1.

Symbols in the table have the following meanings.

pot: Concentration of each test compound at which to accelerate cell growth by 30% of a maximum cell growth activity of compound A (compound A and rhTPO in rhTPO)

Efficacy: Maximum cell growth activity of each test compound when a maximum cell growth activity of compound A (compound A and rhTPO in rhTPO) is defined as 100%.

Compound A refers to a compound in Example 9 of the foregoing Patent Document 10.

TABLE 1

Human c-mpl-Ba/F3 cell growth activity

| Test Compound | Pot [nM] | Efficacy [%] |
|---|---|---|
| Example 65 | 4.3 | 114 |
| Example 71 | 2.0 | 110 |
| Example 84 | 4.2 | 103 |
| Example 85 | 3.3 | 107 |
| Example 90 | 2.0 | 94 |
| Example 100 | 2.9 | 117 |
| Example 101 | 3.1 | 108 |
| Example 104 | 3.5 | 105 |
| Example 106 | 2.1 | 112 |
| Example 107 | 1.5 | 112 |
| Example 109 | 3.9 | 95 |
| Example 111 | 6.0 | 87 |
| Example 150 | 3.6 | 102 |
| Example 151 | 8.4 | 99 |
| Example 153 | 6.1 | 99 |
| Example 222 | 4.4 | 102 |
| Example 226 | 4.6 | 88 |
| Example 227 | 3.2 | 88 |
| Example 315 | 3.2 | 98 |
| Comparative Compound 1 | 4.4 | 101 |
| Comparative Compound 2 | 2.1 | 96 |
| Comparative Compound 3 | 6.9 | 96 |
| Comparative Compound 4 | 251 | 95 |
| Compound A | 10 | 87 |
| rhTPO | 0.012 | 100 |

In the table, Comparative Compound 1 is a compound of Compound No. A-1 in the foregoing Patent Document 7; Comparative Compound 2 is a compound of Compound No. A-14 in the foregoing Patent Document 8; Comparative Compound 3 is a compound of Compound No. J-14 in the foregoing Patent Document 8; and Comparative Compound 4 is a compound in Example 2 of the foregoing Patent Document 9. Structures of Comparative Compounds 1 to 4 and Compound A are shown below.

Comparative compound 1

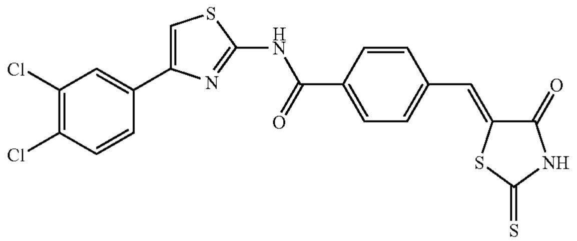

Comparative compound 2

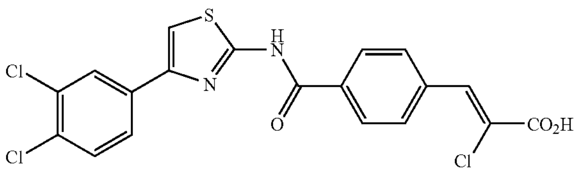

Comparative compound 3

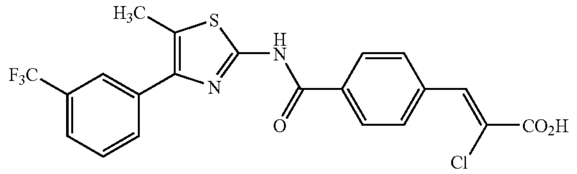

Comparative compound 4

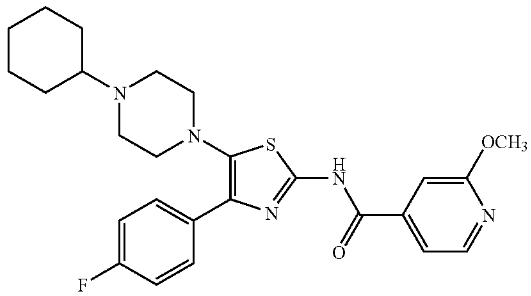

Compound A

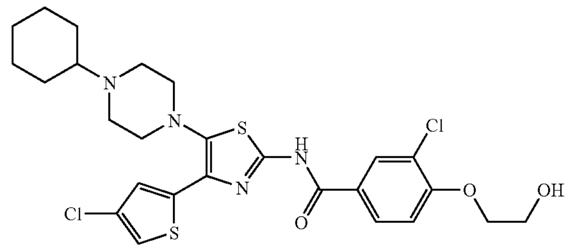

From the foregoing results, the compounds of the present invention have been confirmed to have the Ba/F3 cell growth function mediated by human c-Mpl.

(ii) Test for Measuring a Function of Accelerating Formation of Megakaryocytic Colonies Human $CD34^+$ cells were cultured in a 2-well chamber slide in the presence of a test product at 37° C. for from 10 to 14 days using MegaCult™-C (StemCell Technologies). After dehydration and fixation were conducted according to the attached manual, dying was conducted with an anti-glycoprotein IIb/IIIa antibody. The number of colonies for 1 well was counted by a microscope on condition that a population of 3 or more dyed megakaryocytes was one colony. An $EC_{30}$ value of each test compound was calculated from a dose curve.

Consequently, with respect to the $EC_{30}$ value of the compounds of the present invention, the compound in Example 71 is 20 nM, the compound in Example 100 34 nM, the compound in Example 104 36 nM, the compound in Example 106 23 nM, and the compound in Example 315 45 nM. It has been confirmed that the compounds of the present invention have the excellent function of accelerating formation of megakaryocytic colonies.

(iii) Mouse Oral Administration Test 3 mg/kg or 10 mg/kg (100 mg/kg in Comparative Compounds 1 to 3) of a test compound dissolved or suspended in a 0.5% methylcellulose aqueous solution was orally administered to a male ICR mouse. After 2 hours from administration, a blood was sampled from the subabdominal large vein using 1/10-volume 3.8% sodium citrate as an anticoagulant. Centrifugation was performed at 12,000 rpm for 3 minutes. The resulting plasma was heated at 56° C. for 30 minutes, and added to a system of the human c-mpl-Ba/F3 cell growth test described in (i) such that the final concentration of the plasma reached 0.3%, 1% or 3% (10% in Comparative Compounds 1 to 3) to measure a cell growth activity. The cell growth activity (%) of each plasma was measured when the maximum cell growth activity of each test compound was defined as 100%.

TABLE 2

Human c-mpl-Ba/F3 cell growth activity of a plasma after oral administration

| Test Compound | Dose [mg/kg p.o.] | Dilution rate [%] | Cell growth activity[%] |
|---|---|---|---|
| Example 65 | 3 | 3 | ≧80 |
| Example 71 | 3 | 3 | ≧80 |
| Example 84 | 3 | 1 | ≧80 |
| Example 85 | 3 | 1 | ≧80 |
| Example 90 | 3 | 0.3 | ≧80 |
| Example 100 | 3 | 3 | ≧80 |
| Example 101 | 3 | 1 | 76 |
| Example 104 | 3 | 1 | 63 |
| Example 106 | 3 | 1 | 63 |
| Example 109 | 3 | 1 | 59 |
| Example 150 | 3 | 0.3 | 28 |
| Example 151 | 10 | 3 | 24 |
| Example 153 | 10 | 3 | 29 |
| Example 314 | 3 | 3 | 52 |
| Comparative Compound 1 | 100 | 10 | <10 |
| Comparative Compound 2 | 100 | 10 | <10 |
| Comparative Compound 3 | 100 | 10 | <10 |

Comparative Compounds 1 to 3 in the table are the same as Comparative Compounds 1 to 3 in the foregoing Table 1 respectively.

From the foregoing results, it has been confirmed that the compounds of the present invention have an oral activity in mice. Especially, it has been found that in the comparative compounds, the oral activity is little shown even "under a condition of 100 mg/kg—10% dilution", whereas in the compounds of the present invention, the good oral activity is exhibited even "under a condition of a lower dose of 3 mg/kg or 10 mg/kg—higher dilution of 3% or less". This is quite unexpected, and is considered to have been achieved by introduction of lower alkylene having an amino group as a substituent in the 5-position of thiazole. In Comparative Compound 2 and Comparative Compound 3, the cell growth activity has been less than 10% also in the lower dose (10 mg/kg p.o.).

It has been confirmed that a platelet increasing activity is observed by administering the compound of the present invention to a mouse in which human platelet production has been identified after transplantation of human hematopoietic stem cells.

The medication of the present invention can be prepared by an ordinary method using at least one of the compounds represented by formula (I) or (III) according to the present invention as well as a carrier, an excipient and other additives for use in drugs which are commonly used in formulation. The administration may be any of oral administration with tablets, pills, capsules, granules, powders, liquid preparations or the like and parenteral administration with injections such as intravenous injection and intramuscular injection, administration with suppositories, transnasal administration, permucosal administration or percutaneous administration.

As a solid composition for oral administration according to the present invention, tablets, powders, granules and the like are used. In such a solid composition, one or more active substances are mixed with at least one inactive diluent such as lactose, mannitol, glucose, hydroxypropylcellulose, microcrystalline cellulose, starch, polyvinyl pyrrolidone or magnesium aluminate metasilicate. The composition may contain, according to a usual method, additives other than an inactive diluent, for example, a lubricant such as magnesium stearate, a disintegrant such as calmellose calcium, a stabilizer and a solubilizer. Tablets or pills may be coated, as required, with a sugar coating such as sucrose, gelatin, hydroxypropylcellulose or hydroxypropylmethylcellulose phthalate, or a gastric or enteric film.

A liquid composition for oral administration contains an emulsifying agent, a liquor, a suspending agent, a syrup, an elixir and the like which are pharmaceutically acceptable, and an inactive diluent which is generally used, such as purified water or ethanol (EtOH). This composition may contain, in addition to the inactive diluent, aids such as a wetting agent and a suspending agent, a sweetener, a flavor, an aromatic and a preservative.

An injection for parenteral administration contains a liquor and a suspending agent which are sterile and aqueous or non-aqueous and an emulsifying agent. Examples of the aqueous liquor and suspending agent include distilled water for injection and a physiological saline solution. Examples of the non-aqueous liquor and suspending agent include vegetable oils such as propylene glycol, polyethylene glycol and olive oil, alcohols such as EtOH, polysorbate 80 and the like. Such a composition may further contain aids such as a preservative, a wetting agent, an emulsifying agent, a dispersing agent, a stabilizer and a solubilizing agent. These are sterilized by filtration through a bacteria holding filter, incorporation of a disinfectant or irradiation. Further, these may be formed into a sterile solid composition which is used by being dissolved in sterile water or a sterile solvent for injection before use.

In case of oral administration, a dose for one day is generally from approximately 0.0001 to 50 mg/kg, preferably from approximately 0.001 to 10 mg/kg, more preferably from 0.01 to 1 mg/kg per body weight. This is administered either once or in divided portions, from 2 to 4 times. In case of intravenous administration, a dose for one day is from approximately 0.0001 to 1 mg/kg, preferably from approximately 0.0001 to 0.1 mg/kg. This is administered either once or plural times per day. The dose is properly determined according to each case in consideration of the condition, the age, the sex and the like of patients.

BEST MODE FOR CARRYING OUT THE INVENTION

The present invention is specifically described below by referring to Examples. However, the invention is not limited at all by these Examples. Starting compounds used in Examples include novel substances, and processes for producing such starting compounds from known products are described as Reference Examples.

REFERENCE EXAMPLE 1

Potassium carbonate and allyl bromide were added to a DMF solution of 3,4,5-trifluorobenzoic acid, and the mixture was stirred overnight to obtain a crude allyl ester. Potassium carbonate was added to a DMF solution of the crude allyl ester and ethyl isonipecotate, and the mixture was stirred overnight at room temperature to obtain a piperidine substitution product. Morpholine and tetrakis(triphenylphosphine)palladium (catalytic amount) were added to a THF solution of the piperidine substitution product, and the mixture was stirred at 60° C. for 2 hours and at room temperature for 4 days. After the solvent was distilled off, ether and EtOAc were added, and the mixture was washed 10 times with an saturated sodium hydrogencarbonate aqueous solution. Conc. hydrochloric acid was added to the collected aqueous layer, and the resulting precipitate was collected by filtration to obtain 4-[4-(ethoxycarbonyl)piperidin-1-yl]-3,5-difluorobenzoic acid.

REFERENCE EXAMPLE 2

Potassium carbonate and 3-(tert-butyldimethylsilyloxy)propyl bromide were added to a DMF solution of ethyl 3-chloro-5-fluoro-4-hydroxybenzoate, and the mixture was stirred at 50° C. to obtain ethyl 4-[3-(tert-butyldimethylsilyloxy)propoxy]-3-chloro-5-fluorobenzoate.

Compounds in Reference Examples 3 and 4 shown in Table 3 were produced in the same manner as in Reference Example 2 using the corresponding starting materials respectively.

REFERENCE EXAMPLE 5

Anhydrous piperazine was added to a THF solution of methyl 3,4-difluorobenzoate, and the mixture was stirred at 60° C. for 18 hours to obtain methyl 3-fluoro-4-piperazin-1-ylbenzoate.

REFERENCE EXAMPLE 6

Di-tert-butyl dicarbonate and 4-dimethylaminopyridine were added to a 1,2-dichloroethane solution of the compound in Reference Example 5, and the mixture was stirred at room temperature for 10 minutes to obtain tert-butyl 4-[2-fluoro-4-(methoxycarbonyl)phenyl]piperazine-1-carboxylate.

REFERENCE EXAMPLE 7

N-chlorosuccinimide was added to a DMF solution of the compound in Reference Example 6, and the mixture was stirred at room temperature for 3 hours to obtain tert-butyl 4-[2-chloro-6-fluoro-4-(methoxycarbonyl)phenyl]piperazine-1-carboxylate.

REFERENCE EXAMPLE 8

A 1M NaOH aqueous solution (aq) was added to an MeOH-THF mixed solution of the compound in Reference Example 2, and the mixture was stirred at room temperature for 16 hours to obtain 4-[3-(tert-butyldimethylsilyloxy)propoxy]-3-chloro-5-fluorobenzoic acid.

Compounds in Reference Examples 9 to 11 shown in Table 3 were produced in the same manner as in Reference Example 8 using the corresponding starting materials respectively.

REFERENCE EXAMPLE 12

Thionyl chloride was added to an MeOH solution of the compound in Reference Example 11, and the mixture was stirred at room temperature for 22 hours to obtain 4-[3-(methoxycarbonyl)propoxy]-3-fluorobenzoic acid.

Symbols in the table have the following meanings (this applies to the following).

Rf: Reference Example No.

Data: Physical data (MS:FAB-MS$(M+H)^+$; MN:FAB-MS $(M-H)^-$; MM:FAB-MS$(M)^+$), R, $R^1$, $R^2$, $R^3$, $R^4$, X, Y: Substituents in the general formulas (Me: methyl, Et: ethyl, iPr: isopropyl, cPr: cyclopropyl, nBu: normal butyl, iBu: isobutyl, tBu: tertiary butyl, Ph: phenyl, Py: pyridyl, Boc: tert-butyloxycarbonyl, The: thienyl, azet: azetidin-1-yl, pyrr: pyrrolidin-1-yl, pipe: piperidin-1-yl, pipa: piperazin-1-yl, mor: morpholin-4-yl, TBS: tertiary butyldimethylsilyl, di:di. The number before the substituent indicates a substitution position. Accordingly, for example, 3,5-diF-4-(4-$EtO_2C$-pipe)Ph refers to 3,5-difluoro-4-(4-ethoxycarbonylpiperidin-1-yl)phenyl, and 4-Me-2-The refers to 4-methylthiophen-2-yl).

TABLE 3

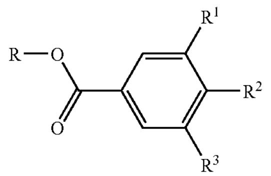

| Rf | $R^1$, $R^2$, $R^3$, R | | | | Data |
|---|---|---|---|---|---|
| 1 | $R^1$ = F, | $R^2$ = 4-$EtO_2C$-pipe, | $R^3$ = F, | R = H | MS; 314. |
| 2 | $R^1$ = Cl, | $R^2$ = $TBSO(CH_3)_3O$—, | $R^3$ = F, | R = Et | MS; 391. |
| 3 | $R^1$ = OMe, | $R^2$ = $TBSO(CH_2)_2O$—, | $R^3$ = H, | R = Et | MS; 355. |
| 4 | $R^1$ = F, | $R^2$ = $EtO_2C(CH_2)_3O$—, | $R^3$ = H, | R = Me | MS; 285. |
| 5 | $R^1$ = F, | $R^2$ = pipa, | $R^3$ = H, | R = Me | MS; 239. |
| 6 | $R^1$ = F, | $R^2$ = 4-Boc-pipa, | $R^3$ = H, | R = Me | MS; 339. |
| 7 | $R^1$ = Cl, | $R^2$ = 4-Boc-pipa, | $R^3$ = F, | R = Me | MS; 373. |
| 8 | $R^1$ = Cl, | $R^2$ = $TBSO(CH_2)_3O$—, | $R^3$ = F, | R = H | MS; 363. |
| 9 | $R^1$ = Cl, | $R^2$ = 4-Boc-pipa, | $R^3$ = F, | R = H | MS; 359. |
| 10 | $R^1$ = OMe, | $R^2$ = $TBSO(CH_2)_2O$—, | $R^3$ = H, | R = H | MS; 327. |
| 11 | $R^1$ = F, | $R^2$ = $HO_2C(CH_2)_3O$—, | $R^3$ = H, | R = H | MN; 241. |
| 12 | $R^1$ = F, | $R^2$ = $MeO_2C(CH_2)_3O$—, | $R^3$ = H, | R = H | MS; 257. |

REFERENCE EXAMPLE 13

Bromine was added to an ether solution of 4-chloro-2-acetylthiophene under ice cooling, and the mixture was stirred at room temperature for 2 hours to obtain a brominated compound. Thiourea was added to an EtOH solution of the brominated compound at room temperature, and the mixture was stirred overnight at 80° C. to obtain 2-amino-4-(4-chlorothiophen-2-yl)thiazole.

A compound in Reference Example 14 shown in Table 4 was obtained in the same manner as in Reference Example 13 using the corresponding starting material.

TABLE 4

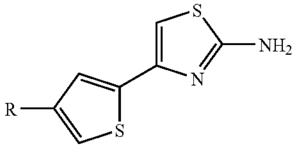

| Rf | R | Data |
|---|---|---|
| 13 | Cl | MS; 217. |
| 14 | Me | MS; 197. |

REFERENCE EXAMPLE 15

Phosphorus oxychloride was added to a pyridine suspension of the compound in Reference Example 13 and 5,6-dichloronicotinic acid. The temperature was gradually raised, and the mixture was stirred overnight at room temperature to obtain 5,6-dichloro-N-[4-(4-chlorothiophen-2-yl)thiazol-2-yl]nicotinamide.

Compounds in Reference Examples 16 to 22 shown in Table 5 were produced in the same manner as in Reference Example 15 using the corresponding starting materials.

TABLE 5

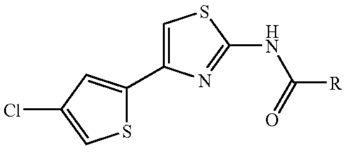

| Rf | R | Data |
|---|---|---|
| 15 | 5,6-diCl-3-Py | MS; 390. |
| 16 | 2-MeO-4-Py | MS; 352. |
| 17 | 3,5-diF-4-(4-$EtO_2C$-pipe)Ph | MS; 512. |
| 18 | 3-Cl-5-F-4-$TBSO(CH_2)_3O$—Ph | MS; 561. |
| 19 | 3-Cl-5-F-4-(4-Boc-pipa)Ph | MS; 557. |
| 20 | 3-Cl-4-$MeOCH_2O$—Ph | MS; 415. |
| 21 | 3-MeO-4-$TBSO(CH_2)_2O$—Ph | MS; 624. |
| 22 | 3-F-4-$MeO_2C(CH_2)_3O$—Ph | MS; 455. |

REFERENCE EXAMPLE 23

Pyridine, triethylamine and ethyl isonipecotate were added to the compound in Reference Example 15, and the mixture was stirred at 70° C. for 16 hours to obtain ethyl 1-(3-chloro-5-{[4-chlorothiophen-2-yl)thiazol-2-yl]carbamoyl}-2-pyridyl)piperidine-4-carboxylate.

Compounds in Reference Examples 24 to 31 shown in Table 6 were produced in the same manner as in Reference Example 23 using the corresponding starting materials respectively.

TABLE 6

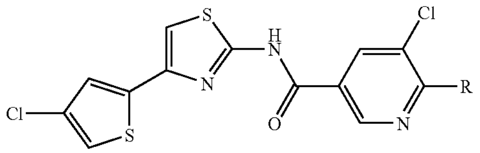

| Rf | R | Data |
|---|---|---|
| 23 | 4-$EtO_2C$-pipe | MS; 511. |
| 24 | 3-$EtO_2C$-pipe | MS; 511. |
| 25 | 3-$MeO_2C$-pyrr | MS; 483. |
| 26 | (R)-3-$MeO_2CCH_2O$-pyrr | MS; 513. |
| 27 | 4-$EtO_2CCH_2$-pipe | MS; 525. |
| 28 | 2-$EtO_2C$-mor | MS; 513. |
| 29 | (S)-3-$MeO_2C$-pyrr | MS; 483. |
| 30 | 3-$EtO_2C$-azet | MS; 483. |
| 31 | 4-$tBuO_2CCH_2O$-pipe | MS; 569. |

REFERENCE EXAMPLE 32

Acetic acid and a formaldehyde aqueous solution (36%) were added to the compound in Reference Example 23, and the mixture was stirred overnight at 100° C. to obtain ethyl 1-(5-acetoxymethyl-4-(4-chlorothiophen-2-yl)thiazol-2-yl)carbamoyl)-3-chloro-2-pyridyl)piperidine-4-carboxylate.

A compound in Reference Example 33 shown in Table 7 was produced in the same manner as in Reference Example 32 using the corresponding starting material.

TABLE 7

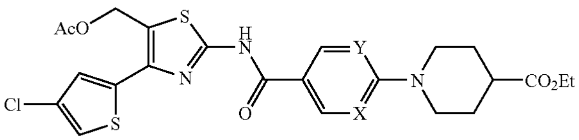

| Rf | X, Y | Data |
|---|---|---|
| 32 | X = N, Y = C—Cl | MS; 583. |
| 33 | X = C—F, Y = C—F | MS; 584. |

Compounds in Reference Examples 34 and 35 shown in Table 8 were produced in the same manner as in Example 1 to be described later using the corresponding starting materials respectively.

TABLE 8

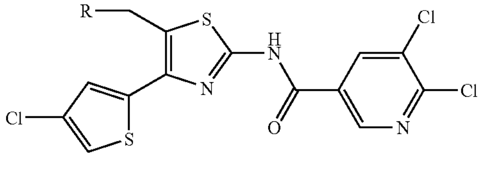

| Rf | R | Data |
|---|---|---|
| 34 | pipe | MS; 487. |
| 35 | nBuN(Me) | MS; 489. |

REFERENCE EXAMPLE 36

A 4M HCl-EtOAc solution was added to a chloroform-EtOH mixed solution of the compound in Reference Example 19 under ice cooling, and the mixture was stirred at room temperature for 17 hours to obtain 3-chloro-N-[4-(4-chlorothiophen-2-yl)thiazol-2-yl]-5-fluoro-4-piperazin-1-ylbenzamide hydrochloride.

REFERENCE EXAMPLE 37

Potassium carbonate and ethyl bromoacetate were added to a DMF solution of the compound in Reference Example 36, and the mixture was stirred at room temperature for 23 hours to obtain ethyl [4-(2-chloro-4-{[4-(4-chlorothiophen-2-yl)thiazol-2-yl]carbamoyl}-6-fluorophenyl)piperazin-1-yl]acetate.

TABLE 9

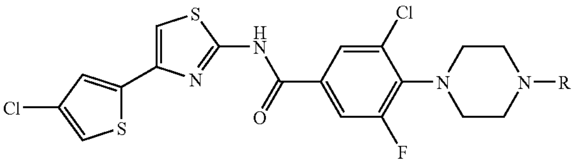

| Rf | R | Data |
|---|---|---|
| 36 | H | MS; 457. |
| 37 | $EtO_2CCH_2$ | MS; 543. |

REFERENCE EXAMPLE 38

Phosphorus oxychloride was added to a pyridine suspension of 2-amino-4-[3-(trifluoromethyl)phenyl]thiazole and 5,6-dichloronicotinic acid at −30° C. The temperature was gradually raised, and the mixture was stirred overnight at room temperature. After the solvent was distilled off under reduced pressure, pyridine and EtOH were added, and the mixture was stirred at 50° C. for 30 minutes. Triethylamine and ethyl isonipecotate were added at room temperature, and the solution was stirred at 80° C. for 15 hours to obtain ethyl 1-[3-chloro-5-({4-[3-trifluoromethyl)phenyl]thiaozl-2-yl}carbamoyl)-2-pyridyl]piperidine-4-carboxylate.

Compounds in Reference Examples 39 and 40 shown in Table 10 were produced in the same manner as in Reference Example 38 using the corresponding starting materials respectively.

TABLE 10

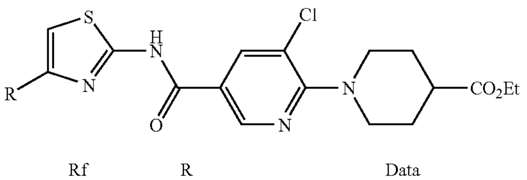

| Rf | R | Data |
|---|---|---|
| 38 | 3-$F_3C$—Ph | MS; 539. |
| 39 | 4-F—Ph | MS; 489. |
| 40 | 4-Me-2-The | MS; 491. |

The compound in Reference Example 41 shown in Table 11 was produced in the same manner as in Reference Example 8, and the compound in Reference Example 42 in the same manner as in Example 8 to be described later, using the corresponding starting materials respectively.

TABLE 11

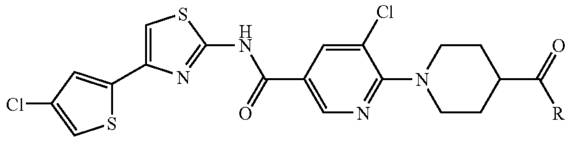

| Rf | R | Data |
|---|---|---|
| 41 | HO | MS; 483. |
| 42 | $MeO_2CCH_2NH$ | MS; 554. |

REFERENCE EXAMPLE 43

Phenyl chloroformate and pyridine were added to a THF solution of the compound in Reference Example 13, and the mixture was stirred at room temperature for 1.5 hours to obtain phenyl N-[4-(4-chlorothiophen-2-yl)thiazol-2-yl]carbamate.

REFERENCE EXAMPLE 44

A mixture of ethyl N-(piperidin-4-yl)isonipecotate hydrochloride and isopropyl N-(piperidin-4-yl)isonipecotate and triethylamine were added to a DMF solution of the compound in Reference Example 43, and the mixture was stirred at 80° C. for 12 hours to obtain an ester mixture. The ester mixture was dissolved in MeOH, and triethylamine and sodium ethoxide were added. The solution was stirred at from room temperature to 50° C. for 18 hours to obtain methyl 1'-{[4-(4-chlorothiophen-2-yl)thiazol-2-yl]carbamoyl}-1,4'-bipiperidine-4-carboxylate.

TABLE 12

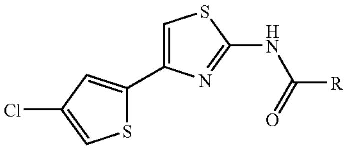

| Rf | R | Data |
|---|---|---|
| 43 | PhO | MS; 337. |
| 44 | 4-(4-$MeO_2C$-pipe)pipe | MS; 469. |

REFERENCE EXAMPLE 45

The compound in Reference Example 45 shown in Table 13 was produced in the same manner as in Reference Example 13 using 4-(4-chlorothiophen-2-yl)-4-oxobutanoic acid ester (methyl ester:ethyl ester 3:2 mixture) as a starting material.

REFERENCE EXAMPLE 46

A compound in Reference Example 46 shown in Table 13 was produced in the same manner as in Reference Example 8 using the corresponding starting material.

REFERENCE EXAMPLE 47

Butylmethylamine, WSC.HCl, HOBt and triethylamine were added to a DMF solution of the compound in Reference Example 46, and the mixture was stirred at room temperature for 18 hours to obtain N-butyl-N-methyl-[2-amino-4-(4-chlorothiophen-2-yl)thiazol-5-yl]acetamide.

REFERENCE EXAMPLE 48

A THF solution of the compound in Reference Example 47 was added to a THF suspension of lithium aluminum hydride, and the mixture was stirred under reflux for 3 hours to obtain 2-amino-5-{2-[butyl(methyl)amino]ethyl}-4-(4-chlorothiophen-2-yl)thiazole.

REFERENCE EXAMPLE 49

A compound in Reference Example 49 shown in Table 13 was produced in the same manner as in Reference Example 15 using the corresponding starting material.

TABLE 13

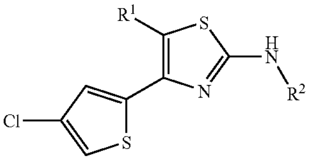

| Rf | $R^1$, $R^2$ | Data |
|---|---|---|
| 45 | $R^1$ = $RO_2CCH_2$(R; Me:Et = 3:2), $R^2$ = H | GC-MS; 288, 302. |
| 46 | $R^1$ = $HO_2CCH_2$, $R^2$ = H | MS; 275. |
| 47 | $R^1$ = nBuN(Me)$COCH_2$, $R^2$ = H | MS; 344. |
| 48 | $R^1$ = nBuN(Me)$(CH_2)_2$, $R^2$ = H | MS; 330. |
| 49 | $R^1$ = nBuN(Me)$(CH_2)_2$, $R^2$ = 5,6-diCl-3-Py-CO— | MN; 501, 503. |

REFERENCE EXAMPLE 50

Ethyl isonipecotate was added to a DMF solution of 2,6-dichloro-5-fluoronicotinic acid, and the mixture was stirred at 80° C. to obtain 2-chloro-6-[4-(ethoxycarbonyl)piperidin-1-yl]-5-fluoronicotinic acid.

REFERENCE EXAMPLE 51

Triethylamine and 10% palladium supported on carbon were added to a THF-EtOH solution of the compound in Reference Example 50, and the mixture was stirred at room temperature in a 4-atm hydrogen atmosphere to obtain 6-[4-(ethoxycarbonyl)piperidin-1-yl]-5-fluoronicotinic acid.

TABLE 14

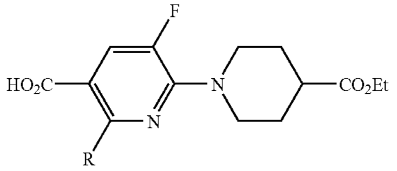

| Rf | R | Data |
|---|---|---|
| 50 | Cl | MS; 331. |
| 51 | H | MS; 297. |

Compounds in Reference Examples 52 and 53 shown in Table 15 were produced in the same manner as in Example 3 to be described later, compounds in Reference Examples 54 to 56 shown in Table 15 in the same manner as in Reference Example 15 and compounds in Reference Examples 57 to 64 shown in Table 15 in the same manner as in Example 1 to be described later, using the corresponding starting materials respectively.

amino]methyl}thiazol-2-yl)carbamoyl]-2-pyridyl}piperidine-4-carboxylate.

EXAMPLE 3

110 µl of a formaldehyde aqueous solution (35%) and 76 µl of acetic acid were added to 2 ml of 1.2-dichloroethane solution of 79 mg of ethyl 1-[3-chloro-5-({4-(4-chlorothiophen-2-yl)-5-[(cyclobutylamino)methyl]thiazol-2-yl}carbamoyl)-2-pyridyl]piperidine-4-carboxylate, and the mixture was stirred at room temperature for 1 hour. Subsequently, 45 mg of $NaBH(OAc)_3$ was added, and the solution was stirred at room temperature for 1 hour. Chloroform was added to the reaction solution, and the organic layer was washed with a saturated sodium hydrogencarbonate aqueous solution, with water and with brine, and then dried over sodium sulfate. After the solvent was distilled off, the residue was purified by silica gel column chromatography (hexane:EtOAc=4:1 to 2:1) to obtain 58 mg of ethyl 1-{3-chloro-5-[(4-(4-chlorothiophen-2-yl)-5-{[cyclobutyl(methyl)amino]methyl}thiazol-2-yl)carbamoyl]-2-pyridyl}piperidine-4-carboxylate.

TABLE 15

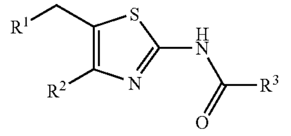

| Rf | $R^1$ | $R^2$ | $R^3$ | Data |
|---|---|---|---|---|
| 52 | H | 4-Cl-2-The | 5-Cl-6-($MeO_2C(CH_2)_2N(Me)$)-3-Py | MN; 471. |
| 53 | H | 4-Cl-2-The | 5-Cl-6-($MeO_2C(CH_2)_3N(Me)$)-3-Py | MN; 483. |
| 54 | H | 4-Cl-2-The | 5-F-6-(4-$EtO_2C$-pipe)-3-Py | MS; 495. |
| 55 | H | 4-Cl-2-The | 3-$F_3C$-4-Me-Ph | MS; 403. |
| 56 | H | 4-Me-2-The | 5,6-diCl-3-Py | MS; 370. |
| 57 | iPrN(Me)— | 4-Cl-2-The | 5,6-diCl-3-Py | MS; 475, 477. |
| 58 | iBuN(Me)— | 4-Cl-2-The | 5,6-diCl-3-Py | MS; 491. |
| 59 | 2-Me-pyrr— | 4-Cl-2-The | 5,6-diCl-3-Py | MS; 487. |
| 60 | (S)-2-Me-pyrr— | 4-Cl-2-The | 5,6-diCl-3-Py | MS; 487. |
| 61 | (R)-2-Me-pyrr— | 4-Cl-2-The | 5,6-diCl-3-Py | MS; 487. |
| 62 | iBuN(Me)— | 4-Me-2-The | 5,6-diCl-3-Py | MS; 469. |
| 63 | $cBuCH_2N(Me)$— | 4-Me-2-The | 5,6-diCl-3-Py | MS; 481. |
| 64 | 2-Me-pyrr— | 4-Me-2-The | 5,6-diCl-3-Py | MS; 467. |

EXAMPLE 1

3 ml of acetic acid, 24 µl of a formaldehyde aqueous solution (36%) and 47 µl of N-butyl-N-methylamine were added to 150 mg of ethyl 1-(3-chloro-5-{[4-(4-chlorothiophen-2-yl)thiazol-2-yl]carbamoyl}-2-pyridyl)piperidine-4-carboxylate, and the mixture was stirred at 90° C. for 18 hours. After the solvent was distilled off under reduced pressure, a saturated sodium hydrogencarbonate aqueous solution was added. The mixture was extracted with chloroform, and dried over magnesium sulfate. The solvent was distilled off under reduced pressure, and the resulting residue was purified by silica gel column chromatography using hexane:EtOAc (7:1 to 5:1) as an elution solvent to obtain 147 mg of ethyl 1-(5-{[5-{[butyl(methyl)amino]methyl}-4-(4-chlorothiophen-2-yl)thiazol-2-yl]carbamoyl}-3-chloro-2-pyridyl)piperidine-4-carboxylate.

EXAMPLE 2

39 µl of N-(2-methoxyethyl)methylamine, 51 µl of triethylamine and 23 mg of 4-(dimethylamino)pyridine were added to a 6 ml EtOH suspension of 107 mg of ethyl 1-(5-{[5-[(acetoxy)methyl]-4-(4-chlorothiophen-2-yl)thiazol-2-yl]carbamoyl}-3-chloro-2-pyridyl)piperidine-4-carboxylate, and the mixture was stirred at 50° C. for 2 hours. After the solvent was distilled off, a saturated sodium hydrogencarbonate aqueous solution was added, and the mixture was extracted with EtOAc, and washed with water and with brine(saturated sodium chloride aqueous solution). The resulting product was dried over magnesium sulfate, and the solvent was then distilled off under reduced pressure. The resulting residue was purified by silica gel column chromatography using a hexane:EtOAc (10:1 to 3.5:1) as an elution solvent to obtain 90 mg of ethyl 1-{3-chloro-5-[(4-(4-chlorothiophen-2-yl)-5-{[(2-methoxyethyl)(methyl)

EXAMPLE 4

1.3 ml of ethyl isonipecotate was added to a 5 ml THF solution of 413 mg of 5,6-dichloro-N-[4-(4-chlorothiophen-2-yl)-5-(piperidin-1-ylmethyl)-1,3-thiazol-2-yl]nicotinamide, and the mixture was stirred for 5 days. After the solvent was distilled off under reduced pressure, a saturated sodium hydrogencarbonate aqueous solution was added, and the resulting precipitate was collected by filtration. The precipitate was dissolved in chloroform, and a saturated sodium hydrogencarbonate aqueous solution was added. The mixture was extracted with chloroform, and dried over magnesium sulfate. The solvent was distilled off under reduced pressure, and the resulting residue was purified by silica gel column chromatography using hexane:EtOAc (4:1 to 3:1) as an elution solvent to obtain 468 mg of ethyl 1-(3-chloro-5-{[4-(4-chlorothiophen-2-yl)-5-(piperidinomethyl)thiazol-2-yl]carbamoyl}-2-pyridyl)piperidine-4-carboxylate.

EXAMPLE 5

0.4 ml of a 1M sodium hydroxide aqueous solution was added to a 1.5 ml EtOH suspension of 76 mg of ethyl 1-{3-chloro-5-[(4-(4-chlorothiophen-2-yl)-5-{[(2-methoxyethyl)(methyl)amino]methyl}thiazol-2-yl)carbamoyl]-2-pyridyl}piperidine-4-carboxylate, and the mixture was stirred at 60° C. for 2 hours. 0.6 ml of 1M hydrochloric acid and 0.5 ml of water were added at room temperature, and the resulting precipitate was collected by filtration, washed with 50% ethanol water, and dried under reduced pressure to obtain 73 mg of 1-{3-chloro-5-[(4-(4-chlorothiophen-2-yl)-5-{[(2-methoxyethyl)(methyl)amino]methyl}thiazol-2-yl)carbamoyl]-2-pyridyl}piperidine-4-carboxylic acid hydrochloride.

EXAMPLE 6

19 mg of sodium boron hydride was added to a 5 ml THF solution of 128 mg of ethyl [4-(5-{5-{[butyl(methyl)amino]methyl}-4-(4-chlorothiophen-2-yl)thiazol-2-yl]carbamoyl}-3-chloro-2-pyridyl)-2-oxopiperazin-1-yl]acetate, and the mixture was refluxed with stirring. A solution of 128 mg of MeOH in 2 ml of THF was slowly added thereto dropwise, and the mixture was stirred under reflux for 1 hour. The reaction solution was ice-cooled, and water was then added. The solution was extracted with chloroform, washed with brine, and then dried over magnesium sulfate. The solvent was distilled off under reduced pressure, and the resulting residue was purified by silica gel column chromatography using chloroform:MeOH (99:1 to 98:2) as an elution solvent. The resulting crude product was suspended in methanol, and insoluble matters were removed by filtration. Then, the solvent was distilled off under reduced pressure. The thus-obtained residue was dissolved in EtOAc, and a 4M HCl-EtOAc solution was added, followed by stirring. The resulting precipitate was then collected by filtration, and dried under reduced pressure to obtain 15 mg of N-[5-{[butyl(methyl)amino]methyl}-4-(4-chlorothiophen-2-yl)thiazol-2-yl]-5-chloro-6-[4-(2-hydroxyethyl)-3-oxopiperazin-1-yl]nicotinamide hydrochloride.

EXAMPLE 7

40 mg of the compound in Example 132 was dissolved in 6 ml of MeOH, and 1.6 ml of conc. hydrochloric acid was added, followed by stirring for 2 hours. Then, concentration was conducted, and the precipitate was filtered, and washed with EtOAc to obtain 32 mg of N-[5-{[butyl(methyl)amino]methyl}-4-(4-chlorothiophen-2-yl)thiazol-2-yl]-4-(2-hydroxymethoxy)-3-methoxybenzamide hydrochloride.

EXAMPLE 8

30 μl of triethylamine, 30 μl of morpholine, 45 mg of WSC.HCl and 30 mg of HOBt were added to 2 ml of a THF solution of 52 mg of 1-{3-chloro-5-[(4-(4-chlorothiophen-2-yl)-5-{[(3-methoxypropyl)(methyl)amino]methyl}thiazol-2-yl)carbamoyl]-2-pyridyl}piperidine-4-carboxylic acid hydrochloride, and the mixture was stirred overnight at room temperature. Chloroform was added to the reaction solution. The organic layer was washed with a saturated sodium hydrogencarbonate aqueous solution, with water and with brine, and then dried over sodium sulfate. After the solvent was distilled off, the residue was purified by silica gel column chromatography (eluent: chloroform:MeOH=100:1 to 50:1, hexane:EtOAc=2:1, then chloroform:MeOH=20:1), and suspended in 2 ml of diethyl ether. 2 ml of 4M HCl-EtOAc was added, and the precipitate was collected by filtration to obtain 25 mg of 5-chloro-N-(4-(4-chlorothiophen-2-yl)-5-{[(3-methoxypropyl)(methyl)amino]methyl}thiazol-2-yl)-6-[4-(morpholinocarbonyl)piperidino]nicotinamide hydrochloride.

EXAMPLE 9

3 ml of a 4M HCl-dioxane solution was added to 188 mg of the compound in Example 190, and the mixture was stirred at 50° C. for 18 hours. The reaction solution was cooled at room temperature, and the solid precipitated was then filtered to obtain 160 mg of [(1-{3-chloro-5-[(4-(4-chlorothiophen-2-yl)-5-{[(2-methoxyethyl)(methyl)amino]methyl}thiazol-2-yl)carbamoyl]-2-pyridyl}-4-piperidyl)oxy]acetic acid hydrochloride.

EXAMPLE 10

200 mg of the compound in Reference Example 23 was dissolved in 5 ml of formic acid, and 37 μl of methoxyethylamine and 92 μl of a formaldehyde aqueous solution (35%) were added, followed by stirring at 70° C. for 15 hours. After the reaction solution was concentrated, chloroform was added, and the organic layer was washed with a saturated sodium hydrogencarbonate aqueous solution, with water and with brine, followed by drying over sodium sulfate. After the solvent was distilled off, the residue was purified by silica gel column chromatography (hexane:EtOAc=5:1 to 3:1) to obtain 110 mg of ethyl 1-{3-chloro-5-{[7-chloro-5-(2-methoxyethyl)-5,6-dihydro-4H-thiazolo[5,4-c]thieno[2,3-e]azepin-2-yl]carbamoyl}-2-pyridine}-4-carboxylate.

EXAMPLE 11

100 mg of 6-[(2-aminoethyl)amino]-N-[5-{[butyl(methyl)amino]methyl}-4-(4-chlorothiophen-2-yl)thiazol-2-yl]-5-chloronicotinamide trihydrochloride was suspended in 5 ml of THF, and 85 μl of triethylamine was added, followed by cooling to 0° C. 13 μl of methanesulfonyl chloride was added to the solution, and the mixture was stirred at room temperature for 2 hours. The reaction solution was poured into water, and extracted with chloroform. The organic layer was washed with water and with brine, and then dried over magnesium sulfate. After the solvent was distilled off, the residue was purified by silica gel column chromatography (chloroform:MeOH =10:1) to obtain 75 mg of N-[5-{[butyl(methyl)amino]methyl}-4-(4-chlorothiophen-2-yl)thiazol-2-yl]-5-chloro-6-({2-[(methylsulfonyl)amino]ethyl}amino)nicotinamide.

The structures and the physical data of the compounds in Examples are shown in Tables 16 to 26 below. Symbols in the tables have the following meanings (this applies to the following).

Ex: Example No. (When only a numeral is shown in column Ex., it is indicated that the compound in this Example No. is a free compound, and when a slash "/" and "HCl" are described next to a numeral, it is indicated that the compound in this Example No. was hydrochloride.)

Syn: Process (A numeral indicates that a compound was synthesized in the same manner as the compound in Example to which the numeral is allotted as Example No., using the corresponding starting material.)

R: Substituent in the general formula (nPr: normal propyl, cBu: cyclobutyl, cHex: cyclohexyl, MOM: methoxymethyl, Ac: acetyl, Ms: methanesulfonyl, THF: tetrahydrofuryl, THP: tetrahydropyranyl)

TABLE 16

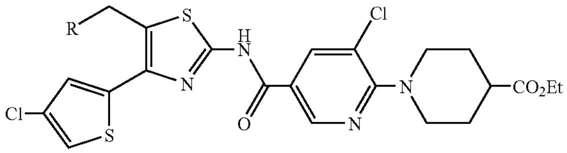

| Ex | Syn | R | Data |
|---|---|---|---|
| 1 | 1 | nBuN(Me)— | MS; 610. |
| 2 | 2 | $MeO(CH_2)_2N(Me)$— | MS; 612. |
| 3 | 3 | cBuN(Me)— | MS; 608. |
| 4 | 4 | pipe- | MS; 608. |
| 12 | 1 | $Me_2N$— | MS; 568. |
| 13 | 1 | pyrr- | MS; 594. |
| 14 | 1 | mor- | MS; 610. |
| 15 | 1 | 4-Me-pipa- | MS; 623. |
| 16 | 1 | 4-cHex-pipa- | MS; 691. |
| 17 | 1 | $Et_2N$— | MS; 650. |
| 18 | 1 | $EtO(CH_2)_2N(Me)$— | MS; 626. |
| 19 | 1 | $(2\text{-}THF)CH_2N(Me)$— | MS; 638. |
| 20 | 1 | $nPrO(CH_2)_2N(Me)$— | MS; 640. |
| 21 | 1 | $EtO(CH_2)_2N(Et)$— | MS; 640. |
| 22 | 1 | $iPrO(CH_2)_2N(Me)$— | MS; 640. |
| 23 | 1 | 4-(3-F-pyrr)pipe- | MS; 694. |
| 24 | 1 | $MeO(CH_2)_3N(Me)$— | MS; 625. |
| 25 | 1 | $MeO(CH_2)_2N(Et)$— | MS; 626 |
| 26 | 1 | (2S,6R)-2,6-diMe-mor- | MS; 638 |
| 27 | 1 | $4\text{-}EtO_2C$-pipe- | MN; 678. |
| 28 | 1 | iPrN(Me)— | MS; 596. |
| 29 | 1 | 2-Me-pyrr- | MS; 608. |
| 30 | 1 | (S)-2-Me-pyrr- | MS; 608. |
| 31 | 1 | (R)-2-Me-pyrr- | MS; 608. |
| 32 | 1 | (R)-3-Me-pyrr- | MS; 608. |
| 33 | 1 | (S)-3-Me-pyrr- | MS; 608. |
| 34 | 1 | 3-EtO-pyrr- | MS; 638. |
| 35 | 1 | 4-MeO-pipe- | MS; 638. |
| 36 | 1 | 3-MeO-pipe- | MS; 638. |
| 37 | 1 | $(S)\text{-}2\text{-}MeOCH_2$-pyrr- | MS; 638. |
| 38 | 1 | $(R)\text{-}2\text{-}MeOCH_2$-pyrr- | MS; 638. |
| 39 | 2 | $(R)\text{-}MeOCH_2CH(Me)N(Me)$ | MS; 626. |
| 40 | 2 | $(S)\text{-}MeOCH_2CH(Me)N(Me)$ | MS; 626. |
| 41 | 2 | azet- | MS; 580. |
| 42 | 2 | Azepan-1-yl | MS; 622. |
| 43 | 2 | Azocan-1-yl | MS; 636. |
| 44 | 2 | Azonan-1-yl | MS; 650. |
| 45 | 2 | Azecan-1-yl | MS; 664. |
| 46 | 2 | (2R,6S)-2,6-diMe-pipe | MS; 636. |
| 47 | 2 | $Me_2N(CH_2)_2N(Me)$— | MS; 625. |
| 48 | 2 | cHexN(Me)— | MS; 636. |
| 49 | 2 | $MeO(CH_2)_2NH$— | MS; 597. |
| 50 | 2 | cPrNH— | MS; 580. |
| 51 | 2 | cBuNH— | MS; 594. |
| 52 | 2 | cHexNH— | MS; 622. |
| 53 | 2 | iPrNH— | MS; 582. |
| 54 | 2 | tBuNH— | MS; 596. |
| 55 | 2 | (4-THP)NH— | MS; 624. |
| 56 | 2 | (3-THF)NH— | MS; 610. |
| 57 | 2 | $MeOCH_2CH(Me)NH$— | MS; 612. |
| 58 | 3 | (4-THP)N(Me)— | MS; 638. |
| 59 | 3 | (3-THF)N(Me)— | MS; 624. |
| 60 | 3 | $MeOCH_2CH(Me)N(Me)$— | MS; 626. |
| 61 | 3 | cPrN(Me)— | MS; 594. |
| 62 | 3 | iBuN(Me)— | MS; 610. |
| 63 | 10 | $(R)\text{-}(MeO)(Me)CHCH_2N(Me)$— | MS; 626. |
| 64 | 10 | $(S)\text{-}(MeO)(Me)CHCH_2N(Me)$— | MS; 626. |

TABLE 17

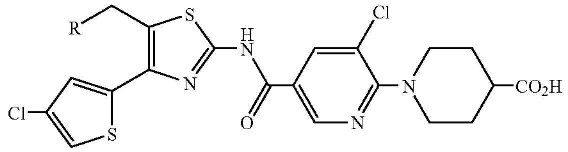

| Ex | Syn | R | Data |
|---|---|---|---|
| 5/HCl | 5 | $MeO(CH_2)_2N(Me)$— | MS; 584. |
| 65/HCl | 5 | $Me_2N$— | MS; 540. |
| 66/HCl | 5 | pyrr- | MS; 566. |
| 67/HCl | 5 | mor- | MN; 580. |
| 68/HCl | 5 | 4-Me-pipa- | MS; 595. |
| 69/HCl | 5 | 4-cHex-pipa- | MS; 663. |
| 70/HCl | 5 | $Et_2N$— | MS; 568. |
| 71/HCl | 5 | nBuN(Me)— | MS; 582. |
| 72/HCl | 5 | $EtO(CH_2)_2N(Me)$— | MS; 598. |
| 73/HCl | 5 | $(2\text{-}THF)CH_2N(Me)$— | MS; 610. |
| 74/HCl | 5 | $nPrO(CH_2)_2N(Me)$— | MS; 612. |
| 75/HCl | 5 | $EtO(CH_2)_2N(Et)$— | MS; 612. |
| 76/HCl | 5 | $iPrO(CH_2)_2N(Me)$— | MS; 612. |
| 77/HCl | 5 | 4-(3-F-pyrr)pipe- | MS; 667. |
| 78/HCl | 5 | $MeO(CH_2)_3N(Me)$— | MN; 596. |
| 79/HCl | 5 | $MeO(CH_2)_2N(Et)$— | MS; 598. |
| 80 | 5 | (2S,6R)-2,6-diMe-mor- | MN; 608. |
| 81/HCl | 5 | $(R)\text{-}MeOCH_2CH(Me)N(Me)$— | MS; 598. |
| 82/HCl | 5 | $(S)\text{-}MeOCH_2CH(Me)N(Me)$— | MS; 598. |
| 83/HCl | 5 | azet- | MS; 552. |
| 84/HCl | 5 | Azepan-1-yl | MS; 594. |
| 85/HCl | 5 | Azocan-1-yl | MS; 608. |
| 86/HCl | 5 | Azonan-1-yl | MS; 622. |
| 87/HCl | 5 | Azecan-1-yl | MS; 636. |
| 88/HCl | 5 | (2R,6S)-2,6-diMe-pipe- | MS; 608. |
| 89/HCl | 5 | $Me_2N(CH_2)_2N(Me)$— | MS; 597. |
| 90/HCl | 5 | cHexN(Me)— | MS; 608. |
| 91/HCl | 5 | $MeO(CH_2)_2NH$— | MS; 569. |
| 92/HCl | 5 | cPrNH— | MN; 550. |
| 93/HCl | 5 | cBuNH— | MN; 564. |
| 94/HCl | 5 | cHex-NH— | MN; 592. |
| 95/HCl | 5 | iPrNH— | MN; 552. |
| 96/HCl | 5 | tBuNH— | MN; 566. |
| 97/HCl | 5 | (4-THP)N(Me)— | MS; 610. |
| 98/HCl | 5 | (3-THF)N(Me)— | MS; 596. |
| 99/HCl | 5 | $MeOCH_2CH(Me)N(Me)$— | MS; 598. |
| 100/HCl | 5 | cBuN(Me)— | MS; 580. |
| 101/HCl | 5 | cPrN(Me)— | MS; 566. |
| 102/HCl | 5 | pipe- | MN; 578. |
| 103/HCl | 5 | iBuN(Me)— | MS; 582. |
| 104/HCl | 5 | iPrN(Me)— | MS; 568. |
| 105/HCl | 5 | 2-Me-pyrr- | MS; 580. |
| 106/HCl | 5 | (S)-2-Me-pyrr- | MS; 580. |
| 107/HCl | 5 | (R)-2-Me-pyrr- | MS; 580. |
| 108/HCl | 5 | (R)-3-Me-pyrr- | MS; 580. |
| 109/HCl | 5 | (S)-3-Me-pyrr- | MS; 580. |
| 110/HCl | 5 | $(R)\text{-}MeOCH(Me)CH_2N(Me)$— | MS; 598. |
| 111/HCl | 5 | $(S)\text{-}MeOCH(Me)CH_2N(Me)$— | MS; 598. |
| 112/HCl | 5 | 3-EtO-pyrr- | MS; 610. |
| 113/HCl | 5 | 4-MeO-pipe- | MS; 610. |
| 114/HCl | 5 | 3-MeO-pipe- | MS; 610. |
| 115/HCl | 5 | $(S)\text{-}2\text{-}MeOCH_2$-pyrr- | MS; 610. |
| 116/HCl | 5 | $(R)\text{-}2\text{-}MeOCH_2$-pyrr- | MS; 610. |

TABLE 18

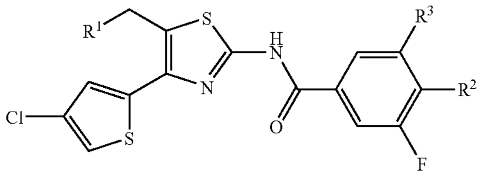

| Ex | Syn | $R^1$ | $R^2$ | $R^3$ | Data |
|---|---|---|---|---|---|
| 117 | 1 | $MeO(CH_2)_2N(Me)$— | 4-$(EtO_2CCH_2)$pipa— | Cl | MS; 644. |
| 118 | 1 | nBuN(Me)— | 4-$(EtO_2CCH_2)$pipa— | Cl | MS; 642. |
| 119/HCl | 1 | nBuN(Me)— | $HO(CH_2)_3O$— | Cl | MS; 546. |
| 120/HCl | 1 | nBuN(Me)— | $AcO(CH_2)_3O$— | Cl | MS; 588. |
| 121 | 1 | iBuN(Me)— | $MeO_2C(CH_2)_3O$— | H | MM: 554. |
| 122 | 2 | Azocan-1-yl | 4-$EtO_2C$-pipe | F | MS; 637. |
| 123 | 2 | nBuN(Me)— | 4-$EtO_2C$-pipe | F | MS; 611. |
| 124/HCl | 5 | $MeO(CH_2)_2N(Me)$— | 4-$(HO_2CCH_2)$pipa— | Cl | MN; 614. |
| 125/HCl | 5 | nBuN(Me)— | 4-$(HO_2CCH_2)$pipa— | Cl | MS; 614. |
| 126/HCl | 5 | Azocan-1-yl | 4-$HO_2C$-pipe | F | MS; 609. |
| 127/HCl | 5 | nBuN(Me)— | 4-$HO_2C$-pipe | F | MS; 583. |
| 128/HCl | 5 | iBuN(Me)— | $HO_2C(CH_2)_3O$— | H | MN; 538. |

TABLE 19

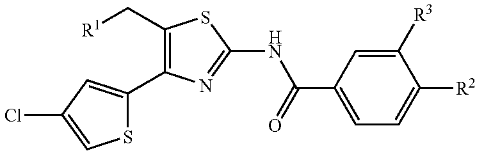

| Ex | Syn | $R^1$ | $R^2$ | $R^3$ | Data |
|---|---|---|---|---|---|
| 7/HCl | 7 | nBuN(Me)— | $HO(CH_2)_2O$— | OMe | MS; 510 |
| 129 | 1 | nBuN(Me)— | OMOM | Cl | MS; 514. |
| 130/HCl | 1 | nBuN(Me)— | OH | Cl | MS; 470. |
| 131 | 1 | nBuN(Me)— | $MeO_2C(CH_2)_3O$— | F | MS; 554. |
| 132 | 1 | nBuN(Me)— | $TBSO(CH_2)_2O$— | OMe | MS; 624. |
| 133 | 1 | nBuN(Me)— | Me | $CF_3$ | MS; 502. |
| 134/HCl | 5 | nBuN(Me)— | $HO_2C(CH_2)_3O$— | F | MS; 540. |

TABLE 20

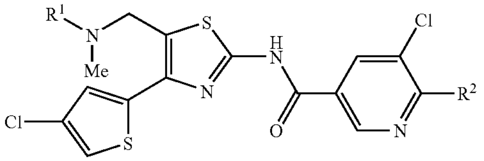

| Ex | Syn | $R^1$ | $R^2$ | Data |
|---|---|---|---|---|
| 6/HCl | 6 | nBu | 3-oxo-4-$HO(CH_2)_2$-pipa— | MS; 597. |
| 11/HCl | 11 | nBu | $MsHN(CH_2)_2NH$— | MS; 591. |
| 135 | 1 | nBu | 3-$MeO_2C$-pyrr | MS; 582. |
| 136 | 1 | nBu | (R)-3-$(MeO_2CCH_2O)$pyrr- | MS; 612. |
| 137 | 1 | nBu | (S)-3-$MeO_2C$-pyrr- | MS; 582. |
| 138 | 1 | nBu | 3-$EtO_2C$-azet- | MS; 582. |
| 139 | 1 | nBu | 4-$(tBuO_2CCH_2O)$pipe- | MS; 668. |
| 140 | 1 | nBu | 2-$EtO_2C$-mor- | MS; 612. |
| 141 | 1 | nBu | 4-$(MeO_2CCH_2NHCO)$pipe- | MS; 653. |
| 142 | 3 | nBu | 4-OH-4-$EtO_2C$-pipe- | MS; 626. |
| 143 | 3 | nBu | $tBuO_2C(CH_2)_2NH$— | MS; 598. |
| 144 | 3 | iBu | 3-$(EtO_2CCH_2)$azet- | MS; 596. |
| 145 | 3 | iBu | $EtO_2C(CH_2)_3NH$— | MS; 584. |

TABLE 20-continued

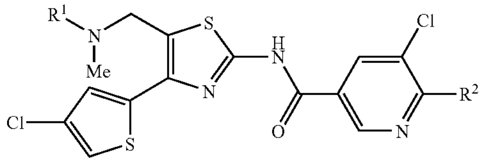

| Ex | Syn | $R^1$ | $R^2$ | Data |
|---|---|---|---|---|
| 146 | 3 | iBu | $tBuO_2C(CH_2)_2NH$— | MS; 598. |
| 147 | 3 | iBu | $MeO_2C(CH_2)_3N(Me)$— | MS; 584. |
| 148 | 3 | iBu | $EtO_2C(CH_2)_2N(Me)$— | MS; 584. |
| 149 | 3 | iBu | $EtO_2CCH_2N(Me)$— | MS; 570. |
| 150/HCl | 4 | nBu | 4-$HOCH_2$-pipe- | MS; 568. |
| 151/HCl | 4 | nBu | $HO(CH_2)_3NH$— | MS; 528. |
| 152/HCl | 4 | nBu | $MeO(CH_2)_2O(CH_2)_2NH$— | MS; 572. |
| 153/HCl | 4 | nBu | 3-oxo-pipa- | MS; 553. |
| 154/HCl | 4 | nBu | $H_2N(CH_2)_2NH$— | MS; 513. |
| 155 | 4 | nBu | 4-(4-$MeO_2C$-pipe)-pipe- | MS; 679. |
| 156 | 4 | nBu | 3-oxo-4-$EtO_2CCH_2$-pipa- | MS; 639. |
| 157 | 4 | nBu | $EtO_2C(CH_2)_3NH$— | MS; 584. |
| 158/HCl | 5 | nBu | $HO_2C(CH_2)_3NH$— | MS; 556. |
| 159/HCl | 5 | nBu | 4-(4-$HO_2C$-pipe)-pipe- | MN; 663. |
| 160/HCl | 5 | nBu | 3-oxo-4-$HO_2CCH_2$-pipa- | MS; 611. |
| 161/HCl | 5 | nBu | 3-$HO_2C$-pyrr- | MS; 568. |
| 162/HCl | 5 | nBu | (R)-3-($HO_2CCH_2O$)-pyrr- | MN; 596. |
| 163/HCl | 5 | nBu | (S)-3-$HO_2C$-pyrr- | MS; 568. |
| 164/HCl | 5 | nBu | 3-$HO_2C$-azet- | MS; 554. |
| 165/HCl | 5 | nBu | 2-$HO_2C$-mor- | MS; 584. |
| 166/HCl | 5 | nBu | 4-(3-$HO_2C$-azet-CO)pipe- | MN; 663. |
| 167/HCl | 5 | nBu | 4-($HO_2C(CH_2)_2NHCO$)pipe- | MS; 653. |
| 168/HCl | 5 | nBu | 4-($HO_2CCH_2NHCO$)pipe- | MS; 639. |
| 169/HCl | 5 | nBu | 4-HO-4-$HO_2C$-pipe- | MS; 598. |
| 170/HCl | 5 | iBu | 3-($HO_2CCH_2$)azet- | MS; 568. |
| 171/HCl | 5 | iBu | $HO_2C(CH_2)_3NH$— | MS; 556. |
| 172/HCl | 5 | iBu | $HO_2C(CH_2)_3N(Me)$— | MS; 570. |
| 173/HCl | 5 | iBu | $HO_2C(CH_2)_2N(Me)$— | MS; 556. |
| 174/HCl | 5 | iBu | $HO_2CCH_2N(Me)$— | MS; 542. |
| 175 | 8 | nBu | 4-(3-$EtO_2C$-azet-CO)pipe | MS; 693. |
| 176/HCl | 8 | nBu | 4-($MeO(CH_2)_2NHCO$)pipe | MS; 639. |
| 177/HCl | 8 | nBu | 4-($H_2NCOCH_2NHCO$)pipe | MS; 638. |
| 178/HCl | 8 | nBu | 4-($MeO(CH_2)_2O(CH_2)_2NHCO$)pipe- | MS; 683. |
| 179 | 8 | nBu | 4-($EtO_2C(CH_2)_2NHCO$)pipe- | MS; 681. |
| 180 | 8 | nBu | 4-($HO(CH_2)_2NHCO$)pipe- | MS; 625. |
| 181/HCl | 9 | nBu | 4-$HO_2CCH_2O$-pipe- | MS; 612. |
| 182/HCl | 9 | nBu | $HO_2C(CH_2)_2NH$— | MS; 542. |
| 183/HCl | 9 | iBu | $HO_2C(CH_2)_2NH$— | MS; 542. |

TABLE 21

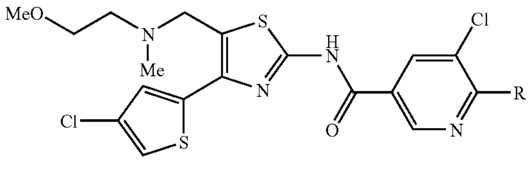

| Ex | Syn | R | Data |
|---|---|---|---|
| 9/HCl | 9 | 4-($HO_2CCH_2O$)pipe- | MN; 612. |
| 184 | 1 | 3-$EtO_2C$-pipe- | MS; 612. |
| 185 | 1 | 3-$MeO_2C$-pyrr- | MS; 584. |
| 186 | 1 | (R)-3-($MeO_2CCH_2O$)pyrr- | MS; 614. |
| 187 | 1 | 4-$EtO_2CCH_2$-pipe- | MS; 626. |
| 188 | 1 | 2-$EtO_2C$-mor- | MN; 612. |
| 189 | 1 | 3-$EtO_2C$-azet- | MS; 584. |
| 190 | 1 | 4-($tBuO_2CCH_2O$)-pipe- | MS; 670. |
| 191/HCl | 5 | 3-$HO_2C$-pipe- | MS; 584. |

TABLE 21-continued

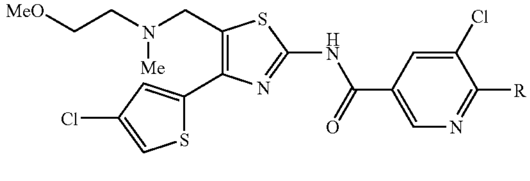

| Ex | Syn | R | Data |
|---|---|---|---|
| 192/HCl | 5 | 3-$HO_2C$-pyrr | MS; 570. |
| 193/HCl | 5 | (R)-3-($HO_2CCH_2O$)pyrr- | MS; 600. |
| 194/HCl | 5 | 4-$HO_2CCH_2$-pipe- | MS; 598. |
| 195/HCl | 5 | 2-$HO_2C$-mor- | MS; 586. |
| 196/HCl | 5 | 3-$HO_2C$-azet- | MS; 556. |

TABLE 22

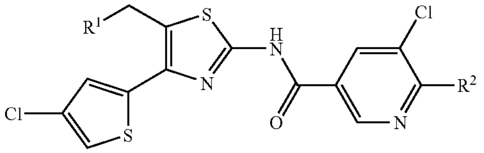

| Ex | Syn | $R^1$ | $R^2$ | Data |
|---|---|---|---|---|
| 8/HCl | 8 | $MeO(CH_2)_3N(Me)$— | 4-(mor-CO)pipe- | MS; 667. |
| 197 | 8 | $MeO(CH_2)_3N(Me)$— | 4-($MeO(CH_2)_2NHCO$)pipe- | MS; 655. |
| 198 | 1 | $Me_2N$— | 3-$MeO_2C$-pyrr- | MN; 538. |
| 199 | 1 | (S)-2-Me-pyrr- | $MeO_2C(CH_2)_3N(Me)$— | MS; 582. |
| 200 | 1 | (R)-2-Me-pyrr- | $MeO_2C(CH_2)_3N(Me)$— | MS; 582. |
| 201 | 1 | $Et_2CHN(Me)$— | $MeO_2C(CH_2)_3N(Me)$— | MS; 598. |
| 202 | 1 | (S)-3-Me-pyrr- | $MeO_2C(CH_2)_3N(Me)$— | MS; 582. |
| 203 | 1 | 2-Me-pyrr- | $MeO_2C(CH_2)_2N(Me)$— | MS; 568. |
| 204 | 1 | iPrN(Me)— | $MeO_2C(CH_2)_2N(Me)$— | MS; 556. |
| 205 | 1 | (nPr)(Me)CHN(Me)— | $MeO_2C(CH_2)_2N(Me)$— | MS; 584. |
| 206 | 1 | (S)-3-Me-pyrr- | $MeO_2C(CH_2)_2N(Me)$— | MS; 568. |
| 207 | 1 | iPrN(Me)— | (S)-$MeO_2C$-pyrr- | MS; 568. |
| 208 | 3 | 2-Me-pyrr- | 3-($EtO_2CCH_2$)azet- | MS; 594. |
| 209 | 3 | (S)-2-Me-pyrr- | 3-($EtO_2CCH_2$)azet- | MS; 594. |
| 210 | 3 | (R)-2-Me-pyrr- | 3-($EtO_2CCH_2$)azet- | MS; 594. |
| 211 | 3 | iPrN(Me)— | 3-($EtO_2CCH_2$)azet- | MS; 582. |
| 212 | 3 | 2-Me-pyrr- | $MeO_2C(CH_2)_3N(Me)$— | MS; 582. |
| 213 | 3 | iPrN(Me)— | $MeO_2C(CH_2)_3N(Me)$— | MS; 570. |
| 214 | 3 | 2-Me-pyrr- | $EtO_2C(CH_2)_3NH$— | MS; 582. |
| 215 | 3 | (S)-2-Me-pyrr- | $EtO_2C(CH_2)_3NH$— | MS; 582. |
| 216 | 3 | (R)-2-Me-pyrr- | $EtO_2C(CH_2)_3NH$— | MS; 582. |
| 217 | 3 | 2-Me-pyrr- | $tBuO_2C(CH_2)_2NH$— | MS; 596. |
| 218/HCl | 4 | pipe- | 4-$H_2NOC$-pipe- | MN; 579. |
| 219/HCl | 5 | $Me_2N$— | 3-$HO_2C$-pyrr- | MS; 526. |
| 220/HCl | 5 | 2-Me-pyrr- | 3-($HO_2CCH_2$)azet- | MN; 564. |
| 221/HCl | 5 | (S)-2-Me-pyrr- | 3-($HO_2CCH_2$)azet- | MN; 564. |
| 222/HCl | 5 | (R)-2-Me-pyrr- | 3-($HO_2CCH_2$)azet- | MN; 564. |
| 223/HCl | 5 | iPrN(Me)— | 3-($HO_2CCH_2$)azet- | MN; 552. |
| 224/HCl | 5 | 2-Me-pyrr- | $HO_2C(CH_2)_3N(Me)$— | MS; 568. |
| 225/HCl | 5 | (S)-2-Me-pyrr- | $HO_2C(CH_2)_3N(Me)$— | MS; 568. |
| 226/HCl | 5 | (R)-2-Me-pyrr- | $HO_2C(CH_2)_3N(Me)$— | MS; 568. |
| 227/HCl | 5 | iPrN(Me)— | $HO_2C(CH_2)_3N(Me)$— | MS; 556. |
| 228/HCl | 5 | $Et_2CHN(Me)$— | $HO_2C(CH_2)_3N(Me)$— | MS; 584. |
| 229/HCl | 5 | (S)-3-Me-pyrr- | $HO_2C(CH_2)_3N(Me)$— | MN; 566. |
| 230/HCl | 5 | 2-Me-pyrr- | $HO_2C(CH_2)_2N(Me)$— | MS; 554. |
| 231/HCl | 5 | iPrN(Me)— | $HO_2C(CH_2)_2N(Me)$— | MN; 540. |
| 232/HCl | 5 | (nPr)(Me)CHN(Me)— | $HO_2C(CH_2)_2N(Me)$— | MS; 570. |
| 233/HCl | 5 | (S)-3-Me-pyrr- | $HO_2C(CH_2)_2N(Me)$— | MS; 554. |
| 234/HCl | 5 | 2-Me-pyrr- | $HO_2C(CH_2)_3NH$— | MS; 554. |
| 235/HCl | 5 | (S)-2-Me-pyrr- | $HO_2C(CH_2)_3NH$— | MN; 552. |
| 236/HCl | 5 | (R)-2-Me-pyrr- | $HO_2C(CH_2)_3NH$— | MN; 552. |
| 237/HCl | 5 | iPrN(Me)— | (S)-3-$HO_2C$-pyrr- | MN; 552. |
| 238/HCl | 9 | 2-Me-pyrr- | $HO_2C(CH_2)_2NH$— | MN; 538. |

TABLE 23

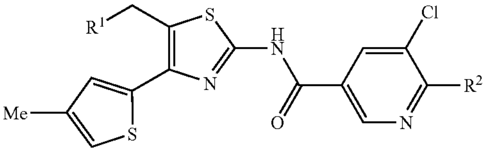

| Ex | Syn | $R^1$ | $R^2$ | Data |
|---|---|---|---|---|
| 239 | 1 | nBuN(Me)— | 4-$EtO_2C$-pipe- | MN; 588. |
| 240 | 1 | $Me_2N$— | 4-$EtO_2C$-pipe- | MS; 588. |
| 241 | 1 | iBuN(Me)— | 4-$EtO_2C$-pipe- | MN; 588. |
| 242 | 1 | cHexN(Me)— | 4-$EtO_2C$-pipe- | MS; 588. |
| 243 | 1 | iPrN(Me)— | 4-$EtO_2C$-pipe- | MN; 588. |
| 244 | 1 | cBuN(Me)— | 4-$EtO_2C$-pipe- | MN; 687. |
| 245 | 1 | $Et_2CHN(Me)$— | 4-$EtO_2C$-pipe- | MN; 687. |
| 246 | 1 | (nPr)(Me)CHN(Me)— | 4-$EtO_2C$-pipe- | MS; 604. |
| 247 | 1 | (iPr)(Me)CHN(Me)— | 4-$EtO_2C$-pipe- | MS; 604. |
| 248 | 1 | tBuN(Me)— | 4-$EtO_2C$-pipe- | MS; 590. |

TABLE 23-continued

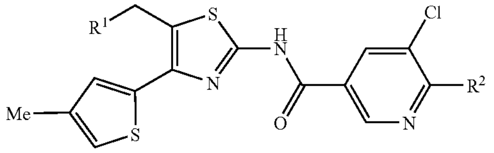

| Ex | Syn | $R^1$ | $R^2$ | Data |
|---|---|---|---|---|
| 249 | 1 | $cBuCH_2N(Me)$— | 4-$EtO_2C$-pipe- | MS; 602. |
| 250 | 1 | Azepan-1-yl | 4-$EtO_2C$-pipe- | MS; 602. |
| 251 | 1 | 4-Me-pipe- | 4-$EtO_2C$-pipe- | MS; 602. |
| 252 | 1 | 3-Me-pipe- | 4-$EtO_2C$-pipe- | MS; 602. |
| 253 | 1 | 2-Me-pipe- | 4-$EtO_2C$-pipe- | MS; 602. |
| 254 | 1 | 2-Me-pyrr- | 4-$EtO_2C$-pipe- | MS; 588. |
| 255 | 1 | (S)-2-Me-pyrr- | 4-$EtO_2C$-pipe- | MS; 588. |
| 256 | 1 | (R)-2-Me-pyrr- | 4-$EtO_2C$-pipe- | MS; 588. |
| 257 | 1 | (R)-3-Me-pyrr- | 4-$EtO_2C$-pipe- | MS; 588. |
| 258 | 1 | (S)-3-Me-pyrr- | 4-$EtO_2C$-pipe- | MS; 588. |
| 259 | 1 | 3,3-diMe-pyrr- | 4-$EtO_2C$-pipe- | MN; 600. |
| 260 | 3 | iBuN(Me)— | 4-HO-4-$EtO_2C$-pipe- | MS; 606. |
| 261 | 3 | iBuN(Me)— | $EtO_2C(CH_2)_3NH$— | MS; 564. |
| 262 | 3 | iBuN(Me)— | $MeO_2C(CH_2)_3N(Me)$— | MS; 564. |
| 263 | 3 | $cBuCH_2N(Me)$— | 4-HO-4-$EtO_2C$-pipe- | ESI-MS(Pos); 618. |
| 264 | 3 | 2-Me-pyrr- | 4-HO-4-$EtO_2C$-pipe- | MS; 604. |
| 265 | 3 | 2-Me-pyrr- | $EtO_2C(CH_2)_3NH$— | MS; 562. |
| 266 | 3 | 2-Me-pyrr- | $MeO_2C(CH_2)_3N(Me)$— | ESI-MS(Pos); 562. |
| 267/HCl | 5 | nBuN(Me)— | 4-$HO_2C$-pipe- | MS; 562. |
| 268/HCl | 5 | $Me_2N$— | 4-$HO_2C$-pipe- | MS; 520. |
| 269/HCl | 5 | iBuN(Me)— | 4-$HO_2C$-pipe- | MS; 562. |
| 270/HCl | 5 | cHexN(Me)— | 4-$HO_2C$-pipe- | MS; 588. |
| 271/HCl | 5 | iPrN(Me)— | 4-$HO_2C$-pipe- | MS; 548. |
| 272/HCl | 5 | cBuN(Me)— | 4-$HO_2C$-pipe- | MS; 560. |
| 273/HCl | 5 | $Et_2CHN(Me)$— | 4-$HO_2C$-pipe- | MS; 576. |
| 274/HCl | 5 | (nPr)(Me)CHN(Me)— | 4-$HO_2C$-pipe- | MS; 576. |
| 275/HCl | 5 | (iPr)(Me)CHN(Me)— | 4-$HO_2C$-pipe- | MS; 576. |
| 276/HCl | 5 | $cBuCH_2N(Me)$— | 4-$HO_2C$-pipe- | MS; 574. |
| 277/HCl | 5 | Azepan-1-yl | 4-$HO_2C$-pipe- | MS; 574. |
| 278/HCl | 5 | 4-Me-pipe- | 4-$HO_2C$-pipe- | MS; 574. |
| 279/HCl | 5 | 3-Me-pipe- | 4-$HO_2C$-pipe- | MS; 574. |
| 280/HCl | 5 | 2-Me-pipe- | 4-$HO_2C$-pipe- | MS; 574. |
| 281/HCl | 5 | 2-Me-pyrr- | 4-$HO_2C$-pipe- | MN; 558. |
| 282/HCl | 5 | (S)-2-Me-pyrr- | 4-$HO_2C$-pipe- | MS; 560. |
| 283/HCl | 5 | (R)-2-Me-pyrr- | 4-$HO_2C$-pipe- | MS; 560. |
| 284/HCl | 5 | (R)-3-Me-pyrr- | 4-$HO_2C$-pipe- | MN; 558. |
| 285/HCl | 5 | (S)-3-Me-pyrr- | 4-$HO_2C$-pipe- | MN; 558. |
| 286/HCl | 5 | 3,3-diMe-pyrr- | 4-$HO_2C$-pipe- | MS; 574. |
| 287/HCl | 5 | iBuN(Me)— | 4-HO-4-$HO_2C$-pipe- | MS; 578. |
| 288/HCl | 5 | iBuN(Me)— | $HO_2C(CH_2)_3NH$— | MS; 536. |
| 289/HCl | 5 | iBuN(Me)— | $HO_2C(CH_2)_3N(Me)$— | MS; 550. |
| 290/HCl | 5 | $cBuCH_2N(Me)$— | 4-HO-4-$HO_2C$-pipe- | MS; 590. |
| 291/HCl | 5 | 2-Me-pyrr- | 4-HO-4-$HO_2C$-pipe- | MS; 576. |
| 292/HCl | 5 | 2-Me-pyrr- | $HO_2C(CH_2)_3NH$— | MS; 534. |
| 293/HCl | 5 | 2-Me-pyrr- | $HO_2C(CH_2)_3N(Me)$— | MS; 548. |

TABLE 24

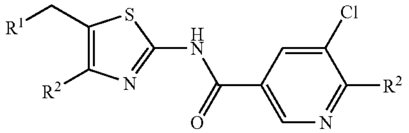

| Ex | Syn | $R^1$ | $R^2$ | $R^3$ | Data |
|---|---|---|---|---|---|
| 294 | 1 | pipe | 4-F—Ph— | 4-$EtO_2C$-pipe- | MS; 586. |
| 295 | 1 | pipe | 3-$F_3C$—Ph— | 4-$EtO_2C$-pipe- | MS; 636. |
| 296 | 1 | nBuN(Me)— | 4-F—Ph— | 4-$EtO_2C$-pipe- | MS; 588. |
| 297 | 1 | nBuN(Me)— | 4-Me-5-(nBuN(Me)$CH_2$)-2-The- | 4-$EtO_2C$-pipe- | MN; 687. |
| 298/HCl | 5 | pipe | 4-F—Ph— | 4-$HO_2C$-pipe- | MS; 558. |
| 299/HCl | 5 | pipe | 3-$F_3C$—Ph— | 4-$HO_2C$-pipe- | MS; 608. |
| 300/HCl | 5 | nBuN(Me)— | 4-F—Ph— | 4-$HO_2C$-pipe- | MS; 560. |

TABLE 25

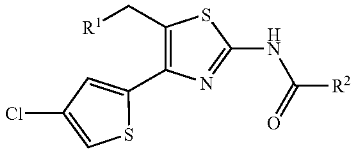

| Ex | Syn | $R^1$ | $R^2$ | Data |
|---|---|---|---|---|
| 301/HCl | 1 | pipe | 2-MeO-4-Py | MS; 449. |
| 302 | 1 | nBuN(Me)— | 4-(4-$MeO_2C$-pipe)pipe | MS; 568. |
| 303 | 1 | nBuN(Me)$CH_2$— | 5-Cl-6-(4-$EtO_2C$-pipe)-3-Py | MS; 624. |
| 304 | 1 | nPrN(Me)— | 5-F-6-(4-$EtO_2C$-pipe)-3-Py | MS; 580. |
| 305 | 1 | iBuN(Me)— | 5-F-6-(4-$EtO_2C$-pipe)-3-Py | MS; 594. |
| 306 | 1 | 2-Me-pyrr- | 5-F-6-(4-$EtO_2C$-pipe)-3-Py | MS; 592. |
| 307 | 1 | (S)-2-Me-pyrr- | 5-F-6-(4-$EtO_2C$-pipe)-3-Py | MS; 592. |
| 308 | 1 | (R)-2-Me-pyrr- | 5-F-6-(4-$EtO_2C$-pipe)-3-Py | MS; 592. |
| 309 | 1 | iPrN(Me)— | 5-F-6-(4-$EtO_2C$-pipe)-3-Py | MS; 580. |
| 310/HCl | 5 | nBuN(Me)$CH_2$— | 5-Cl-6-(4-$HO_2C$-pipe)-3-Py | MS; 596. |
| 311/HCl | 5 | nPrN(Me)— | 5-F-6-(4-$HO_2C$-pipe)-3-Py | MS; 552. |
| 312/HCl | 5 | iBuN(Me)— | 5-F-6-(4-$HO_2C$-pipe)-3-Py | MS; 566. |
| 313/HCl | 5 | 2-Me-pyrr- | 5-F-6-(4-$HO_2C$-pipe)-3-Py | MS; 564. |
| 314/HCl | 5 | (S)-2-Me-pyrr- | 5-F-6-(4-$HO_2C$-pipe)-3-Py | MN: 562. |
| 315/HCl | 5 | (R)-2-Me-pyrr- | 5-F-6-(4-$HO_2C$-pipe)-3-Py | MS; 564. |
| 316/HCl | 5 | iPrN(Me)— | 5-F-6-(4-$HO_2C$-pipe)-3-Py | MN: 550. |

TABLE 26

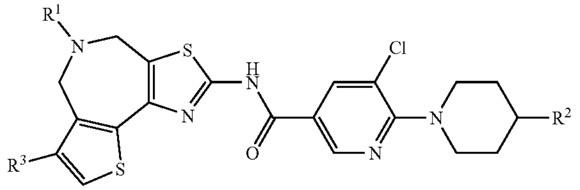

| Ex | Syn | $R^1$ | $R^2$ | $R^3$ | Data |
|---|---|---|---|---|---|
| 10 | 10 | $MeO(CH_2)_2$— | $EtO_2C$— | Cl | MS; 610. |
| 317/HCl | 5 | cBu | $HO_2C$— | Cl | MS; 578. |
| 318/HCl | 5 | $MeO(CH_2)_2$— | $HO_2C$— | Cl | MS; 582. |
| 319/HCl | 5 | (R)-(MeO)(Me)$CHCH_2$— | $HO_2C$— | Cl | MS; 596. |
| 320/HCl | 5 | (S)-(MeO)(Me)$CHCH_2$— | $HO_2C$— | Cl | MS; 596. |
| 321 | 5 | Me | $HO_2C$— | Cl | ESI-MS(Pos); 538. |
| 322/HCl | 5 | Me | $HO_2C$— | Me | MS; 518. |
| 323 | 10 | cBu | $EtO_2C$— | Cl | MS; 606. |
| 324 | 10 | (R)-(MeO)(Me)$CHCH_2$— | $EtO_2C$— | Cl | MS; 624. |
| 325 | 10 | (S)-(MeO)(Me)$CHCH_2$— | $EtO_2C$— | Cl | MS; 624. |
| 326 | 10 | Et | $EtO_2C$— | Cl | MN; 578. |
| 327 | 10 | Me | $EtO_2C$— | Cl | ESI-MS(Pos); 566. |
| 328 | 10 | Me | $EtO_2C$— | Me | MS; 546. |

NMR data of selected Example compounds are shown in Table 27 below. Each data shows peak δ (ppm) in $^1$H-NMR using tetramethylsilane as an internal standard and DMSO-$δ_6$ as a measuring solvent unless otherwise instructed.

TABLE 27

| Ex | Data |
|---|---|
| 5 | 1.62-1.74(2H, m), 1.90-1.98(2H, m), 2.52-2.58(1H, m), 2.81(3H, s), 3.05(2H, t, J=11.2Hz), 3.34(5H, s), 3.72(2H, brs), 4.00(2H, d, J=13.2Hz), 4.60-4.90(2H, m), 7.65(1H, s), 7.73(1H, s), 8.43(1H, d, J=1.9Hz), 8.87(1H, d, J=2.4Hz), 10.33(1H, brs), 12.28(1H, brs), 13.00(1H, s). |
| 65 | 1.61-1.73(2H, m), 1.90-1.99(2H, m), 2.51-2.54(1H, m), 2.81(6H, m), 3.05(2H, t, J=11.3Hz), 4.01(2H, d, J=13.2Hz), 4.74(2H, brs), 7.69(1H, s), 7.72(1H, s), |

TABLE 27-continued

| Ex | Data |
|---|---|
| | 8.43(1H, d, J=1.5Hz), 8.87(1H, d, J=1.9 Hz), 9.95(1H, brs), 12.27(1H, brs), 12.99(1H, s). |
| 71 | 0.87(3H, t, J=7.4Hz), 1.18-1.32(2H, m), 1.58-1.74(4H, m), 1.90-1.99(2H, m), 2.51-2.57(1H, m), 2.74(3H, d, J=3.9Hz), 2.98-3.17(4H, m), 4.01(2H, d, J=13.2Hz), 4.63-4.84(2H, m), 7.69(1H, s), 7.74(1H, s), 8.43(1H, d, J=2.4Hz), 8.87(1H, d, J=1.9Hz), 10.33(1H, brs), 12.28(1H, brs), 13.00(1H, s). |
| 84 | 1.52-1.98(12H, m), 2.52-2.58(1H, m), 3.05(2H, t, J=11.2Hz), 3.13-3.24(2H, m), 3.30-3.43(2H, m), 4.00(2H, d, J=12.7Hz), 4.74(2H, d, J=5.4Hz), 7.65(1H, s), 7.73(1H, s), 8.42(1H, d, J=2.0Hz), 8.87(1H, d, J=1.9Hz), 10.18(1H, brs), 12.27(1H, brs), 12.99(1H, s). |
| 85 | 1.48-1.77(10H, m), 1.82-1.99(4H, m), 2.52-2.59(1H, |

TABLE 27-continued

| Ex | Data |
|---|---|
| | m), 3.05(2H, t, J=11.3Hz), 3.16-3.43(4H, m), 4.00(2H, d, J=12.7Hz), 4.74(2H, d, J=4.9Hz), 7.65(1H, d, J=0.9Hz), 7.74(1H, d, J=1.0Hz), 8.43(1H, d, J=1.5Hz), 8.87(1H, d, J=1.9Hz), 9.98(1H, brs), 12.29(1H, brs), 12.99(1H, s). |
| 90 | 1.03-2.07(14H, m), 2.52-2.57(1H, m), 2.69(3H, d, J=4.4Hz), 3.05(2H, t, J=11.5Hz), 3.11-3.22(1H, m), 4.01(2H, d, J=13.2Hz), 4.58-4.89(2H, m), 7.66(1H, s), 7.75(1H, s), 8.42(1H, d, J=2.0Hz), 8.87(1H, d, J=2.0Hz), 10.11(1H, brs), 12.27(1H, brs), 13.01(1H, s). |
| 100 | 1.60-1.77(4H, m), 1.89-2.00(2H, m), 2.01-2.20(2H, m), 2.18-2.36(2H, m), 2.50-2.58(1H, m), 2.59-2.63(3H, d, J=4.4Hz), 3.05(2H, t, J=11.7Hz), 3.72-3.84(1H, m), 3.95-4.05(2H, m), 4.51-4.62(1H, m), 4.65-4.75(1H, m), 7.69(1H, s), 7.74(1H, s), 8.42(1H, d, J=2.2Hz), 8.87(1H, d, J=2.2Hz), 10.51(1H, brs), 12.28(1H, brs), 13.02(1H, brs) |
| 101 | 0.50-1.10(4H, m), 1.62-1.75(2H, m), 1.89-2.05(2H, m), 2.50-2.58(1H, m), 2.87(3H, brs), 3.05 (2H, t, J=11.2Hz), 3.11-3.15(1H, m), 3.92-4.06(2H, m), 4.64-5.08(2H, m), 7.62-7.83(2H, m), 8.42(1H, d, J=2.0Hz), 8.86(1H, d, J=2.0Hz), 10.25(1H, brs), 12.25(1H, brs), 13.00(1H, brs). |
| 104 | 1.22(3H, d, J=6.9Hz), 1.30(3H, d, J=6.8Hz), 1.60-1.74(2H, m), 1.90-2.00(2H, m), 2.50-2.58(1H, m), 2.67(3H, d, J=4.9Hz), 3.05(2H, t, J=11.3Hz), 3.30-3.45(1H, m), 4.00(2H, d, J=3.2Hz), 4.55-4.65(1H, m), 4.72-4.82(1H, m), 7.65(1H, s), 7.74(1H, d, J=1.5Hz), 8.42(1H, d, J=1.9Hz), 8.87(1H, d, J=2.0Hz), 10.05-10.25(1H, brs), 12.97(1H, s,). |
| 106 | 1.42(3H, d, J=, 6.3Hz), 1.61-1.73(3H, m), 1.87-1.96(4H, m), 2.20-2.23(1H, m), 2.49-2.57(1H, m), 3.03-3.08(2H, m), 3.13-3.22(1H, m), 3.48-3.64(2H, m), 4.01(2H, d, J=13.2Hz), 4.62-4.68 (2H, m), 4.95(1H, d, J=11.8Hz)7.66(1H, d, J=1.0Hz), 7.74(1H, d, J=1.0Hz), 8.43(1H, d, J=2.0Hz), 8.87(1H, d, J=2.4Hz), 10.21(1H, brs), 13.01(1H, s). |
| 107 | 1.42(3H, d, J=, 6.3Hz), 1.61-1.72(3H, m), 1.88-1.96(4H, m), 2.20-2.28(1H, m), 2.49-2.51(1H, m), 3.04-3.09(2H, m), 3.15-3.20(1H, m), 3.42-3.54(2H, m), 4.01(2H, d, J=12.7Hz), 4.66(1H, dd, J=7.8, 15.1Hz), 4.97(1H, d, J=11.2Hz), 7.65(1H, d, J=1.0Hz), 7.74(1H, d, J=1.0Hz), 8.42(1H, d, J=2.0Hz), 8.87(1H, d, J=2.2Hz), 9.98(1H, brs), 13.01(1H, s). |
| 108 | 1.05(3H, dd, J=1.5, 6.4Hz), 1.55-1.72(3H, m), 1.90-2.00(2H, m), 2.05-2.20(1H, m), 2.28-2.40 (1H, m), 2.50-2.60(1H, m), 2.70-2.80(1H, m), 3.05(2H, t, J=10.8Hz), 3.00-3.60(3H, m), 3.95-4.05(2H, d, J=13.2Hz), 4.75-4.80(2H, m), 7.67-7.69(1H, m), 7.72(1H, d, J=1.0Hz), 8.43(1H, d, J=1.9Hz), 8.83(1H, d, J=1.9Hz), 10.75-10.95(1H, brd), 12.97(1H, s).. |
| 109 | 1.05(3H, d, J=, 6.3Hz), 1.64-1.72(3H, m), 1.91-1.96(2H, m), 2.08-2.33(2H, m), 2.50-2.51(1H, m), 2.73-2.80(1H, m), 3.03-3.08(2H, m), 3.25-3.63(3H, m), 4.01(2H, d, J=13.2Hz), 4.76-4.86 (2H, m), 7.68(1H, d, J=1.5Hz), 7.73(1H, d, J=1.5Hz), 8.43(1H, d, J=1.9Hz), 8.87(1H, d, J=1.9Hz), 10.73(1H, brs), 12.99(1H, s). |
| 110 | 1.05-1.13(3H, m), 1.62-1.72(2H, m), 1.91-1.98(2H, m), 2.50-2.56(1H, m), 2.76-2.84(3H, m), 3.00-3.10(2H, m), 3.30-3.60(5H, m), 3.76-3.93(1H, m), 3.96-4.40(2H, m), 4.62-4.85(2H, m), 7.64(1H, d, J=3.9), 7.74(1H, s), 8.43(1H, d, J=1.9Hz), 8.87(1H, d, J=2.0Hz), 9.76-10.04(1H, m), 13.00(1H, s). |
| 111 | 1.05-1.13(3H, m), 1.62-1.72(2H, m), 1.91-1.96(2H, m), 2.50-2.55(1H, m), 2.76-2.84(3H, m), 3.00-3.10(2H, m), 3.25-3.60(5H, m), 3.76-3.93(1H, m), 3.96-4.40(2H, m), 4.62-4.85(2H, m), 7.61-7.65(1H, m).74(1H, s), 8.43(1H, d, J=1.9Hz), 8.87(1H, d, J=2.4Hz), 9.66-9.93(1H, m), 12.27(1H, brs), 13.01(1H, s). |
| 150 | 0.87(3H, t, J=7.3Hz), 1.17-1.34(4H, m), 1.58-1.72(3H, m), 1.78(2H, d, J=13.2Hz), 2.73(3H, d, J=4.4Hz), 2.92(2H, t, J=11.5Hz), 2.96-3.18(2H, m), 3.31(2H, d, J=6.3Hz), 4.11(2H, d, J=12.7Hz), 4.62-4.83(2H, m), 7.70(1H, s), 7.74(1H, s), 8.41(1H, d, J=2.0Hz), 8.86(1H, d, J=2.0Hz), 10.62(1H, brs), 12.97(1H, s). |
| 151 | 0.87(3H, t, J=7.3Hz), 1.16-1.34(2H, m), 1.57-1.80(4H, m), 2.72(3H, d, J=4.4Hz), 2.94-3.17(2H, m), |

TABLE 27-continued

| Ex | Data |
|---|---|
| | 3.45-3.60(4H, m), 4.60-4.80(2H, m), 7.50(1H, brs), 7.70(1H, s), 7.73(1H, s), 8.32(1H, d, J=2.0Hz), 8.77 (1H, d, J=2.0Hz), 10.86(1H, brs), 12.79(1H, s). |
| 153 | 0.87(3H, t, J=7.3Hz), 1.18-1.32(2H, m), 1.57-1.72(2H, m), 2.74(3H, d, J=4.4Hz), 2.96-3.19(2H, m), 3.32(2H, brs), 3.73-4.09(4H, m), 4.62-4.84(2H, m), 7.70(1H, d, J=1.0Hz), 7.74(1H, d, J=1.0Hz), 8.07(1H, s), 8.48(1H, d, J=2.0Hz), 8.89(1H, d, J=2.0Hz), 10.39(1H, brs), 13.05(1H, s). |
| 221 | 1.44(3H, d, J=6.3Hz), 1.62-1.72(1H, m), 1.87-1.97(2H, m), 2.18-2.26(1H, m), 2.66(2H, d, J=7.4Hz), 2.92-2.99(1H, m), 3.12-3.20(1H, m), 3.49-3.57(3H, m), 4.01-4.05(2H, m), 4.46(1H, t, 8.8Hz), 4.62(1H, dd, J=7.3, 15.1Hz), 4.91(1H, dJ=14.7Hz).68(1H, d, J=1.0Hz), 7.73(1H, d, J=1.4Hz), 8.27(1H, d, J=2.0Hz), 8.77(1H, d, J=2.0Hz), 10.56(1H, brs), 12.84(1H, s). |
| 222 | 1.43(3H, d, J=6.4Hz), 1.62-1.71(1H, m), 1.87-1.98(2H, m), 2.18-2.23(1H, m), 2.66(2H, d, J=7.8Hz), 2.89-2.99(1H, m), 3.12-3.21(1H, m), 3.48-3.57(3H, m), 4.01-4.05(2H, m), 4.43-4.48(1H, m), 4.60-4.66(1H, m), 4.92(1H, d, J=12.2Hz), 7.67(1H, s), 7.74(1H, d, J=1.0Hz), 8.27(1H, d, J=2.0Hz), 8.77(1H, d, J=2.0Hz), 10.42(1H, brs), 12.84(1H, s). |
| 225 | 1.42(3H, d, J=, 6.4Hz), 1.60-1.70(1H, m), 1.86-1.97(4H, m), 2.23-2.26(3H, m), 3.13(3H, s), 3.15-3.20(1H, m), 3.40-3.60(4H, m), 4.62-4.67(1H, m), 4.95(1H, d, J=15.1Hz), 7.65(1H, d, J=0.9Hz), 7.74(1H, d, J=1.5Hz), 8.38(1H, d, J=1.9Hz), 8.82(1H, d, J=2.4Hz), 10.08(1H, brs), 12.93(1H, s). |
| 226 | 1.45(3H, d, J=, 6.3Hz), 1.63-1.73(1H, m), 1.84-1.97(4H, m), 2.18-2.27(3H, m), 3.13(3H, s), 3.16-3.20(1H, m), 3.39-3.59(4H, m), 4.63(1H, dd, J=7.3, 15.1Hz), 4.90(1H, d, J=12.2Hz), 7.68(1H, d, J=1.0Hz), 7.74(1H, d, J=1.0Hz), 8.39(1H, d, J=2.0Hz), 8.82(1H, d, J=1.9Hz), 10.75(1H, brs), 12.92 (1H, s). |
| 227 | 1.22(3H, d, J=6.9Hz), 1.32(3H, d, J=6.3Hz), 1.84-1.91(2H, m), 2.23-2.27(2H, m), 2.65(3H, d, J=4.9Hz), 3.13(3H, s), 3.56-3.61(3H, m), 4.58(1H, dd, J=5.9, 15.2Hz), 4.76(1H, dd, J=3.9, 4.7Hz).67(1H, s), 7.74(1H, s), 8.39(1H, d, J=2.0Hz), 8.82(1H, d, J=1.9Hz), 10.57(1H, brs), 12.91(1H, s). |
| 271 | 1.19(3H, d, J=6.9Hz), 1.30(3H, d, J=6.3Hz), 1.60-1.72(2H, m), 1.90-1.98(2H, m), 2.28(3H, s), 2.52-2.58(1H, m), 2.65(3H, d, J=5.3Hz), 3.05(2H, t, J=11.2Hz), 3.52-3.64(1H, m), 4.00(2H, d, J=13.2Hz), 4.55-4.80(2H, m), 7.30(1H, s), 7.40(1H, s), 8.42(1H, d, J=2.5Hz), 8.75(1H, d, J=2.0Hz), 9.80-9.90(1H, brs), 12.97(1H, s). |
| 314 | 1.45(3H, d, J=6.3Hz), 1.55-1.72(3H, m), 1.90-2.00(4H, m), 2.15-2.25(1H, m), 2.55-2.65(1H. m), 3.20-3.32(3H, m), 3.45-3.55(2H, m), 4.45(2H, d, J=13.2Hz), 4.59-4.67(1H, m), 4.85-4.95(1H, m), 7.69(1H, d, J=1.5Hz), 7.72(1H, d, J=1.4Hz), 8.14(1H, dd, J=1.9, 15.1Hz), 8.75(1H, t, J=0.9Hz), 10.75(1H, brs), 12.90(1Hs). |
| 315 | 1.42(3H, d, J=6.4Hz), 1.55-1.70(3H, m), 1.85-2.00(4H, m), 2.15-2.25(1H, m), 2.54-2.65(1H, m), 3.10-3.22(3H, m), 3.45-3.60(2H, m), 4.23(2H, d, J=13.2Hz), 4.55-4.65(1H, m), 4.85-4.95(1H, m), 7.65(1H, d, J=1.0Hz), 7.75(1H, s), 8.13(1H, dd, J=2.0, 15.1Hz), 8.75(1H, s), 10.67(1H, brs), 12.90(1H, s). |

Structures of the other compounds of the present invention are shown in Tables 28 to 41 below. They can be produced easily by using the methods described in production examples and examples, or methods obvious to one skilled in the art, or modifications thereof.

TABLE 28

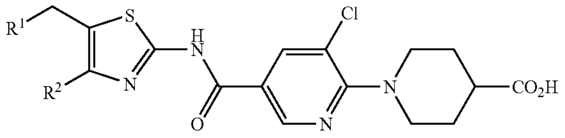

| No | $R^1$ | $R^2$ |
|---|---|---|
| A1 | EtN(Me)— | 4-Cl-2-The |
| A2 | nPrN(Me)— | 4-Cl-2-The |
| A3 | iPrN(Me)— | 4-Cl-2-The |
| A4 | iBuN(Me)— | 4-Cl-2-The |
| A5 | sBuN(Me)— | 4-Cl-2-The |
| A6 | tBuN(Me)— | 4-Cl-2-The |
| A7 | tBuCH$_2$N(Me)— | 4-Cl-2-The |
| A8 | cPenN(Me)— | 4-Cl-2-The |
| A9 | cPrCH$_2$N(Me)— | 4-Cl-2-The |
| A10 | cBuCH$_2$N(Me)— | 4-Cl-2-The |
| A11 | MeO H(Me)CH$_2$N(Me)— | 4-Cl-2-The |
| A12 | nPrN(Et)— | 4-Cl-2-The |
| A13 | nBuN(Et)— | 4-Cl-2-The |
| A14 | iPrN(Et)— | 4-Cl-2-The |
| A15 | iBuN(Et)— | 4-Cl-2-The |
| A16 | sBuN(Et)— | 4-Cl-2-The |
| A17 | tBuN(Et)— | 4-Cl-2-The |
| A18 | tBuCH$_2$N(Et)— | 4-Cl-2-The |
| A19 | cPrN(Et)— | 4-Cl-2-The |
| A20 | cBuN(Et)— | 4-Cl-2-The |
| A21 | cPenN(Et)— | 4-Cl-2-The |
| A22 | cHexN(Et)— | 4-Cl-2-The |
| A23 | cPrCH$_2$N(Et)— | 4-Cl-2-The |
| A24 | cBuCH$_2$N(Et)— | 4-Cl-2-The |
| A25 | MeO(CH$_2$)$_2$N(Et)— | 4-Cl-2-The |
| A26 | MeOCH$_2$CH(Me)N(Et)— | 4-Cl-2-The |
| A27 | MeOCH(Me)CH$_2$N(Et)— | 4-Cl-2-The |
| A28 | (MeO(CH$_2$)$_2$)$_2$N— | 4-Cl-2-The |
| A29 | MeO(CH$_2$)$_2$—N(cPr)— | 4-Cl-2-The |
| A30 | MeO(CH$_2$)$_2$—N(cBu)— | 4-Cl-2-The |
| A31 | EtO(CH$_2$)$_2$N(Et)— | 4-Cl-2-The |
| A32 | nPrO(CH$_2$)$_2$N(Et)— | 4-Cl-2-The |
| A33 | iPrO(CH$_2$)$_2$N(Et)— | 4-Cl-2-The |
| A34 | MeO(CH$_2$)$_3$N(Et)— | 4-Cl-2-The |
| A35 | 2-Me-azet | 4-Cl-2-The |
| A36 | 3-Me-azet | 4-Cl-2-The |
| A37 | 3,3-diMe-azet | 4-Cl-2-The |
| A38 | cPrCH$_2$N(Et)— | 4-Me-2-The |
| A39 | cBuCH$_2$N(Et)— | 4-Me-2-The |
| A40 | 2-Me-pyrr | 4-Cl-2-The |
| A41 | 3-Me-pyrr | 4-Cl-2-The |
| A42 | 3,4-diMe-pyrr | 4-Cl-2-The |
| A43 | 3,3-diMe-pyrr | 4-Cl-2-The |
| A44 | 2-Me-pipe | 4-Cl-2-The |
| A45 | 3-Me-pipe | 4-Cl-2-The |
| A46 | 4-Me-pipe | 4-Cl-2-The |
| A47 | 3,3-diMe-pipe | 4-Cl-2-The |
| A48 | 4,4-diMe-pipe | 4-Cl-2-The |
| A49 | EtN(Me)— | 4-Me-2-The |
| A50 | nPrN(Me)— | 4-Me-2-The |
| A51 | sBuN(Me)— | 4-Me-2-The |
| A52 | tBuN(Me)— | 4-Me-2-The |
| A53 | tBuCH$_2$N(Me)— | 4-Me-2-The |
| A54 | cPrN(Me)— | 4-Me-2-The |
| A55 | cPenN(Me)— | 4-Me-2-The |
| A56 | cPrCH$_2$N(Me)— | 4-Me-2-The |
| A57 | cBuCH$_2$N(Me)— | 4-Me-2-The |
| A58 | MeO(CH$_2$)$_2$N(Me)— | 4-Me-2-The |
| A59 | MeOCH$_2$OH(Me)N(Me)— | 4-Me-2-The |
| A60 | MeOCH(Me)CH$_2$N(Me)— | 4-Me-2-The |
| A61 | EtO(CH$_2$)$_2$N(Me)— | 4-Me-2-The |
| A62 | nPrO(CH$_2$)$_2$N(Me)— | 4-Me-2-The |
| A63 | iPrO(CH$_2$)$_2$N(Me)— | 4-Me-2-The |
| A64 | MeO(CH$_2$)$_3$N(Me)— | 4-Me-2-The |
| A65 | Et$_2$N— | 4-Me-2-The |
| A66 | nPrN(Et)— | 4-Me-2-The |
| A67 | nBuN(Et)— | 4-Me-2-The |
| A68 | iPrN(Et)— | 4-Me-2-The |
| A69 | iBuN(Et)— | 4-Me-2-The |

TABLE 28-continued

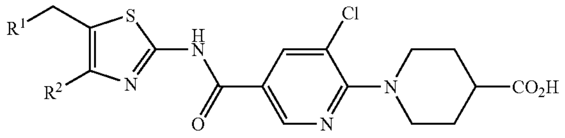

| No | $R^1$ | $R^2$ |
|---|---|---|
| A70 | sBuN(Et)— | 4-Me-2-The |
| A71 | tBuN(Et)— | 4-Me-2-The |
| A72 | tBuCH$_2$N(Et)— | 4-Me-2-The |
| A73 | cPrN(Et)— | 4-Me-2-The |
| A74 | cBuN(Et)— | 4-Me-2-The |
| A75 | cPenN(Et)— | 4-Me-2-The |
| A76 | cHexN(Et)— | 4-Me-2-The |
| A77 | MeO(CH$_2$)$_2$N(Me)— | 4-Br-2-The |
| A78 | pipe | 4-Br-2-The |
| A79 | MeO(CH$_2$)$_2$N(Et)— | 4-Me-2-The |
| A80 | MeOCH$_2$CH(Me)N(Et)— | 4-Me-2-The |
| A81 | MeOCH(Me)CH$_2$N(Et)— | 4-Me-2-The |
| A82 | EtO(CH$_2$)$_2$N(Et)— | 4-Me-2-The |
| A83 | nPrO(CH$_2$)$_2$N(Et)— | 4-Me-2-The |
| A84 | iPrO(CH$_2$)$_2$N(Et)— | 4-Me-2-The |
| A85 | MeO(CH$_2$)$_3$N(Et)— | 4-Me-2-The |
| A86 | azet | 4-Me-2-The |
| A87 | pyrr | 4-Me-2-The |
| A88 | pipe | 4-Me-2-The |
| A89 | Azepan-1-yl | 4-Me-2-The |
| A90 | Azocan-1-yl | 4-Me-2-The |
| A91 | 2-Me-azet | 4-Me-2-The |
| A92 | 3-Me-azet | 4-Me-2-The |
| A93 | 3,3-diMe-azet | 4-Me-2-The |
| A94 | 2-Me-pyrr | 4-Me-2-The |
| A95 | 3-Me-pyrr | 4-Me-2-The |
| A96 | 3,4-diMe-pyrr | 4-Me-2-The |
| A97 | 3,3-diMe-pyrr | 4-Me-2-The |
| A98 | 2-Me-pipe | 4-Me-2-The |
| A99 | 3-Me-pipe | 4-Me-2-The |
| A100 | 4-Me-pipe | 4-Me-2-The |
| A101 | 3,3-diMe-pipe | 4-Me-2-The |
| A102 | 4,4-diMe-pipe | 4-Me-2-The |
| A103 | Me$_2$N— | 4-Br-2-The |
| A104 | nBuN(Me)— | 4-Br-2-The |
| A105 | cHexN(Me)— | 4-Br-2-The |
| A106 | 2-Et-azet | 4-Cl-2-The |
| A107 | 3-Et-azet | 4-Cl-2-The |
| A108 | 2-Et-pyrr | 4-Cl-2-The |
| A109 | 3-Et-pyrr | 4-Cl-2-The |
| A110 | 2-Et-pipe | 4-Cl-2-The |
| A111 | 3-Et-pipe | 4-Cl-2-The |
| A112 | 4-Et-pipe | 4-Cl-2-The |
| A113 | 2-MeOCH$_2$-azet | 4-Cl-2-The |
| A114 | 3-MeOCH$_2$-azet | 4-Cl-2-The |
| A115 | 2-MeOCH$_2$-pyrr | 4-Cl-2-The |
| A116 | 3-MeOCH$_2$-pyrr | 4-Cl-2-The |
| A117 | 2-MeOCH$_2$-pipe | 4-Cl-2-The |
| A118 | 3-MeOCH$_2$-pipe | 4-Cl-2-The |
| A119 | 4-MeOCH$_2$-pipe | 4-Cl-2-The |
| A120 | 3-MeO-azet | 4-Cl-2-The |
| A121 | 3-MeO-pyrr | 4-Cl-2-The |
| A122 | 3-MeO-pipe | 4-Cl-2-The |
| A123 | Me$_2$N— | 4-F-2-The |
| A124 | nBuN(Me)— | 4-F-2-The |
| A125 | cHexN(Me)— | 4-F-2-The |
| A126 | MeO(CH$_2$)$_2$N(Me)— | 4-F-2-The |
| A127 | pipe | 4-F-2-The |
| A128 | Me$_2$N— | 4-Et-2-The |
| A129 | nBuN(Me)— | 4-Et-2-The |
| A130 | cHexN(Me)— | 4-Et-2-The |
| A131 | MeO(CH$_2$)$_2$N(Me)— | 4-Et-2-The |
| A132 | pipe | 4-Et-2-The |
| A133 | Me$_2$N— | 5-Cl-2-The |
| A134 | nBuN(Me)— | 5-Cl-2-The |
| A135 | cHexN(Me)— | 5-Cl-2-The |
| A136 | MeO(CH$_2$)$_2$N(Me)— | 5-Cl-2-The |
| A137 | pipe | 5-Cl-2-The |
| A138 | Me$_2$N— | 4-F—Ph |

TABLE 28-continued

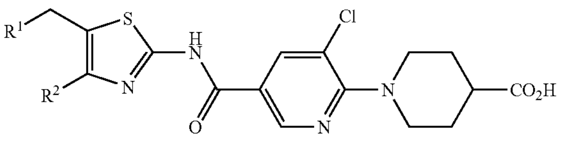

| No | $R^1$ | $R^2$ |
|---|---|---|
| A139 | cHexN(Me)— | 4-F—Ph |
| A140 | $MeO(CH_2)_2N(Me)$— | 4-F—Ph |
| A141 | $Me_2N$— | 3-Cl—Ph |
| A142 | nBuN(Me)— | 3-Cl—Ph |
| A143 | cHex(Me)— | 3-Cl—Ph |
| A144 | $MeO(CH_2)_2N(Me)$— | 3-Cl—Ph |
| A145 | pipe | 3-Cl—Ph |
| A146 | $Me_2N$— | $3-F_3C$—Ph |
| A147 | nBuN(Me)— | $3-F_3C$—Ph |
| A148 | cHexN(Me)— | $3-F_3C$—Ph |
| A149 | $MeO(CH_2)_2N(Me)$— | $3-F_3C$—Ph |
| A150 | 2-Et-azet | 4-Me-2-The |
| A151 | 3-Et-azet | 4-Me-2-The |
| A152 | 2-Et-pyrr | 4-Me-2-The |
| A153 | 3-Et-pyrr | 4-Me-2-The |
| A154 | 2-Et-pipe | 4-Me-2-The |
| A155 | 3-Et-pipe | 4-Me-2-The |
| A156 | 4-Et-pipe | 4-Me-2-The |
| A157 | $2-MeOCH_2$-azet | 4-Me-2-The |
| A158 | $3-MeOCH_2$-azet | 4-Me-2-The |
| A159 | $2-MeOCH_2$-pyrr | 4-Me-2-The |
| A160 | $3-MeOCH_2$-pyrr | 4-Me-2-The |
| A161 | $2-MeOCH_2$-pipe | 4-Me-2-The |
| A162 | $3-MeOCH_2$-pipe | 4-Me-2-The |
| A163 | $4-MeOCH_2$-pipe | 4-Me-2-The |
| A164 | 3-MeO-azet | 4-Me-2-The |
| A165 | 3-MeO-pyrr | 4-Me-2-The |
| A166 | 3-MeO-pipe | 4-Me-2-The |
| A167 | 4-MeO-pipe | 4-Cl-2-The |
| A168 | 3-F-azet | 4-Cl-2-The |
| A169 | 3-F-pyrr | 4-Cl-2-The |
| A170 | 3-F-pipe | 4-Cl-2-The |
| A171 | 4-F-pipe | 4-Cl-2-The |
| A172 | 4-MeO-pipe | 4-Me-2-The |
| A173 | 3-F-azet | 4-Me-2-The |
| A174 | 3-F-pyrr | 4-Me-2-The |
| A175 | 3-F-pipe | 4-Me-2-The |
| A176 | 4-F-pipe | 4-Me-2-The |

TABLE 29

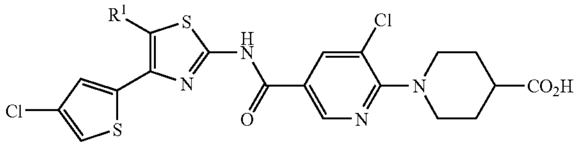

| No | $R^1$ |
|---|---|
| B1 | $Me_2NCH(Me)$— |
| B2 | $Me_2NC(Me)_2$— |
| B3 | $Me_2N(CH_2)_2$— |
| B4 | $Me_2N(CH_2)_3$— |
| B5 | nBuN(Me)—CH(Me)— |
| B6 | nBuN(Me)—$C(Me)_2$— |
| B7 | nBuN(Me)—$(CH_2)_3$— |
| B8 | cHexN(Me)—CH(Me)— |
| B9 | cHexN(Me)—$C(Me)_2$— |
| B10 | cHexN(Me)—$(CH_2)_2$— |
| B11 | cHexN(Me)—$(CH_2)_3$— |
| B12 | $MeO(CH_2)_2N(Me)$—CH(Me)— |
| B13 | $MeO(CH_2)_2N(Me)$—$C(Me)_2$— |
| B14 | $MeO(CH_2)_2N(Me)$—$(CH_2)_2$— |
| B15 | $MeO(CH_2)_2N(Me)$—$(CH_2)_3$— |
| B16 | pipe-CH(Me)— |

TABLE 29-continued

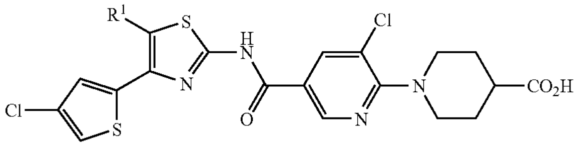

| No | $R^1$ |
|---|---|
| B17 | pipe-$C(Me)_2$— |
| B18 | pipe-$(CH_2)_2$— |
| B19 | pipe-$(CH_2)_3$— |
| B20 | (Azepan-1-yl)-CH(Me)— |
| B21 | (Azepan-1-yl)-$C(Me)_2$— |
| B22 | (Azepan-1-yl)-$(CH_2)_2$— |
| B23 | (Azepan-1-yl)-$(CH_2)_3$— |
| B24 | (Azocan-1-yl)-CH(Me)— |
| B25 | (Azocan-1-yl)-$C(Me)_2$— |
| B26 | (Azocan-1-yl)-$(CH_2)_2$— |
| B27 | (Azocan-1-yl)-$(CH_2)_3$— |

TABLE 30

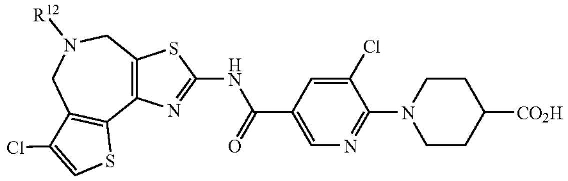

| No | $R^{12}$ |
|---|---|
| C1 | Me |
| C2 | Et |
| C3 | nPr |
| C4 | iPr |
| C5 | iBu |
| C6 | sBu |
| C7 | tBu |
| C8 | $tBuCH_2$— |
| C9 | cPr |
| C10 | cBu |
| C11 | cPen |
| C12 | cHex |
| C13 | $cPrCH_2$— |
| C14 | $cBuCH_2$— |
| C15 | $MeOCH_2CH(Me)$— |
| C16 | MeO $CH(Me)CH_2$— |
| C17 | $EtO(CH_2)_2$— |
| C18 | $nPrO(CH_2)_2$— |
| C19 | $iPrO(CH_2)_2$— |
| C20 | $MeO(CH_2)_3$— |

TABLE 31

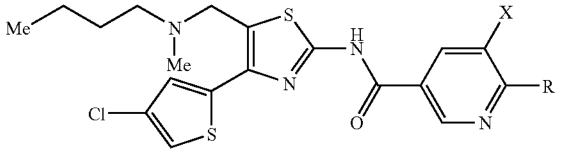

| No | X | R |
|---|---|---|
| D1 | Cl | $3-HO_2C$-pipe |
| D2 | Cl | $4-HO_2CCH_2$-pipe |
| D3 | Cl | $4-HO_2CCH_2$-pipa |
| D4 | Cl | $3-HO_2CCH_2$-pyrr |
| D5 | Cl | $3-HO_2CCH_2$-azet |
| D6 | Cl | 4-HO-pipe |

TABLE 31-continued

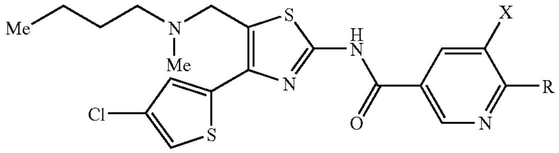

| No | X | R |
|---|---|---|
| D7 | Cl | 3-HO-pipe |
| D8 | Cl | 3-HO-pyrr |
| D9 | Cl | 4-$HOCH_2$-pipe |
| D10 | Cl | 3-HO-4-$HO_2C$-pipe |
| D11 | Cl | 4-HO-4-$HO_2C$-pipe |
| D12 | Cl | 4-HO-4-$HO_2CCH_2$-pipe |
| D13 | Cl | 4-$HO_2CCH(OH)$-pipe |
| D14 | Cl | $HO(CH_2)_2NH$— |
| D15 | Cl | $HO(CH_2)_3N(Me)$— |
| D16 | Cl | $HO(CH_2)_2N(Me)$— |
| D17 | Cl | $HO(CH_2)_3O$— |
| D18 | Cl | $HO(CH_2)_2O$— |
| D19 | Cl | $HO_2C(CH_2)_2NH$— |
| D20 | Cl | $HO_2CCH_2NH$— |
| D21 | Cl | $HO_2C(CH_2)_3N(Me)$— |
| D22 | Cl | $HO_2C(CH_2)_2N(Me)$— |
| D23 | Cl | $HO_2CCH_2N(Me)$— |
| D24 | Cl | $HO_2C(CH_2)_3O$— |
| D25 | Cl | $HO_2C(CH_2)_2O$— |
| D26 | Cl | $HO_2CCH_2O$— |
| D27 | F | 4-$HO_2C$-pipe |
| D28 | F | 3-$HO_2C$-pipe |
| D29 | F | 3-$HO_2C$-pyrr |
| D30 | F | 4-$HO_2CCH_2$-pipe |
| D31 | F | 4-$HO_2CCH_2$-pipa |
| D32 | F | 3-$HO_2CCH_2$-pyrr |
| D33 | F | 3-$HO_2CCH_2$-azet |
| D34 | F | 4-HO-pipe |
| D35 | F | 3-HO-pipe |
| D36 | F | 3-HO-pyrr |
| D37 | F | 4-$HOCH_2$-pipe |
| D38 | F | 4-$HO_2CCH_2O$-pipe |
| D39 | F | 3-HO-4-$HO_2C$-pipe |
| D40 | F | 4-HO-4-$HO_2C$-pipe |
| D41 | F | 4-HO-4-$HO_2CCH_2$-pipe |
| D42 | F | 4-$HO_2CCH(OH)$-pipe |
| D43 | F | $HO(CH_2)_3NH$— |
| D44 | F | $HO(CH_2)_2NH$— |
| D45 | F | $HO(CH_2)_3N(Me)$— |
| D46 | F | $HO(CH_2)_2N(Me)$— |
| D47 | F | $HO(CH_2)_3O$— |
| D48 | F | $HO(CH_2)_2O$— |
| D49 | F | $HO_2C(CH_2)_3NH$— |
| D50 | H | 4-$HO_2C$-pipe |
| D51 | H | 3-$HO_2C$-pipe |
| D52 | H | 3-$HO_2C$-pyrr |
| D53 | H | 3-$HO_2C$-azet |
| D54 | H | 4-$HO_2CCH_2$-pipe |
| D55 | H | 4-$HO_2CCH_2$-pipa |
| D56 | H | 3-$HO_2CCH_2$-pyrr |
| D57 | H | 3-$HO_2CCH_2$-azet |
| D58 | H | $HO_2C(CH_2)_3NH$— |
| D59 | H | $HO_2C(CH_2)_2NH$— |
| D60 | H | $HO_2CCH_2NH$— |
| D61 | H | $HO_2C(CH_2)_3N(Me)$— |
| D62 | H | $HO_2C(CH_2)_2N(Me)$— |
| D63 | H | $HO_2CCH_2N(Me)$— |
| D64 | H | $HO_2C(CH_2)_3O$— |
| D65 | H | $HO_2C(CH_2)_2O$— |
| D66 | H | $HO_2CCH_2O$— |
| D67 | Br | 4-$HO_2C$-pipe |
| D68 | Br | 3-$HO_2C$-pipe |
| D69 | Br | 3-$HO_2C$-pyrr |
| D70 | Br | 3-$HO_2C$-azet |
| D71 | Br | 4-$HO_2CCH_2$-pipe |
| D72 | Br | 4-$HO_2CCH_2$-pipa |
| D73 | Br | 3-$HO_2CCH_2$-pyrr |
| D74 | Br | 3-$HO_2CCH_2$-azet |

TABLE 31-continued

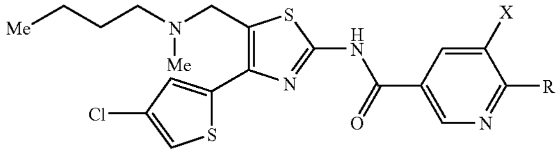

| No | X | R |
|---|---|---|
| D75 | Br | $HO_2C(CH_2)_3NH$— |
| D76 | Br | $HO_2C(CH_2)_2NH$— |
| D77 | Br | $HO_2CCH_2NH$— |
| D78 | Br | $HO_2C(CH_2)_3N(Me)$— |
| D79 | Br | $HO_2C(CH_2)_2N(Me)$— |
| D80 | Br | $HO_2CCH_2N(Me)$— |
| D81 | Br | $HO_2C(CH_2)_3O$— |
| D82 | Br | $HO_2C(CH_2)_2O$— |
| D83 | Br | $HO_2CCH_2O$— |
| D84 | $CF_3$ | 4-$HO_2C$-pipe |
| D85 | F | $HO_2C(CH_2)_2NH$— |
| D86 | F | $HO_2CCH_2NH$— |
| D87 | F | $HO_2C(CH_2)_3N(Me)$— |
| D88 | F | $HO_2C(CH_2)_2N(Me)$— |
| D89 | F | $HO_2CCH_2N(Me)$— |
| D90 | F | $HO_2C(CH_2)_3O$— |
| D91 | F | $HO_2C(CH_2)_2O$— |
| D92 | F | $HO_2CCH_2O$— |
| D93 | Me | 4-$HO_2C$-pipe |
| D94 | Me | 3-$HO_2C$-pipe |
| D95 | Me | 3-$HO_2C$-pyrr |
| D96 | Me | 3-$HO_2C$-azet |
| D97 | Me | 4-$HO_2CCH_2$-pipe |
| D98 | Me | 4-$HO_2CCH_2$-pipa |
| D99 | Me | 3-$HO_2CCH_2$-pyrr |
| D100 | Me | 3-$HO_2CCH_2$-azet |
| D101 | Me | $HO_2C(CH_2)_3NH$— |
| D102 | Me | $HO_2C(CH_2)_2NH$— |
| D103 | Me | $HO_2CCH_2NH$— |
| D104 | Me | $HO_2C(CH_2)_3N(Me)$— |
| D105 | Me | $HO_2C(CH_2)_2N(Me)$— |
| D106 | Me | $HO_2CCH_2N(Me)$— |
| D107 | Me | $HO_2C(CH_2)_3O$— |
| D108 | Me | $HO_2C(CH_2)_2O$— |
| D109 | Me | $HO_2CCH_2O$— |
| D110 | MeO | 4-$HO_2C$-pipe |
| D111 | MeO | 3-$HO_2C$-pipe |
| D112 | MeO | 3-$HO_2C$-pyrr |
| D113 | MeO | 3-$HO_2C$-azet |
| D114 | MeO | 4-$HO_2CCH_2$-pipe |
| D115 | MeO | 4-$HO_2CCH_2$-pipa |
| D116 | MeO | 3-$HO_2CCH_2$-pyrr |
| D117 | MeO | 3-$HO_2CCH_2$-azet |
| D118 | MeO | $HO_2C(CH_2)_3NH$— |
| D119 | MeO | $HO_2C(CH_2)_2NH$— |
| D120 | MeO | $HO_2CCH_2NH$— |
| D121 | $CF_3$ | 3-$HO_2C$-pipe |
| D122 | $CF_3$ | 3-$HO_2C$-pyrr |
| D123 | $CF_3$ | 3-$HO_2C$-azet |
| D124 | $CF_3$ | 4-$HO_2CCH_2$-pipe |
| D125 | $CF_3$ | 4-$HO_2CCH_2$-pipa |
| D126 | $CF_3$ | 3-$HO_2CCH_2$-pyrr |
| D127 | $CF_3$ | 3-$HO_2CCH_2$-azet |
| D128 | $CF_3$ | $HO_2C(CH_2)_3NH$— |
| D129 | $CF_3$ | $HO_2C(CH_2)_2NH$— |
| D130 | $CF_3$ | $HO_2CCH_2NH$— |
| D131 | $CF_3$ | $HO_2C(CH_2)_3N(Me)$— |
| D132 | $CF_3$ | $HO_2C(CH_2)_2N(Me)$— |
| D133 | $CF_3$ | $HO_2CCH_2N(Me)$— |
| D134 | $CF_3$ | $HO_2C(CH_2)_3O$— |
| D135 | $CF_3$ | $HO_2C(CH_2)_2O$— |
| D136 | $CF_3$ | $HO_2CCH_2O$— |
| D137 | MeO | $HO_2C(CH_2)_3N(Me)$— |
| D138 | MeO | $HO_2C(CH_2)_2N(Me)$— |
| D139 | MeO | $HO_2CCH_2N(Me)$— |
| D140 | MeO | $HO_2C(CH_2)_3O$— |
| D141 | MeO | $HO_2C(CH_2)_2O$— |
| D142 | MeO | $HO_2CCH_2O$— |

TABLE 31-continued

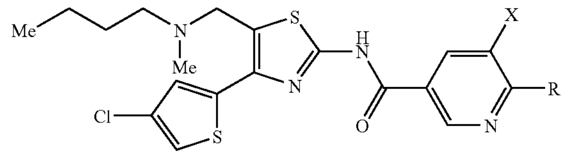

| No | X | R |
|---|---|---|
| D143 | Cl | 3-$HO_2C$-azet |
| D144 | F | 3-$HO_2C$-azet |

TABLE 32

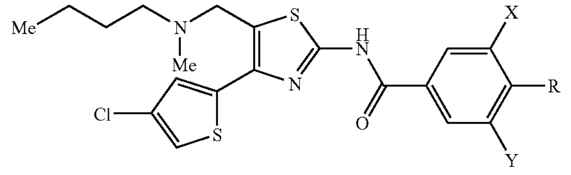

| No | X | Y | R |
|---|---|---|---|
| E1 | F | H | $HO(CH_2)_3NH$— |
| E2 | F | H | $HO(CH_2)_2NH$— |
| E3 | F | H | $HO(CH_2)_3N(Me)$— |
| E4 | F | H | $HO(CH_2)_2N(Me)$— |
| E5 | F | H | $HO(CH_2)_3O$— |
| E6 | F | H | $HO(CH_2)_2O$— |
| E7 | F | H | $HO_2C(CH_2)_3NH$— |
| E8 | F | H | $HO_2C(CH_2)_2NH$— |
| E9 | F | H | $HO_2CCH_2NH$— |
| E10 | F | H | $HO_2C(CH_2)_3N(Me)$— |
| E11 | F | H | $HO_2C(CH_2)_2N(Me)$— |
| E12 | F | H | $HO_2CCH_2N(Me)$— |
| E13 | F | H | $HO_2C(CH_2)_2O$— |
| E14 | F | H | $HO_2CCH_2O$— |
| E15 | Cl | H | $HO(CH_2)_3NH$— |
| E16 | Cl | H | $HO(CH_2)_2NH$— |
| E17 | Cl | H | $HO(CH_2)_3N(Me)$— |
| E18 | Cl | H | $HO(CH_2)_2N(Me)$— |
| E19 | Cl | H | $HO(CH_2)_3O$— |
| E20 | Cl | H | $HO(CH_2)_2O$— |
| E21 | Cl | H | $HO_2C(CH_2)_3NH$— |
| E22 | Cl | H | $HO_2C(CH_2)_2NH$— |
| E23 | Cl | H | $HO_2CCH_2NH$— |
| E24 | Cl | H | $HO_2C(CH_2)_3N(Me)$— |
| E25 | Cl | H | $HO_2C(CH_2)_2N(Me)$— |
| E26 | Cl | H | $HO_2CCH_2N(Me)$— |
| E27 | F | F | $HO(CH_2)_2NH$— |
| E28 | F | F | $HO(CH_2)_3N(Me)$— |
| E29 | F | F | $HO(CH_2)_2N(Me)$— |
| E30 | F | F | $HO(CH_2)_3O$— |
| E31 | F | F | $HO(CH_2)_2O$— |
| E32 | F | F | $HO_2C(CH_2)_3NH$— |
| E33 | F | F | $HO_2C(CH_2)_2NH$— |
| E34 | F | F | $HO_2CCH_2NH$— |
| E35 | F | F | $HO_2C(CH_2)_3N(Me)$— |
| E36 | F | F | $HO_2C(CH_2)_2N(Me)$— |
| E37 | F | F | $HO_2CCH_2N(Me)$— |
| E38 | F | F | $HO_2C(CH_2)_3O$— |
| E39 | F | F | $HO_2C(CH_2)_2O$— |
| E40 | F | F | $HO_2CCH_2O$— |
| E41 | Cl | F | $HO(CH_2)_3NH$— |
| E42 | Cl | F | $HO(CH_2)_2NH$— |
| E43 | Cl | F | $HO(CH_2)_3N(Me)$— |
| E44 | Cl | F | $HO(CH_2)_2N(Me)$— |
| E45 | Cl | F | $HO(CH_2)_3O$— |
| E46 | Cl | F | $HO(CH_2)_2O$— |
| E47 | Cl | F | $HO_2C(CH_2)_3NH$— |
| E48 | Cl | F | $HO_2C(CH_2)_2NH$— |
| E49 | Cl | F | $HO_2CCH_2NH$— |
| E50 | Cl | F | $HO_2C(CH_2)_3N(Me)$— |

TABLE 32-continued

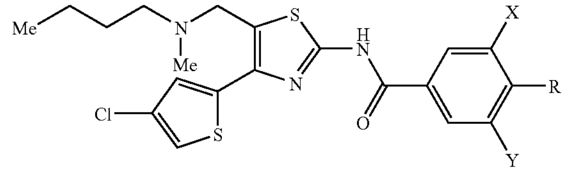

| No | X | Y | R |
|---|---|---|---|
| E51 | Cl | F | $HO_2C(CH_2)_2N(Me)$— |
| E52 | Cl | F | $HO_2CCH_2N(Me)$— |
| E53 | Cl | H | $HO_2C(CH_2)_3O$— |
| E54 | Cl | H | $HO_2C(CH_2)_2O$— |
| E55 | Cl | H | $HO_2CCH_2O$— |
| E56 | F | F | $HO(CH_2)_3NH$— |
| E57 | H | H | 4-$HO_2C$-pipe |
| E58 | H | H | 3-$HO_2C$-pipe |
| E59 | H | H | 3-$HO_2C$-pyrr |
| E60 | H | H | 3-$HO_2C$-azet |
| E61 | H | H | 4-$HO_2CCH_2$-pipe |
| E62 | H | H | 4-$HO_2CCH_2$-pipa |
| E63 | H | H | 3-$HO_2CCH_2$-pyrr |
| E64 | H | H | 3-$HO_2CCH_2$-azet |
| E65 | H | H | $HO_2C(CH_2)_3NH$— |
| E66 | H | H | $HO_2C(CH_2)_2NH$— |
| E67 | H | H | $HO_2CCH_2NH$— |
| E68 | H | H | $HO_2C(CH_2)_3N(Me)$— |
| E69 | H | H | $HO_2C(CH_2)_2N(Me)$— |
| E70 | H | H | $HO_2CCH_2N(Me)$— |
| E71 | H | H | $HO_2C(CH_2)_3O$— |
| E72 | H | H | $HO_2C(CH_2)_2O$— |
| E73 | H | H | $HO_2CCH_2O$— |
| E74 | Br | H | 4-$HO_2C$-pipe |
| E75 | Br | H | 3-$HO_2C$-pipe |
| E76 | Br | H | 3-$HO_2C$-pyrr |
| E77 | Br | H | 3-$HO_2C$-azet |
| E78 | Br | H | 4-$HO_2CCH_2$-pipe |
| E79 | Br | H | 4-$HO_2CCH_2$-pipa |
| E80 | Br | H | 3-$HO_2CCH_2$-pyrr |
| E81 | Br | H | 3-$HO_2CCH_2$-azet |
| E82 | Br | H | $HO_2C(CH_2)_3NH$— |
| E83 | Br | H | $HO_2C(CH_2)_2NH$— |
| E84 | Br | H | $HO_2CCH_2NH$— |
| E85 | Br | H | $HO_2C(CH_2)_3N(Me)$— |
| E86 | Br | H | $HO_2C(CH_2)_2N(Me)$— |
| E87 | Br | H | $HO_2CCH_2N(Me)$— |
| E88 | Br | H | $HO_2C(CH_2)_3O$— |
| E89 | Br | H | $HO_2C(CH_2)_2O$— |
| E90 | Br | H | $HO_2CCH_2O$— |
| E91 | $CF_3$ | H | 4-$HO_2C$-pipe |
| E92 | $CF_3$ | H | 3-$HO_2C$-pipe |
| E93 | $CF_3$ | H | 3-$HO_2C$-pyrr |
| E94 | $CF_3$ | H | 3-$HO_2C$-azet |
| E95 | $CF_3$ | H | 4-$HO_2CCH_2$-pipe |
| E96 | $CF_3$ | H | 4-$HO_2CCH_2$-pipa |
| E97 | Cl | F | $HO_2C(CH_2)_3O$— |
| E98 | Cl | F | $HO_2C(CH_2)_2O$— |
| E99 | Cl | F | $HO_2CCH_2O$— |
| E100 | Me | H | 4-$HO_2C$-pipe |
| E101 | Me | H | 3-$HO_2C$-pipe |
| E102 | Me | H | 3-$HO_2C$-pyrr |
| E103 | Me | H | 3-$HO_2C$-azet |
| E104 | Me | H | 4-$HO_2CCH_2$-pipe |
| E105 | Me | H | 4-$HO_2CCH_2$-pipa |
| E106 | Me | H | 3-$HO_2CCH_2$-pyrr |
| E107 | Me | H | 3-$HO_2CCH_2$-azet |
| E108 | Me | H | $HO_2C(CH_2)_3NH$— |
| E109 | Me | H | $HO_2C(CH_2)_2NH$— |
| E110 | Me | H | $HO_2CCH_2NH$— |
| E111 | Me | H | $HO_2C(CH_2)_3N(Me)$— |
| E112 | Me | H | $HO_2C(CH_2)_2N(Me)$— |
| E113 | Me | H | $HO_2CCH_2N(Me)$— |
| E114 | Me | H | $HO_2C(CH_2)_3O$— |
| E115 | Me | H | $HO_2C(CH_2)_2O$— |
| E116 | Me | H | $HO_2CCH_2O$— |
| E117 | MeO | H | 4-$HO_2C$-pipe |

TABLE 32-continued

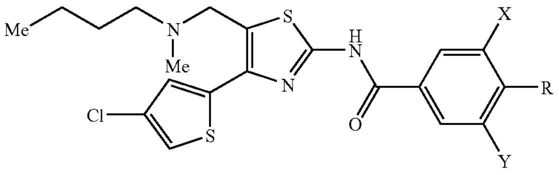

| No | X | Y | R |
|---|---|---|---|
| E118 | MeO | H | 3-$HO_2C$-pipe |
| E119 | MeO | H | 3-$HO_2C$-pyrr |
| E120 | MeO | H | 3-$HO_2C$-azet |
| E121 | MeO | H | 4-$HO_2CCH_2$-pipe |
| E122 | MeO | H | 4-$HO_2CCH_2$-pipa |
| E123 | MeO | H | 3-$HO_2CCH_2$-pyrr |
| E124 | MeO | H | 3-$HO_2CCH_2$-azet |
| El25 | MeO | H | $HO_2C(CH_2)_3NH$— |
| E126 | MeO | H | $HO_2C(CH_2)_2NH$— |
| E127 | MeO | H | $HO_2CCH_2NH$— |
| E128 | MeO | H | $HO_2C(CH_2)_3N(Me)$— |
| E129 | MeO | H | $HO_2C(CH_2)_2N(Me)$— |
| E130 | MeO | H | $HO_2CCH_2N(Me)$— |
| E131 | MeO | H | $HO_2C(CH_2)_3O$— |
| E132 | MeO | H | $HO_2C(CH_2)_2O$— |
| E133 | MeO | H | $HO_2CCH_2O$— |
| E134 | Cl | H | 4-$HO_2C$-pipe |
| E135 | Cl | H | 3-$HO_2C$-pipe |
| E136 | Cl | H | 3-$HO_2C$-pyrr |
| El37 | Cl | H | 3-$HO_2C$-azet |
| E138 | Cl | H | 4-$HO_2CCH_2$-pipe |
| E139 | Cl | H | 4-$HO_2CCH_2$-pipa |
| E140 | Cl | H | 3-$HO_2CCH_2$-pyrr |
| E141 | $CF_3$ | H | 3-$HO_2CCH_2$-pyrr |
| E142 | $CF_3$ | H | 3-$HO_2CCH_2$-azet |
| E143 | $CF_3$ | H | $HO_2C(CH_2)_3NH$— |
| E144 | $CF_3$ | H | $HO_2C(CH_2)_2NH$— |
| E145 | $CF_3$ | H | $HO_2CCH_2NH$— |
| E146 | $CF_3$ | H | $HO_2C(CH_2)_2NH$— |
| E147 | $CF_3$ | H | $HO_2CCH_2N(Me)$— |
| E148 | $CF_3$ | H | $HO_2C(CH_2)_3O$— |
| E149 | $CF_3$ | H | $HO_2C(CH_2)_2O$— |
| E150 | $CF_3$ | H | $HO_2CCH_2O$— |
| E151 | Cl | H | 3-$HO_2CCH_2$-azet |
| E152 | F | H | 4-$HO_2C$-pipe |
| E153 | F | H | 3-$HO_2C$-pipe |
| E154 | F | H | 3-$HO_2C$-pyrr |
| E155 | $CF_3$ | H | $HO_2C(CH_2)_3N(Me)$— |
| E156 | F | H | 3-$HO_2C$-azet |
| E157 | F | H | 4-$HO_2CCH_2$-pipe |
| E158 | F | H | 4-$HO_2CCH_2$-pipa |
| E159 | F | H | 3-$HO_2CCH_2$-pyrr |
| E160 | F | H | 3-$HO_2CCH_2$-azet |

TABLE 33

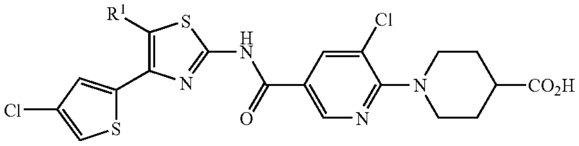

| No | $R^1$ |
|---|---|
| F1 | 1-Me-piperidin-2-yl |
| F2 | 1-Me-pyrrolidin-2-yl |
| F3 | 1-Me-azepan-2-yl |
| F4 | 1-Et-piperidin-2-yl |
| F5 | 1,4-diMe-piperidin-2-yl |
| F6 | 1-Me-4-nPr-piperidin-2-yl |
| F7 | 1-Me-4-nPrO-piperidin-2-yl |
| F8 | 1-Me-4-F-piperidin-2-yl |
| F9 | 1,5-diMe-piperidin-2-yl |

TABLE 33-continued

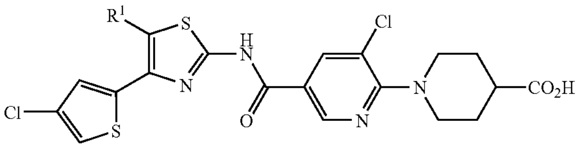

| No | $R^1$ |
|---|---|
| F10 | 1-Me-5-nPr-piperidin-2-yl |
| F11 | 1-Me-5-nPrO-piperidin-2-yl |
| F12 | 1-Me-5-F-piperidin-2-yl |
| F13 | 1,6-diMe-piperidin-2-yl |
| F14 | 1-Me-6-nPr-piperidin-2-yl |

TABLE 34

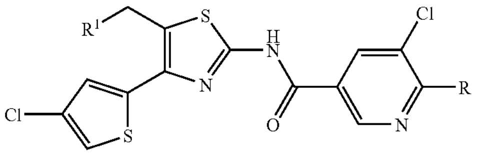

| No | $R^1$ | R |
|---|---|---|
| G1 | 2-Me-pyrr | 4-$HO_2C$-pipe |
| G2 | 2-Me-pyrr | 3-$HO_2C$-pipe |
| G3 | 2-Me-pyrr | 3-$HO_2C$-pyrr |
| G4 | 2-Me-pyrr | 3-$HO_2C$-azet |
| G5 | 2-Me-pyrr | 4-$HO_2CCH_2$-pipe |
| G6 | 2-Me-pyrr | 4-$HO_2CCH_2$-pipa |
| G7 | 2-Me-pyrr | 3-$HO_2CCH_2$-pyrr |
| G8 | 2-Me-pyrr | 3-$HO_2CCH_2$-azet |
| G9 | 3-Me-pyrr | 4-$HO_2C$-pipe |
| G10 | 3-Me-pyrr | 3-$HO_2C$-pipe |
| G11 | 3-Me-pyrr | 3-$HO_2C$-pyrr |
| G12 | 3-Me-pyrr | 3-$HO_2C$-azet |
| G13 | 3-Me-pyrr | 4-$HO_2CCH_2$-pipe |
| G14 | 3-Me-pyrr | 4-$HO_2CCH_2$-pipa |
| G15 | 3-Me-pyrr | 3-$HO_2CCH_2$-pyrr |
| G16 | 3-Me-pyrr | 3-$HO_2CCH_2$-azet |
| G17 | 2-Me-pyrr | $HO_2C(CH_2)_3NH$— |
| G18 | 2-Me-pyrr | $HO_2C(CH_2)_2NH$— |
| G19 | 2-Me-pyrr | $HO_2CCH_2NH$— |
| G20 | 2-Me-pyrr | $HO_2C(CH_2)_3N(Me)$— |
| G21 | 2-Me-pyrr | $HO_2C(CH_2)_2N(Me)$— |
| G22 | 2-Me-pyrr | $HO_2CCH_2N(Me)$— |
| G23 | 2-Me-pyrr | $HO_2C(CH_2)_3O$— |
| G24 | 2-Me-pyrr | $HO_2C(CH_2)_2O$— |
| G25 | 2-Me-pyrr | $HO_2CCH_2O$— |
| G26 | iBuN(Me)— | 4-$HO_2C$-pipe |
| G27 | iBuN(Me)— | 3-$HO_2C$-pipe |
| G28 | iBuN(Me)— | 3-$HO_2C$-pyrr |
| G29 | iBuN(Me)— | 3-$HO_2C$-azet |
| G30 | iBuN(Me)— | 4-$HO_2CCH_2$-pipe |
| G31 | iBuN(Me)— | 4-$HO_2CCH_2$-pipa |
| G32 | iBuN(Me)— | 3-$HO_2CCH_2$-pyrr |
| G33 | iBuN(Me)— | 3-$HO_2CCH_2$-azet |
| G34 | iBuN(Me)— | $HO_2C(CH_2)_3NH$— |
| G35 | iBuN(Me)— | $HO_2C(CH_2)_2NH$— |
| G36 | iBuN(Me)— | $HO_2CCH_2NH$— |
| G37 | iBuN(Me)— | $HO_2C(CH_2)_3N(Me)$— |
| G38 | iBuN(Me)— | $HO_2C(CH_2)_2N(Me)$— |
| G39 | iBuN(Me)— | $HO_2CCH_2N(Me)$— |
| G40 | iBuN(Me)— | $HO_2C(CH_2)_3O$— |
| G41 | iBuN(Me)— | $HO_2C(CH_2)_2O$— |
| G42 | iBuN(Me)— | $HO_2CCH_2O$— |
| G43 | iPrN(Me)— | 4-$HO_2C$-pipe |
| G44 | iPrN(Me)— | 3-$HO_2C$-pipe |
| G45 | iPrN(Me)— | 3-$HO_2C$-pyrr |
| G46 | iPrN(Me)— | 3-$HO_2C$-azet |
| G47 | iPrN(Me)— | 4-$HO_2CCH_2$-pipe |
| G48 | iPrN(Me)— | 4-$HO_2CCH_2$-pipa |

TABLE 34-continued

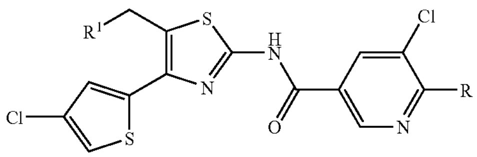

| No | $R^1$ | R |
|---|---|---|
| G49 | iPrN(Me)— | 3-$HO_2CCH_2$-pyrr |
| G50 | iPrN(Me)— | 3-$HO_2CCH_2$-azet |
| G51 | iPrN(Me)— | $HO_2C(CH_2)_3NH$— |
| G52 | iPrN(Me)— | $HO_2C(CH_2)_2NH$— |
| G53 | iPrN(Me)— | $HO_2CCH_2NH$— |
| G54 | iPrN(Me)— | $HO_2C(CH_2)_3N(Me)$— |
| G55 | iPrN(Me)— | $HO_2C(CH_2)_2N(Me)$— |
| G56 | iPrN(Me)— | $HO_2CCH_2N(Me)$— |
| G57 | iPrN(Me)— | $HO_2C(CH_2)_3O$— |
| G58 | iPrN(Me)— | $HO_2C(CH_2)_2O$— |
| G59 | iPrN(Me)— | $HO_2CCH_2O$— |
| G60 | 3-Me-pyrr | $HO_2C(CH_2)_3NH$— |
| G61 | 3-Me-pyrr | $HO_2C(CH_2)_2NH$— |
| G62 | 3-Me-pyrr | $HO_2CCH_2NH$— |
| G63 | 3-Me-pyrr | $HO_2C(CH_2)_3N(Me)$— |
| G64 | 3-Me-pyrr | $HO_2C(CH_2)_2N(Me)$— |
| G65 | 3-Me-pyrr | $HO_2CCH_2N(Me)$— |
| G66 | 3-Me-pyrr | $HO_2C(CH_2)_3O$— |
| G67 | 3-Me-pyrr | $HO_2C(CH_2)_2O$— |
| G68 | 3-Me-pyrr | $HO_2CCH_2O$— |
| G69 | cBuN(Me)— | 4-$HO_2C$-pipe |
| G70 | cBuN(Me)— | 3-$HO_2C$-pipe |
| G71 | cBuN(Me)— | 3-$HO_2C$-pyrr |
| G72 | cBuN(Me)— | 3-$HO_2C$-azet |
| G73 | cBuN(Me)— | 4-$HO_2CCH_2$-pipe |
| G74 | cBuN(Me)— | 4-$HO_2CCH_2$-pipa |
| G75 | cBuN(Me)— | 3-$HO_2CCH_2$-pyrr |
| G76 | cBuN(Me)— | 3-$HO_2CCH_2$-azet |
| G77 | cBuN(Me)— | $HO_2C(CH_2)_3NH$— |
| G78 | cBuN(Me)— | $HO_2C(CH_2)_2NH$— |
| G79 | cBuN(Me)— | $HO_2CCH_2NH$— |
| G80 | cBuN(Me)— | $HO_2C(CH_2)_3N(Me)$— |
| G81 | cBuN(Me)— | $HO_2C(CH_2)_2N(Me)$— |
| G82 | cBuN(Me)— | $HO_2CCH_2N(Me)$— |
| G83 | cBuN(Me)— | $HO_2C(CH_2)_3O$— |
| G84 | cBuN(Me)— | $HO_2C(CH_2)_2O$— |
| G85 | cBuN(Me)— | $HO_2CCH_2O$— |
| G86 | $Me_2N$— | 4-$HO_2C$-pipe |
| G87 | $Me_2N$— | 3-$HO_2C$-pipe |
| G88 | $Me_2N$— | 3-$HO_2C$-pyrr |
| G89 | $Me_2N$— | 3-$HO_2C$-azet |
| G90 | $Me_2N$— | 4-$HO_2CCH_2$-pipe |
| G91 | $Me_2N$— | 4-$HO_2CCH_2$-pipa |
| G92 | $Me_2N$— | 3-$HO_2CCH_2$-pyrr |
| G93 | $Me_2N$— | 3-$HO_2CCH_2$-azet |
| G94 | $Me_2N$— | $HO_2C(CH_2)_3NH$— |
| G95 | $Me_2N$— | $HO_2C(CH_2)_2NH$— |
| G96 | $Me_2N$— | $HO_2CCH_2NH$— |
| G97 | $Me_2N$— | $HO_2C(CH_2)_3N(Me)$— |
| G98 | $Me_2N$— | $HO_2C(CH_2)_2N(Me)$— |
| G99 | $Me_2N$— | $HO_2CCH_2N(Me)$— |
| G100 | $Me_2N$— | $HO_2C(CH_2)_3O$— |
| G101 | $Me_2N$— | $HO_2C(CH_2)_2O$— |
| G102 | $Me_2N$— | $HO_2CCH_2O$— |

TABLE 35

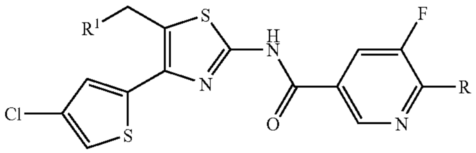

| No | $R^1$ | R |
|---|---|---|
| H1 | 2-Me-pyrr | 4-$HO_2C$-pipe |
| H2 | 2-Me-pyrr | 3-$HO_2C$-pipe |
| H3 | 2-Me-pyrr | 3-$HO_2C$-pyrr |
| H4 | 2-Me-pyrr | 3-$HO_2C$-azet |
| H5 | 2-Me-pyrr | 4-$HO_2CCH_2$-pipe |
| H6 | 2-Me-pyrr | 4-$HO_2CCH_2$-pipa |
| H7 | 2-Me-pyrr | 3-$HO_2CCH_2$-pyrr |
| H8 | 2-Me-pyrr | 3-$HO_2CCH_2$-azet |
| H9 | 2-Me-pyrr | $HO_2C(CH_2)_3NH$— |
| H10 | 2-Me-pyrr | $HO_2C(CH_2)_2NH$— |
| H11 | 2-Me-pyrr | $HO_2CCH_2NH$— |
| H12 | 2-Me-pyrr | $HO_2C(CH_2)_3N(Me)$— |
| H13 | 2-Me-pyrr | $HO_2C(CH_2)_2N(Me)$— |
| H14 | 2-Me-pyrr | $HO_2CCH_2N(Me)$— |
| H15 | 2-Me-pyrr | $HO_2C(CH_2)_3O$— |
| H16 | 2-Me-pyrr | $HO_2C(CH_2)_2O$— |
| H17 | 2-Me-pyrr | $HO_2CCH_2O$— |
| H18 | iBuN(Me)— | 4-$HO_2C$-pipe |
| H19 | iBuN(Me)— | 3-$HO_2C$-pipe |
| H20 | iBuN(Me)— | 3-$HO_2C$-pyrr |
| H21 | iBuN(Me)— | 3-$HO_2C$-azet |
| H22 | iBuN(Me)— | 4-$HO_2CCH_2$-pipe |
| H23 | iBuN(Me)— | 4-$HO_2CCH_2$-pipa |
| H24 | iBuN(Me)— | 3-$HO_2CCH_2$-pyrr |
| H25 | iBuN(Me)— | 3-$HO_2CCH_2$-azet |
| H26 | iBuN(Me)— | $HO_2C(CH_2)_3NH$— |
| H27 | iBuN(Me)— | $HO_2C(CH_2)_2NH$— |
| H28 | iBuN(Me)— | $HO_2CCH_2NH$— |
| H29 | iBuN(Me)— | $HO_2C(CH_2)_3N(Me)$— |
| H30 | iBuN(Me)— | $HO_2C(CH_2)_2N(Me)$— |
| H31 | iBuN(Me)— | $HO_2CCH_2N(Me)$— |
| H32 | iBuN(Me)— | $HO_2C(CH_2)_3O$— |
| H33 | iBuN(Me)— | $HO_2C(CH_2)_2O$— |
| H34 | iBuN(Me)— | $HO_2CCH_2O$— |
| H35 | iPrN(Me)— | 4-$HO_2C$-pipe |
| H36 | iPrN(Me)— | 3-$HO_2C$-pipe |
| H37 | iPrN(Me)— | 3-$HO_2C$-pyrr |
| H38 | iPrN(Me)— | 3-$HO_2C$-azet |
| H39 | iPrN(Me)— | 4-$HO_2CCH_2$-pipe |
| H40 | 3-Me-pyrr | 4-$HO_2C$-pipe |
| H41 | 3-Me-pyrr | 3-$HO_2C$-pipe |
| H42 | 3-Me-pyrr | 3-$HO_2C$-pyrr |
| H43 | 3-Me-pyrr | 3-$HO_2C$-azet |
| H44 | 3-Me-pyrr | 4-$HO_2CCH_2$-pipe |
| H45 | 3-Me-pyrr | 4-$HO_2CCH_2$-pipa |
| H46 | 3-Me-pyrr | 3-$HO_2CCH_2$-pyrr |
| H47 | 3-Me-pyrr | 3-$HO_2CCH_2$-azet |
| H48 | 3-Me-pyrr | $HO_2C(CH_2)_3NH$— |
| H49 | 3-Me-pyrr | $HO_2C(CH_2)_2NH$— |
| H50 | 3-Me-pyrr | $HO_2CCH_2NH$— |
| H51 | 3-Me-pyrr | $HO_2C(CH_2)_3N(Me)$— |
| H52 | 3-Me-pyrr | $HO_2C(CH_2)_2N(Me)$— |
| H53 | 3-Me-pyrr | $HO_2CCH_2N(Me)$— |
| H54 | 3-Me-pyrr | $HO_2C(CH_2)_3O$— |
| H55 | 3-Me-pyrr | $HO_2C(CH_2)_2O$— |
| H56 | 3-Me-pyrr | $HO_2CCH_2O$— |
| H57 | cBuN(Me)— | 4-$HO_2C$-pipe |
| H58 | cBuN(Me)— | 3-$HO_2C$-pipe |
| H59 | cBuN(Me)— | 3-$HO_2C$-pyrr |
| H60 | cBuN(Me)— | 3-$HO_2C$-azet |
| H61 | cBuN(Me)— | 4-$HO_2CCH_2$-pipe |
| H62 | cBuN(Me)— | 4-$HO_2CCH_2$-pipa |
| H63 | cBuN(Me)— | 3-$HO_2CCH_2$-pyrr |
| H64 | cBuN(Me)— | 3-$HO_2CCH_2$-azet |
| H65 | cBuN(Me)— | $HO_2C(CH_2)_3NH$— |
| H66 | cBuN(Me)— | $HO_2C(CH_2)_2NH$— |
| H67 | cBuN(Me)— | $HO_2CCH_2NH$— |
| H68 | cBuN(Me)— | $HO_2C(CH_2)_3N(Me)$— |

TABLE 35-continued

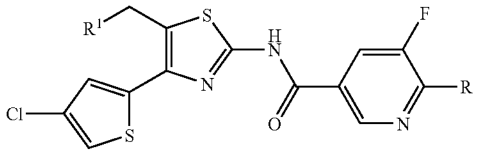

| No | $R^1$ | R |
|---|---|---|
| H69 | cBuN(Me)— | $HO_2C(CH_2)_2N(Me)$— |
| H70 | cBuN(Me)— | $HO_2CCH_2N(Me)$— |
| H71 | cBuN(Me)— | $HO_2C(CH_2)_3O$— |
| H72 | cBuN(Me)— | $HO_2C(CH_2)_2O$— |
| H73 | cBuN(Me)— | $HO_2CCH_2O$— |
| H74 | $Me_2N$— | 4-$HO_2C$-pipe |
| H75 | $Me_2N$— | 3-$HO_2C$-pipe |
| H76 | $Me_2N$— | 3-$HO_2C$-pyrr |
| H77 | $Me_2N$— | 3-$HO_2C$-azet |
| H78 | $Me_2N$— | 4-$HO_2CCH_2$-pipe |
| H79 | iPrN(Me)— | 4-$HO_2CCH_2$-pipa |
| H80 | iPrN(Me)— | 3-$HO_2CCH_2$-pyrr |
| H81 | iPrN(Me)— | 3-$HO_2CCH_2$-azet |
| H82 | iPrN(Me)— | $HO_2C(CH_2)_3NH$— |
| H83 | iPrN(Me)— | $HO_2C(CH_2)_2NH$— |
| H84 | iPrN(Me)— | $HO_2CCH_2NH$— |
| H85 | iPrN(Me)— | $HO_2C(CH_2)_3N(Me)$— |
| H86 | iPrN(Me)— | $HO_2C(CH_2)_2N(Me)$— |
| H87 | iPrN(Me)— | $HO_2CCH_2N(Me)$— |
| H88 | iPrN(Me)— | $HO_2C(CH_2)_3O$— |
| H89 | iPrN(Me)— | $HO_2C(CH_2)_2O$— |
| H90 | iPrN(Me)— | $HO_2CCH_2O$— |
| H91 | $Me_2N$— | 4-$HO_2CCH_2$-pipa |
| H92 | $Me_2N$— | 3-$HO_2CCH_2$-pyrr |
| H93 | $Me_2N$— | 3-$HO_2CCH_2$-azet |
| H94 | $Me_2N$— | $HO_2C(CH_2)_3NH$— |
| H95 | $Me_2N$— | $HO_2C(CH_2)_2NH$— |
| H96 | $Me_2N$— | $HO_2CCH_2NH$— |
| H97 | $Me_2N$— | $HO_2C(CH_2)_3N(Me)$— |
| H98 | $Me_2N$— | $HO_2C(CH_2)_2N(Me)$— |
| H99 | $Me_2N$— | $HO_2CCH_2N(Me)$— |
| H100 | $Me_2N$— | $HO_2C(CH_2)_3O$— |
| H101 | $Me_2N$— | $HO_2C(CH_2)_2O$— |
| H102 | $Me_2N$— | $HO_2CCH_2O$— |

TABLE 36

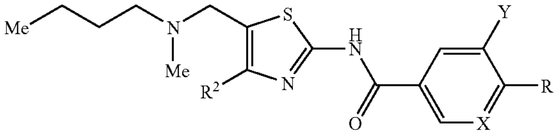

| No | $R^2$ | X | Y | R |
|---|---|---|---|---|
| I1 | 4-Cl-2-The | N | Cl | 4-HO$(CH_2)_2$-pipe |
| I2 | 4-Cl-2-The | N | Cl | 4-MeO-pipe |
| I3 | 4-Cl-2-The | N | Cl | $MeO(CH_2)_3O$— |
| I4 | 4-Cl-2-The | N | Cl | $MeO(CH_2)_2O$— |
| I5 | 4-Cl-2-The | N | Cl | $H_2O_3P$—$(CH_2)_3NH$— |
| I6 | 4-Cl-2-The | N | Cl | 4-$H_2O_3P$-pipe |
| I7 | 4-Cl-2-The | N | Cl | $(EtO)_2(O)P$—$(CH_2)_3NH$— |
| I8 | 4-Cl-2-The | N | Cl | 4-$(EtO)_2(O)P$-pipe |
| I9 | 4-Cl-2-The | N | Cl | 4-NC-pipe |
| I10 | 4-Cl-2-The | N | Cl | 3-oxo-pipa |
| I11 | 4-Cl-2-The | C—H | Cl | 4-HO-pipe |
| I12 | 4-Cl-2-The | C—H | Cl | 4-$HOCH_2$-pipe |
| I13 | 4-Cl-2-The | C—H | Cl | 4-HO$(CH_2)_2$-pipe |
| I14 | 4-Cl-2-The | C—H | Cl | 4-MeO-pipe |
| I15 | 4-Cl-2-The | C—H | Cl | $MeO(CH_2)_3O$— |
| I16 | 4-Cl-2-The | C—H | Cl | $MeO(CH_2)_2O$— |
| I17 | 4-Cl-2-The | C—H | Cl | $H_2O_3P$—$(CH_2)_3NH$— |
| I18 | 4-Cl-2-The | C—H | Cl | 4-$H_2O_3P$-pipe |
| I19 | 4-Cl-2-The | C—H | Cl | $(EtO)_2(O)P$—$(CH_2)_3NH$— |
| I20 | 4-Cl-2-The | C—H | Cl | 4-$(EtO)_2(O)P$-pipe |

TABLE 36-continued

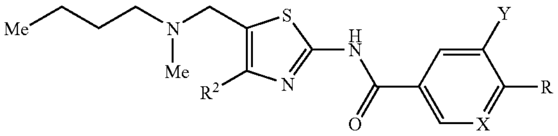

| No | $R^2$ | X | Y | R |
|---|---|---|---|---|
| I21 | 4-Cl-2-The | C—H | Cl | 4-NC-pipe |
| I22 | 4-Cl-2-The | C—H | Cl | 3-oxo-pipa |
| I23 | 4-Cl-2-The | C—F | F | 4-HO-pipe |
| I24 | 4-Cl-2-The | C—F | F | 4-$HOCH_2$-pipe |
| I25 | 4-Cl-2-The | C—F | F | 4-HO$(CH_2)_2$-pipe |
| I26 | 4-Cl-2-The | C—F | F | 4-MeO-pipe |
| I27 | 4-Cl-2-The | C—F | F | $MeO(CH_2)_3O$— |
| I28 | 4-Cl-2-The | C—F | F | $MeO(CH_2)_2O$— |
| I29 | 4-Cl-2-The | C—F | F | $H_2O_3P$—$(CH_2)_3NH$— |
| I30 | 4-Cl-2-The | C—F | F | 4-$H_2O_3P$-pipe |
| I31 | 4-Cl-2-The | C—F | F | $(EtO)_2(O)P$—$(CH_2)_3NH$— |
| I32 | 4-Cl-2-The | C—F | F | 4-$(EtO)_2(O)P$-pipe |
| I33 | 4-Cl-2-The | C—F | F | 4-NC-pipe |
| I34 | 4-Cl-2-The | C—F | F | 3-oxo-pipa |
| I35 | 4-Me-2-The | N | Cl | $HO(CH_2)_3NH$— |
| I36 | 4-Me-2-The | N | Cl | $HO(CH_2)_3N(Me)$— |
| I37 | 4-Me-2-The | N | Cl | $HO(CH_2)_3O$— |
| I38 | 4-Me-2-The | N | Cl | $HO(CH_2)_2O$— |
| I39 | 4-Me-2-The | N | Cl | 4-HO-pipe |
| I40 | 4-Me-2-The | N | Cl | 4-$HOCH_2$-pipe |
| I41 | 4-Me-2-The | N | Cl | 4-HO$(CH_2)_2$-pipe |
| I42 | 4-Me-2-The | N | Cl | 4-MeO-pipe |
| I43 | 4-Me-2-The | N | Cl | $MeO(CH_2)_3O$— |
| I44 | 4-Me-2-The | N | Cl | $MeO(CH_2)_2O$— |
| I45 | 4-Me-2-The | N | Cl | $H_2O_3P$—$(CH_2)_3NH$— |
| I46 | 4-Me-2-The | N | Cl | 4-$H_2O_3P$-pipe |
| I47 | 4-Me-2-The | N | Cl | $(EtO)_2(O)P$—$(CH_2)_3NH$— |
| I48 | 4-Me-2-The | N | Cl | 4-$(EtO)_2(O)P$-pipe |
| I49 | 4-Me-2-The | N | Cl | 4-NC-pipe |
| I50 | 4-Me-2-The | N | Cl | 3-oxo-pipa |
| I51 | 4-Me-2-The | C—H | Cl | $HO(CH_2)_3NH$— |
| I52 | 4-Me-2-The | C—H | Cl | $HO(CH_2)_3N(Me)$— |
| I53 | 4-Me-2-The | C—H | Cl | $HO(CH_2)_3O$— |
| I54 | 4-Me-2-The | C—H | Cl | $HO(CH_2)_2O$— |
| I55 | 4-Me-2-The | C—H | Cl | 4-HO-pipe |
| I56 | 4-Me-2-The | C—H | Cl | 4-$HOCH_2$-pipe |
| I57 | 4-Me-2-The | C—H | Cl | 4-HO$(CH_2)_2$-pipe |
| I58 | 4-Me-2-The | C—H | Cl | 4-MeO-pipe |
| I59 | 4-Me-2-The | C—H | Cl | $MeO(CH_2)_3O$— |
| I60 | 4-Me-2-The | C—H | Cl | $MeO(CH_2)_2O$— |
| I61 | 4-Me-2-The | C—H | Cl | $H_2O_3P$—$(CH_2)_3NH$— |
| I62 | 4-Me-2-The | C—H | Cl | 4-$H_2O_3P$-pipe |
| I63 | 4-Me-2-The | C—H | Cl | $(EtO)_2(O)P$—$(CH_2)_3NH$— |
| I64 | 4-Me-2-The | C—H | Cl | 4-$(EtO)_2(O)P$-pipe |
| I65 | 4-Me-2-The | C—H | Cl | 4-NC-pipe |
| I66 | 4-Me-2-The | C—H | Cl | 3-oxo-pipa |
| I67 | 4-Me-2-The | C—F | F | $HO(CH_2)_3NH$— |
| I68 | 4-Me-2-The | C—F | F | $HO(CH_2)_3N(Me)$— |
| I69 | 4-Me-2-The | C—F | F | $HO(CH_2)_3O$— |
| I70 | 4-Me-2-The | C—F | F | $HO(CH_2)_2O$— |
| I71 | 4-Me-2-The | C—F | F | 4-HO-pipe |
| I72 | 4-Me-2-The | C—F | F | 4-$HOCH_2$-pipe |
| I73 | 4-Me-2-The | C—F | F | 4-HO$(CH_2)_2$-pipe |
| I74 | 4-Me-2-The | C—F | F | 4-MeO-pipe |
| I75 | 4-Me-2-The | C—F | F | $MeO(CH_2)_3O$— |
| I76 | 4-Me-2-The | C—F | F | $MeO(CH_2)_2O$— |
| I77 | 4-Me-2-The | C—F | F | $H_2O_3P$—$(CH_2)_3NH$— |
| I78 | 4-Me-2-The | C—F | F | 4-$H_2O_3P$-pipe |
| I79 | 4-Me-2-The | C—F | F | $(EtO)_2(O)P$-$(CH_2)_3NH$— |
| I80 | 4-Me-2-The | C—F | F | 4-$(EtO)_2(O)P$-pipe |
| I81 | 4-Me-2-The | C—F | F | 4-NC-pipe |
| I82 | 4-Me-2-The | C—F | F | 3-oxo-pipa |
| I83 | 3-$F_3C$-Ph | N | Cl | $HO(CH_2)_3NH$— |
| I84 | 3-$F_3C$-Ph | N | Cl | $HO(CH_2)_3N(Me)$— |
| I85 | 3-$F_3C$-Ph | N | Cl | $HO(CH_2)_3O$— |
| I86 | 3-$F_3C$-Ph | N | Cl | $HO(CH_2)_2O$— |
| I87 | 3-$F_3C$-Ph | N | Cl | 4-HO-pipe |
| I88 | 3-$F_3C$-Ph | N | Cl | 4-$HOCH_2$-pipe |
| I89 | 3-$F_3C$-Ph | N | Cl | 4-HO$(CH_2)_2$-pipe |

TABLE 36-continued

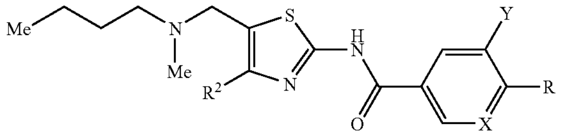

| No | $R^2$ | X | Y | R |
|---|---|---|---|---|
| I90 | 3-$F_3$C-Ph | N | Cl | 4-MeO-pipe |
| I91 | 3-$F_3$C-Ph | N | Cl | MeO$(CH_2)_3$O— |
| I92 | 3-$F_3$C-Ph | N | Cl | MeO$(CH_2)_2$O— |
| I93 | 3-$F_3$C-Ph | N | Cl | $H_2O_3$P—$(CH_2)_3$NH— |
| I94 | 3-$F_3$C-Ph | N | Cl | 4-$H_2O_3$P-pipe |
| I95 | 3-$F_3$C-Ph | N | Cl | $(EtO)_2$(O)P-$(CH_2)_3$NH— |
| I96 | 3-$F_3$C-Ph | N | Cl | 4-$(EtO)_2$(O)P-pipe |
| I97 | 3-$F_3$C-Ph | N | Cl | 4-NC-pipe |
| I98 | 3-$F_3$C-Ph | N | Cl | 3-oxo-pipa |
| I99 | 3-$F_3$C-Ph | C—H | Cl | HO$(CH_2)_3$NH— |
| I100 | 3-$F_3$C-Ph | C—H | Cl | HO$(CH_2)_3$N(Me)— |
| I101 | 3-$F_3$C-Ph | C—H | Cl | HO$(CH_2)_3$O— |
| I102 | 3-$F_3$C-Ph | C—H | Cl | HO$(CH_2)_2$O— |
| I103 | 3-$F_3$C-Ph | C—H | Cl | 4-HO-pipe |
| I104 | 3-$F_3$C-Ph | C—H | Cl | 4-$HOCH_2$-pipe |
| I105 | 3-$F_3$C-Ph | C—H | Cl | 4-HO$(CH_2)_2$-pipe |
| I106 | 3-$F_3$C-Ph | C—H | Cl | 4-MeO-pipe |
| I107 | 3-$F_3$C-Ph | C—H | Cl | MeO$(CH_2)_3$O— |
| I108 | 3-$F_3$C-Ph | C—H | Cl | MeO$(CH_2)_2$O— |
| I109 | 3-$F_3$C-Ph | C—H | Cl | $H_2O_3$P—$(CH_2)_3$NH— |
| I110 | 3-$F_3$C-Ph | C—H | Cl | 4-$H_2O_3$P-pipe |
| I111 | 3-$F_3$C-Ph | C—H | Cl | $(EtO)_2$(O)P—$(CH_2)_3$NH— |
| I112 | 3-$F_3$C-Ph | C—H | Cl | 4-$(EtO)_2$(O)P-pipe |
| I113 | 3-$F_3$C-Ph | C—H | Cl | 4-NC-pipe |
| I114 | 3-$F_3$C-Ph | C—H | Cl | 3-oxo-pipa |
| I115 | 3-$F_3$C-Ph | C—F | F | HO$(CH_2)_3$NH— |
| I116 | 3-$F_3$C-Ph | C—F | F | HO$(CH_2)_3$N(Me)— |
| I117 | 3-$F_3$C-Ph | C—F | F | HO$(CH_2)_3$O— |
| I118 | 3-$F_3$C-Ph | C—F | F | HO$(CH_2)_2$O— |
| I119 | 3-$F_3$C-Ph | C—F | F | 4-HO-pipe |
| I120 | 3-$F_3$C-Ph | C—F | F | 4-$HOCH_2$-pipe |
| I121 | 3-$F_3$C-Ph | C—F | F | 4-HO$(CH_2)_2$-pipe |
| I122 | 3-$F_3$C-Ph | C—F | F | 4-MeO-pipe |
| I123 | 3-$F_3$C-Ph | C—F | F | MeO$(CH_2)_3$O— |
| I124 | 3-$F_3$C-Ph | C—F | F | MeO$(CH_2)_2$O— |
| I125 | 3-$F_3$C-Ph | C—F | F | $H_2O_3$P—$(CH_2)_3$NH— |
| I126 | 3-$F_3$C-Ph | C—F | F | 4-$H_2O_3$P-pipe |
| I127 | 3-$F_3$C-Ph | C—F | F | $(EtO)_2$(O)P—$(CH_2)_3$NH— |
| I128 | 3-$F_3$C-Ph | C—F | F | 4-$(EtO)_2$(O)P-pipe |
| I129 | 3-$F_3$C-Ph | C—F | F | 4-NC-pipe |
| I130 | 3-$F_3$C-Ph | C—F | F | 3-oxo-pipa |

TABLE 37

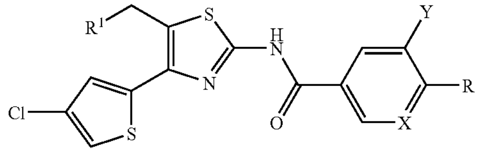

| No | $R^1$ | X | Y | R |
|---|---|---|---|---|
| J1 | cBuN(Me)— | N | Cl | HO$(CH_2)_3$NH— |
| J2 | cBuN(Me)— | N | Cl | HO$(CH_2)_3$N(Me)— |
| J3 | cBuN(Me)— | N | Cl | HO$(CH_2)_3$O— |
| J4 | cBuN(Me)— | N | Cl | HO$(CH_2)_2$O— |
| J5 | cBuN(Me)— | N | Cl | 4-HO-pipe |
| J6 | cBuN(Me)— | N | Cl | 4-$HOCH_2$-pipe |
| J7 | cBuN(Me)— | N | Cl | 4-HO$(CH_2)_2$-pipe |
| J8 | cBuN(Me)— | N | Cl | 4-MeO-pipe |
| J9 | cBuN(Me)— | N | Cl | MeO$(CH_2)_3$O— |
| J10 | cBuN(Me)— | N | Cl | MeO$(CH_2)_2$O— |
| J11 | cBuN(Me)— | N | Cl | $H_2O_3$P—$(CH_2)_3$NH— |
| J12 | cBuN(Me)— | N | Cl | 4-$H_2O_3$P-pipe |
| J13 | cBuN(Me)— | N | Cl | $(EtO)_2$(O)P—$(CH_2)_3$NH— |

TABLE 37-continued

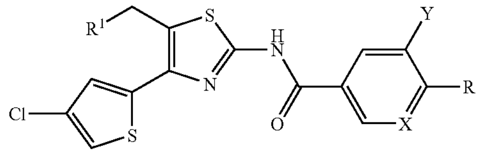

| No | $R^1$ | X | Y | R |
|---|---|---|---|---|
| J14 | cBuN(Me)— | N | Cl | 4-$(EtO)_2$(O)P-pipe |
| J15 | cBuN(Me)— | N | Cl | 4-NC-pipe |
| J16 | cBuN(Me)— | N | Cl | 3-oxo-pipa |
| J17 | cBuN(Me)— | C—H | Cl | HO$(CH_2)_3$NH— |
| J18 | cBuN(Me)— | C—H | Cl | HO$(CH_2)_3$N(Me)— |
| J19 | cBuN(Me)— | C—H | Cl | HO$(CH_2)_3$O— |
| J20 | cBuN(Me)— | C—H | Cl | HO$(CH_2)_2$O— |
| J21 | cBuN(Me)— | C—H | Cl | 4-HO-pipe |
| J22 | cBuN(Me)— | C—H | Cl | 4-$HOCH_2$-pipe |
| J23 | cBuN(Me)— | C—H | Cl | 4-HO$(CH_2)_2$-pipe |
| J24 | cBuN(Me)— | C—H | Cl | 4-MeO-pipe |
| J25 | cBuN(Me)— | C—H | Cl | MeO$(CH_2)_3$O— |
| J26 | cBuN(Me)— | C—H | Cl | MeO$(CH_2)_2$O— |
| J27 | cBuN(Me)— | C—H | Cl | $H_2O_3$P—$(CH_2)_3$NH— |
| J28 | cBuN(Me)— | C—H | Cl | 4-$H_2O_3$P-pipe |
| J29 | cBuN(Me)— | C—H | Cl | $(EtO)_2$(O)P—$(CH_2)_3$NH— |
| J30 | cBuN(Me)— | C—H | Cl | 4-$(EtO)_2$(O)P-pipe |
| J31 | cBuN(Me)— | C—H | Cl | 4-NC-pipe |
| J32 | cBuN(Me)— | C—H | Cl | 3-oxo-pipa |
| J33 | iBuN(Me)— | N | Cl | HO$(CH_2)_3$NH— |
| J34 | iBuN(Me)— | N | Cl | HO$(CH_2)_3$N(Me)— |
| J35 | iBuN(Me)— | N | Cl | HO$(CH_2)_3$O— |
| J36 | iBuN(Me)— | N | Cl | HO$(CH_2)_2$O— |
| J37 | iBuN(Me)— | N | Cl | 4-HO-pipe |
| J38 | iBuN(Me)— | N | Cl | 4-$HOCH_2$-pipe |
| J39 | iBuN(Me)— | N | Cl | 4-HO$(CH_2)_2$-pipe |
| J40 | iBuN(Me)— | N | Cl | 4-MeO-pipe |
| J41 | iBuN(Me)— | N | Cl | MeO$(CH_2)_3$O— |
| J42 | iBuN(Me)— | N | Cl | MeO$(CH_2)_2$O— |
| J43 | iBuN(Me)— | N | Cl | $H_2O_3$P—$(CH_2)_3$NH— |
| J44 | iBuN(Me)— | N | Cl | 4-$H_2O_3$P-pipe |
| J45 | iBuN(Me)— | N | Cl | $(EtO)_2$(O)P—$(CH_2)_3$NH— |
| J46 | iBuN(Me)— | N | Cl | 4-$(EtO)_2$(O)P-pipe |
| J47 | iBuN(Me)— | N | Cl | 4-NC-pipe |
| J48 | iBuN(Me)— | N | Cl | 3-oxo-pipa |
| J49 | iBuN(Me)— | C—H | Cl | HO$(CH_2)_3$NH— |
| J50 | iBuN(Me)— | C—H | Cl | HO$(CH_2)_3$N(Me)— |
| J51 | iBuN(Me)— | C—H | Cl | HO$(CH_2)_3$O— |
| J52 | iBuN(Me)— | C—H | Cl | HO$(CH_2)_2$O— |
| J53 | iBuN(Me)— | C—H | Cl | 4-HO-pipe |
| J54 | iBuN(Me)— | C—H | Cl | 4-$HOCH_2$-pipe |
| J55 | iBuN(Me)— | C—H | Cl | 4-HO$(CH_2)_2$-pipe |
| J56 | iBuN(Me)— | C—H | Cl | 4-MeO-pipe |
| J57 | iBuN(Me)— | C—H | Cl | MeO$(CH_2)_3$O— |
| J58 | iBuN(Me)— | C—H | Cl | MeO$(CH_2)_2$O— |
| J59 | iBuN(Me)— | C—H | Cl | $H_2O_3$P—$(CH_2)_3$NH— |
| J60 | iBuN(Me)— | C—H | Cl | 4-$H_2O_3$P-pipe |
| J61 | iBuN(Me)— | C—H | Cl | $(EtO)_2$(O)P—$(CH_2)_3$NH— |
| J62 | iBuN(Me)— | C—H | Cl | 4-$(EtO)_2$(O)P-pipe |
| J63 | iBuN(Me)— | C—H | Cl | 4-NC-pipe |
| J64 | iBuN(Me)— | C—H | Cl | 3-oxo-pipa |
| J65 | pipe | N | Cl | HO$(CH_2)_3$NH— |
| J66 | pipe | N | Cl | HO$(CH_2)_3$N(Me)— |
| J67 | pipe | N | Cl | HO$(CH_2)_3$O— |
| J68 | pipe | N | Cl | HO$(CH_2)_2$O— |
| J69 | pipe | N | Cl | 4-HO-pipe |
| J70 | pipe | N | Cl | 4-$HOCH_2$-pipe |
| J71 | pipe | N | Cl | 4-HO$(CH_2)_2$-pipe |
| J72 | pipe | N | Cl | 4-MeO-pipe |
| J73 | pipe | N | Cl | MeO$(CH_2)_3$O— |
| J74 | pipe | N | Cl | MeO$(CH_2)_2$O— |
| J75 | pipe | N | Cl | $H_2O_3$P—$(CH_2)_3$NH— |
| J76 | pipe | N | Cl | 4-$H_2O_3$P-pipe |
| J77 | pipe | N | Cl | $(EtO)_2$(O)P—$(CH_2)_3$NH— |
| J78 | pipe | N | Cl | 4-$(EtO)_2$(O)P-pipe |
| J79 | pipe | N | Cl | 4-NC-pipe |
| J80 | pipe | N | Cl | 3-oxo-pipa |
| J81 | pipe | C—H | Cl | HO$(CH_2)_3$NH— |

TABLE 37-continued

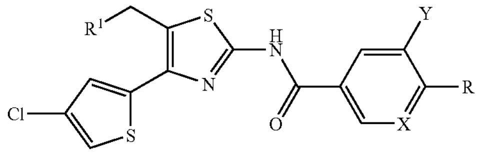

| No | $R^1$ | X | Y | R |
|---|---|---|---|---|
| J82 | pipe | C—H | Cl | $HO(CH_2)_3N(Me)$— |
| J83 | pipe | C—H | Cl | $HO(CH_2)_3O$— |
| J84 | pipe | C—H | Cl | $HO(CH_2)_2O$— |
| J85 | pipe | C—H | Cl | 4-HO-pipe |
| J86 | pipe | C—H | Cl | 4-$HOCH_2$-pipe |
| J87 | pipe | C—H | Cl | 4-$HO(CH_2)_2$-pipe |
| J88 | pipe | C—H | Cl | 4-MeO-pipe |
| J89 | pipe | C—H | Cl | $MeO(CH_2)_3O$— |
| J90 | pipe | C—H | Cl | $MeO(CH_2)_2O$— |
| J91 | pipe | C—H | Cl | $H_2O_3P$—$(CH_2)_3NH$— |
| J92 | pipe | C—H | Cl | 4-$H_2O_3P$-pipe |
| J93 | pipe | C—H | Cl | $(EtO)_2(O)P$—$(CH_2)_3NH$— |
| J94 | pipe | C—H | Cl | 4-$(EtO)_2(O)P$-pipe |
| J95 | pipe | C—H | Cl | 4-NC-pipe |
| J96 | pipe | C—H | Cl | 3-oxo-pipa |
| J97 | 2-Me-pyrr | N | Cl | $HO(CH_2)_3NH$— |
| J98 | 2-Me-pyrr | N | Cl | $HO(CH_2)_3N(Me)$— |
| J99 | 2-Me-pyrr | N | Cl | $HO(CH_2)_3O$— |
| J100 | 2-Me-pyrr | N | Cl | $HO(CH_2)_2O$— |
| J101 | 2-Me-pyrr | N | Cl | 4-HO-pipe |
| J102 | 2-Me-pyrr | N | Cl | 4-$HOCH_2$-pipe |
| J103 | 2-Me-pyrr | N | Cl | 4-$HO(CH_2)_2$-pipe |
| J104 | 2-Me-pyrr | N | Cl | 4-MeO-pipe |
| J105 | 2-Me-pyrr | N | Cl | $MeO(CH_2)_3O$— |
| J106 | 2-Me-pyrr | N | Cl | $MeO(CH_2)_2O$— |
| J107 | 2-Me-pyrr | N | Cl | $H_2O_3P$—$(CH_2)_3NH$— |
| J108 | 2-Me-pyrr | N | Cl | 4-$H_2O_3P$-pipe |
| J109 | 2-Me-pyrr | N | Cl | $(EtO)_2(O)P$—$(CH_2)_3NH$— |
| J110 | 2-Me-pyrr | N | Cl | 4-$(EtO)_2(O)P$-pipe |
| J111 | 2-Me-pyrr | N | Cl | 4-NC-pipe |
| J112 | 2-Me-pyrr | N | Cl | 3-oxo-pipa |
| J113 | 2-Me-pyrr | C—H | Cl | $HO(CH_2)_3NH$— |
| J114 | 2-Me-pyrr | C—H | Cl | $HO(CH_2)_3N(Me)$— |
| J115 | 2-Me-pyrr | C—H | Cl | $HO(CH_2)_3O$— |
| J116 | 2-Me-pyrr | C—H | Cl | $HO(CH_2)_2O$— |
| J117 | 2-Me-pyrr | C—H | Cl | 4-HO-pipe |
| J118 | 2-Me-pyrr | C—H | Cl | 4-$HOCH_2$-pipe |
| J119 | 2-Me-pyrr | C—H | Cl | 4-$HO(CH_2)_2$-pipe |
| J120 | 2-Me-pyrr | C—H | Cl | 4-MeO-pipe |
| J121 | 2-Me-pyrr | C—H | Cl | $MeO(CH_2)_3O$— |
| J122 | 2-Me-pyrr | C—H | Cl | $MeO(CH_2)_2O$— |
| J123 | 2-Me-pyrr | C—H | Cl | $H_2O_3P$—$(CH_2)_3NH$— |
| J124 | 2-Me-pyrr | C—H | Cl | 4-$H_2O_3P$-pipe |
| J125 | 2-Me-pyrr | C—H | Cl | $(EtO)_2(O)P$—$(CH_2)_3NH$— |
| J126 | 2-Me-pyrr | C—H | Cl | 4-$(EtO)_2(O)P$-pipe |
| J127 | 2-Me-pyrr | C—H | Cl | 4-NC-pipe |
| J128 | 2-Me-pyrr | C—H | Cl | 3-oxo-pipa |
| J129 | 3-Me-pyrr | N | Cl | $HO(CH_2)_3NH$— |
| J130 | 3-Me-pyrr | N | Cl | $HO(CH_2)_3N(Me)$— |
| J131 | 3-Me-pyrr | N | Cl | $HO(CH_2)_3O$— |
| J132 | 3-Me-pyrr | N | Cl | $HO(CH_2)_2O$— |
| J133 | 3-Me-pyrr | N | Cl | 4-HO-pipe |
| J134 | 3-Me-pyrr | N | Cl | 4-$HOCH_2$-pipe |
| J135 | 3-Me-pyrr | N | Cl | 4-$HO(CH_2)_2$-pipe |
| J136 | 3-Me-pyrr | N | Cl | 4-MeO-pipe |
| J137 | 3-Me-pyrr | N | Cl | $MeO(CH_2)_3O$— |
| J138 | 3-Me-pyrr | N | Cl | $MeO(CH_2)_2O$— |
| J139 | 3-Me-pyrr | N | Cl | $H_2O_3P$—$(CH_2)_3NH$— |
| J140 | 3-Me-pyrr | N | Cl | 4-$H_2O_3P$-pipe |
| J141 | 3-Me-pyrr | N | Cl | $(EtO)_2(O)P$—$(CH_2)_3NH$— |
| J142 | 3-Me-pyrr | N | Cl | 4-$(EtO)_2(O)P$-pipe |
| J143 | 3-Me-pyrr | N | Cl | 4-NC-pipe |
| J144 | 3-Me-pyrr | N | Cl | 3-oxo-pipa |
| J145 | 3-Me-pyrr | C—H | Cl | $HO(CH_2)_3NH$— |
| J146 | 3-Me-pyrr | C—H | Cl | $HO(CH_2)_3N(Me)$— |
| J147 | 3-Me-pyrr | C—H | Cl | $HO(CH_2)_3O$— |
| J148 | 3-Me-pyrr | C—H | Cl | $HO(CH_2)_2O$— |
| J149 | 3-Me-pyrr | C—H | Cl | 4-HO-pipe |

TABLE 37-continued

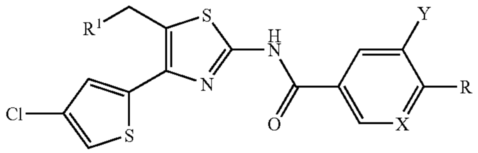

| No | $R^1$ | X | Y | R |
|---|---|---|---|---|
| J150 | 3-Me-pyrr | C—H | Cl | 4-$HOCH_2$-pipe |
| J151 | 3-Me-pyrr | C—H | Cl | 4-$HO(CH_2)_2$-pipe |
| J152 | 3-Me-pyrr | C—H | Cl | 4-MeO-pipe |
| J153 | 3-Me-pyrr | C—H | Cl | $MeO(CH_2)_3O$— |
| J154 | 3-Me-pyrr | C—H | Cl | $MeO(CH_2)_2O$— |
| J155 | 3-Me-pyrr | C—H | Cl | $H_2O_3P$—$(CH_2)_3NH$— |
| J156 | 3-Me-pyrr | C—H | Cl | 4-$H_2O_3P$-pipe |
| J157 | 3-Me-pyrr | C—H | Cl | $(EtO)_2(O)P$—$(CH_2)_3NH$— |
| J158 | 3-Me-pyrr | C—H | Cl | 4-$(EtO)_2(O)P$-pipe |
| J159 | 3-Me-pyrr | C—H | Cl | 4-NC-pipe |
| J160 | 3-Me-pyrr | C—H | Cl | 3-oxo-pipa |
| J161 | iPrN(Me)— | N | Cl | $HO(CH_2)_3NH$— |
| J162 | iPrN(Me)— | N | Cl | $HO(CH_2)_3N(Me)$— |
| J163 | iPrN(Me)— | N | Cl | $HO(CH_2)_3O$— |
| J164 | iPrN(Me)— | N | Cl | $HO(CH_2)_2O$— |
| J165 | iPrN(Me)— | N | Cl | 4-HO-pipe |
| J166 | iPrN(Me)— | N | Cl | 4-$HOCH_2$-pipe |
| J167 | iPrN(Me)— | N | Cl | 4-$HO(CH_2)_2$-pipe |
| J168 | iPrN(Me)— | N | Cl | 4-MeO-pipe |
| J169 | iPrN(Me)— | N | Cl | $MeO(CH_2)_3O$— |
| J170 | iPrN(Me)— | N | Cl | $MeO(CH_2)_2O$— |
| J171 | iPrN(Me)— | N | Cl | $H_2O_3P$—$(CH_2)_3NH$— |
| J172 | iPrN(Me)— | N | Cl | 4-$H_2O_3P$-pipe |
| J173 | iPrN(Me)— | N | Cl | $(EtO)_2(O)P$—$(CH_2)_3NH$— |
| J174 | iPrN(Me)— | N | Cl | 4-$(EtO)_2(O)P$-pipe |
| J175 | iPrN(Me)— | N | Cl | 4-NC-pipe |
| J176 | iPrN(Me)— | N | Cl | 3-oxo-pipa |
| J177 | iPrN(Me)— | C—H | Cl | $HO(CH_2)_3NH$— |
| J178 | iPrN(Me)— | C—H | Cl | $HO(CH_2)_3N(Me)$— |
| J179 | iPrN(Me)— | C—H | Cl | $HO(CH_2)_3O$— |
| J180 | iPrN(Me)— | C—H | Cl | $HO(CH_2)_2O$— |
| J181 | iPrN(Me)— | C—H | Cl | 4-HO-pipe |
| J182 | iPrN(Me)— | C—H | Cl | 4-$HOCH_2$-pipe |
| J183 | iPrN(Me)— | C—H | Cl | 4-$HO(CH_2)_2$-pipe |
| J184 | iPrN(Me)— | C—H | Cl | 4-MeO-pipe |
| J185 | iPrN(Me)— | C—H | Cl | $MeO(CH_2)_3O$— |
| J186 | iPrN(Me)— | C—H | Cl | $MeO(CH_2)_2O$— |
| J187 | iPrN(Me)— | C—H | Cl | $H_2O_3P$—$(CH_2)_3NH$— |
| J188 | iPrN(Me)— | C—H | Cl | 4-$H_2O_3P$-pipe |
| J189 | iPrN(Me)— | C—H | Cl | $(EtO)_2(O)P$—$(CH_2)_3NH$— |
| J190 | iPrN(Me)— | C—H | Cl | 4-$(EtO)_2(O)P$-pipe |
| J191 | iPrN(Me)— | C—H | Cl | 4-NC-pipe |
| J192 | iPrN(Me)— | C—H | Cl | 3-oxo-pipa |
| J193 | $Me_2N$— | N | Cl | $HO(CH_2)_3NH$— |
| J194 | $Me_2N$— | N | Cl | $HO(CH_2)_3N(Me)$— |
| J195 | $Me_2N$— | N | Cl | $HO(CH_2)_3O$— |
| J196 | $Me_2N$— | N | Cl | $HO(CH_2)_2O$— |
| J197 | $Me_2N$— | N | Cl | 4-HO-pipe |
| J198 | $Me_2N$— | N | Cl | 4-$HOCH_2$-pipe |
| J199 | $Me_2N$— | N | Cl | 4-$HO(CH_2)_2$-pipe |
| J200 | $Me_2N$— | N | Cl | 4-MeO-pipe |
| J201 | $Me_2N$— | N | Cl | $MeO(CH_2)_3O$— |
| J202 | $Me_2N$— | N | Cl | $MeO(CH_2)_2O$— |
| J203 | $Me_2N$— | N | Cl | $H_2O_3P$—$(CH_2)_3NH$— |
| J204 | $Me_2N$— | N | Cl | 4-$H_2O_3P$-pipe |
| J205 | $Me_2N$— | N | Cl | $(EtO)_2(O)P$—$(CH_2)_3NH$— |
| J206 | $Me_2N$— | N | Cl | 4-$(EtO)_2(O)P$-pipe |
| J207 | $Me_2N$— | N | Cl | 4-NC-pipe |
| J208 | $Me_2N$— | N | Cl | 3-oxo-pipa |
| J209 | $Me_2N$— | C—H | Cl | $HO(CH_2)_3NH$— |
| J210 | $Me_2N$— | C—H | Cl | $HO(CH_2)_3N(Me)$— |
| J211 | $Me_2N$— | C—H | Cl | $HO(CH_2)_3O$— |
| J212 | $Me_2N$— | C—H | Cl | $HO(CH_2)_2O$— |
| J213 | $Me_2N$— | C—H | Cl | 4-HO-pipe |
| J214 | $Me_2N$— | C—H | Cl | 4-$HOCH_2$-pipe |
| J215 | $Me_2N$— | C—H | Cl | 4-$HO(CH_2)_2$-pipe |
| J216 | $Me_2N$— | C—H | Cl | 4-MeO-pipe |
| J217 | $Me_2N$— | C—H | Cl | $MeO(CH_2)_3O$— |

TABLE 37-continued

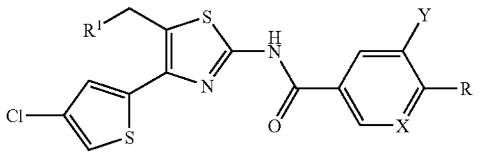

| No | $R^1$ | X | Y | R |
|---|---|---|---|---|
| J218 | $Me_2N$— | C—H | Cl | $MeO(CH_2)_2O$— |
| J219 | $Me_2N$— | C—H | Cl | $H_2O_3P$—$(CH_2)_3NH$— |
| J220 | $Me_2N$— | C—H | Cl | 4-$H_2O_3P$-pipe |
| J221 | $Me_2N$— | C—H | Cl | $(EtO)_2(O)P$—$(CH_2)_3NH$— |
| J222 | $Me_2N$— | C—H | Cl | 4-$(EtO)_2(O)P$-pipe |
| J223 | $Me_2N$— | C—H | Cl | 4-NC-pipe |
| J224 | $Me_2N$— | C—H | Cl | 3-oxo-pipa |

TABLE 38

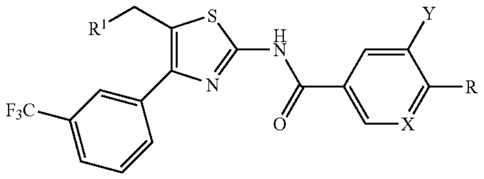

| No | $R^1$ | X | Y | R |
|---|---|---|---|---|
| K1 | nBuN(Me)— | C—H | Cl | 4-$H_2NOC$-pipe |
| K2 | nBuN(Me)— | C—F | F | 4-$H_2NOC$-pipe |
| K3 | cBuN(Me)— | C—H | Cl | 4-HO-pipe |
| K4 | cBuN(Me)— | C—H | Cl | 4-MeO-pipe |
| K5 | cBuN(Me)— | C—H | Cl | 4-$H_2O_3P$-pipe |
| K6 | cBuN(Me)— | C—H | Cl | 4-$(EtO)_2(O)P$-pipe |
| K7 | cBuN(Me)— | C—H | Cl | 4-NC-pipe |
| K8 | cBuN(Me)— | C—H | Cl | 4-$H_2NOC$-pipe |
| K9 | cBuN(Me)— | C—F | F | 4-HO-pipe |
| K10 | cBuN(Me)— | C—F | F | 4-MeO-pipe |
| K11 | cBuN(Me)— | C—F | F | 4-$H_2O_3P$-pipe |
| K12 | cBuN(Me)— | C—F | F | 4-$(EtO)_2(O)P$-pipe |
| K13 | cBuN(Me)— | C—F | F | 4-NC-pipe |
| K14 | cBuN(Me)— | C—F | F | 4-$H_2NOC$-pipe |
| K15 | iBuN(Me)— | C—H | Cl | 4-HO-pipe |
| K16 | iBuN(Me)— | C—H | Cl | 4-MeO-pipe |
| K17 | iBuN(Me)— | C—H | Cl | 4-$H_2O_3P$-pipe |
| K18 | iBuN(Me)— | C—H | Cl | 4-$(EtO)_2(O)P$-pipe |
| K19 | iBuN(Me)— | C—H | Cl | 4-NC-pipe |
| K20 | iBuN(Me)— | C—H | Cl | 4-$H_2NOC$-pipe |
| K21 | iBuN(Me)— | C—F | F | 4-HO-pipe |
| K22 | iBuN(Me)— | C—F | F | 4-MeO-pipe |
| K23 | iBuN(Me)— | C—F | F | 4-$H_2O_3P$-pipe |
| K24 | iBuN(Me)— | C—F | F | 4-$(EtO)_2(O)P$-pipe |
| K25 | iBuN(Me)— | C—F | F | 4-NC-pipe |
| K26 | iBuN(Me)— | C—F | F | 4-$H_2NOC$-pipe |
| K27 | pipe | C—H | Cl | 4-HO-pipe |
| K28 | pipe | C—H | Cl | 4-MeO-pipe |
| K29 | pipe | C—H | Cl | 4-$H_2O_3P$-pipe |
| K30 | pipe | C—H | Cl | 4-$(EtO)_2(O)P$-pipe |
| K31 | pipe | C—H | Cl | 4-NC-pipe |
| K32 | pipe | C—H | Cl | 4-$H_2NOC$-pipe |
| K33 | pipe | C—F | F | 4-HO-pipe |
| K34 | pipe | C—F | F | 4-MeO-pipe |
| K35 | pipe | C—F | F | 4-$H_2O_3P$-pipe |
| K36 | pipe | C—F | F | 4-$(EtO)_2(O)P$-pipe |
| K37 | pipe | C—F | F | 4-NC-pipe |
| K38 | pipe | C—F | F | 4-$H_2NOC$-pipe |
| K39 | 2-Me-pyrr | C—H | Cl | 4-HO-pipe |
| K40 | 2-Me-pyrr | C—H | Cl | 4-MeO-pipe |
| K41 | 2-Me-pyrr | C—H | Cl | 4-$H_2O_3P$-pipe |
| K42 | 2-Me-pyrr | C—H | Cl | 4-$(EtO)_2(O)P$-pipe |
| K43 | 2-Me-pyrr | C—H | Cl | 4-NC-pipe |
| K44 | 2-Me-pyrr | C—H | Cl | 4-$H_2NOC$-pipe |
| K45 | 2-Me-pyrr | C—F | F | 4-HO-pipe |

TABLE 38-continued

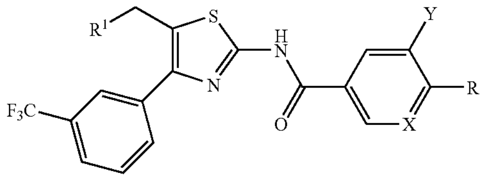

| No | $R^1$ | X | Y | R |
|---|---|---|---|---|
| K46 | 2-Me-pyrr | C—F | F | 4-MeO-pipe |
| K47 | 2-Me-pyrr | C—F | F | 4-$H_2O_3P$-pipe |
| K48 | 2-Me-pyrr | C—F | F | 4-$(EtO)_2(O)P$-pipe |
| K49 | 2-Me-pyrr | C—F | F | 4-NC-pipe |
| K50 | 2-Me-pyrr | C—F | F | 4-$H_2NOC$-pipe |
| K51 | 3-Me-pyrr | C—H | Cl | 4-HO-pipe |
| K52 | 3-Me-pyrr | C—H | Cl | 4-MeO-pipe |
| K53 | 3-Me-pyrr | C—H | Cl | 4-$H_2O_3P$-pipe |
| K54 | 3-Me-pyrr | C—H | Cl | 4-$(EtO)_2(O)P$-pipe |
| K55 | 3-Me-pyrr | C—H | Cl | 4-NC-pipe |
| K56 | 3-Me-pyrr | C—H | Cl | 4-$H_2NOC$-pipe |
| K57 | 3-Me-pyff | C—F | F | 4-HO-pipe |
| K58 | 3-Me-pyrr | C—F | F | 4-MeO-pipe |
| K59 | 3-Me-pyrr | C—F | F | 4-$H_2O_3P$-pipe |
| K60 | 3-Me-pyrr | C—F | F | 4-$(EtO)_2(O)P$-pipe |
| K61 | 3-Me-pyrr | C—F | F | 4-NC-pipe |
| K62 | 3-Me-pyrr | C—F | F | 4-$H_2NOC$-pipe |
| K63 | iPrN(Me)— | C—H | Cl | 4-HO-pipe |
| K64 | iPrN(Me)— | C—H | Cl | 4-MeO-pipe |
| K65 | iPrN(Me)— | C—H | Cl | 4-$H_2O_3P$-pipe |
| K66 | iPrN(Me)— | C—H | Cl | 4-$(EtO)_2(O)P$-pipe |
| K67 | iPrN(Me)— | C—H | Cl | 4-NC-pipe |
| K68 | iPrN(Me)— | C—H | Cl | 4-$H_2NOC$-pipe |
| K69 | iPrN(Me)— | C—F | F | 4-HO-pipe |
| K70 | iPrN(Me)— | C—F | F | 4-MeO-pipe |
| K71 | iPrN(Me)— | C—F | F | 4-$H_2O_3P$-pipe |
| K72 | iPrN(Me)— | C—F | F | 4-$(EtO)_2(O)P$-pipe |
| K73 | iPrN(Me)— | C—F | F | 4-NC-pipe |
| K74 | iPrN(Me)— | C—F | F | 4-$H_2NOC$-pipe |
| K75 | $Me_2N$— | C—H | Cl | 4-HO-pipe |
| K76 | $Me_2N$— | C—H | Cl | 4-MeO-pipe |
| K77 | $Me_2N$— | C—H | Cl | 4-$H_2O_3P$-pipe |
| K78 | $Me_2N$— | C—H | Cl | 4-$(EtO)_2(O)P$-pipe |
| K79 | $Me_2N$— | C—H | Cl | 4-NC-pipe |
| K80 | $Me_2N$— | C—H | Cl | 4-$H_2NOC$-pipe |
| K81 | $Me_2N$— | C—F | F | 4-HO-pipe |
| K82 | $Me_2N$— | C—F | F | 4-MeO-pipe |
| K83 | $Me_2N$— | C—F | F | 4-$H_2O_3P$-pipe |
| K84 | $Me_2N$— | C—F | F | 4-$(EtO)_2(O)P$-pipe |
| K85 | $Me_2N$— | C—F | F | 4-NC-pipe |
| K86 | $Me_2N$— | C—F | F | 4-$H_2NOC$-pipe |

TABLE 39

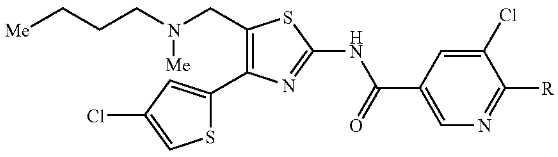

| No | R |
|---|---|
| L1 | 3-$HOCH_2$-pyrr |
| L2 | 3-$HO(CH_2)_2$-pyrr |
| L3 | 3-$HOCH_2$-azet |
| L4 | 3-$HO(CH_2)_2$-azet |
| L5 | 3-HO-azet |
| L6 | $MeO(CH_2)_3NH$— |
| L7 | $MeO(CH_2)_2NH$— |
| L8 | $MeO(CH_2)_3N(Me)$— |
| L9 | $MeO(CH_2)_2N(Me)$— |
| L10 | 3-MeO-pipe |
| L11 | 3-MeO-pyrr |

TABLE 39-continued

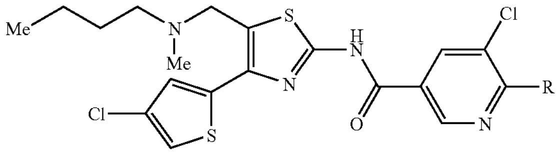

| No | R |
|---|---|
| L12 | 4-$MeOCH_2$-pipe |
| L13 | 4-$MeO(CH_2)_2$-pipe |
| L14 | 3-$MeOCH_2$-pyrr |
| L15 | 3-$MeO(CH_2)_2$-pyrr |
| L16 | 3-$MeOCH_2$-azet |
| L17 | 3-$MeO(CH_2)_2$-azet |
| L18 | NC-$(CH_2)_3$NH— |
| L19 | NC-$(CH_2)_2$NH— |
| L20 | NC-$(CH_2)_3$N(Me)— |
| L21 | NC-$(CH_2)_2$N(Me)— |
| L22 | NC-$(CH_2)_3$O— |
| L23 | NC-$(CH_2)_2$O— |
| L24 | 3-NC-pipe |
| L25 | 3-NC-pyrr |
| L26 | 4-NC-$CH_2$-pipe |
| L27 | 4-NC-$(CH_2)_2$-pipe |
| L28 | 3-$NCCH_2$-pyrr |
| L29 | 3-$H_2O_3P(CH_2)_2$-pyrr |
| L30 | 3-$H_2O_3P$ $CH_2$-azet |
| L31 | 3-$H_2O_3P(CH_2)_2$-azet |
| L32 | $(EtO)_2(O)P$—$(CH_2)_2$NH— |
| L33 | $(EtO)_2(O)P$—$(CH_2)_3$N(Me)— |
| L34 | $(EtO)_2(O)P$—$(CH_2)_2$N(Me)— |
| L35 | $(EtO)_2(O)P$—$(CH_2)_3$O— |
| L36 | $(EtO)_2(O)P$—$(CH_2)_2$O— |
| L37 | 3-$(EtO)_2(O)P$-pipe |
| L38 | 3-$(EtO)_2(O)P$-pyrr |
| L39 | 4-$(EtO)_2(O)P$-$CH_2$-pipe |
| L40 | 4-$(EtO)_2(O)P$-$(CH_2)_2$-pipe |
| L41 | 3-$(EtO)_2(O)P$-$CH_2$-pyrr |
| L42 | 3-$(EtO)_2(O)P$-$(CH_2)_2$-pyrr |
| L43 | 3-$(EtO)_2(O)P$-$CH_2$-azet |
| L44 | 3-$(EtO)_2(O)P$-$(CH_2)_2$-azet |
| L45 | HOCH(Me)$(CH_2)_2$NH— |
| L46 | HOCH(Me)$CH_2$NH— |
| L47 | $HOCH_2CH(OH)CH_2$NH— |
| L48 | HOCH(Me)$(CH_2)_2$N(Me)— |
| L49 | HOCH(Me)$CH_2$N(Me)— |
| L50 | $HOCH_2CH(OH)CH_2$N(Me)— |
| L5i | HOCH(Me)$(CH_2)_2$O— |
| L52 | HOCH(Me)$CH_2$O— |
| L53 | $HOCH_2CH(OH)CH_2$O— |
| L54 | Mor |
| L55 | $MsNH(CH_2)_3$—NH— |
| L56 | $MsNH(CH_2)_2$N(Me)— |
| L57 | 3-$NC(CH_2)_2$-pyrr |
| L58 | 3-$NCCH_2$-azet |
| L59 | 3-$NC(CH_2)_2$-azet |
| L60 | 4-Me-3-oxo-pipa |
| L61 | 5-oxo-1,4-diazepan-1-yl |
| L62 | Me2NOC-pipe |
| L63 | 3-F-pyrr |
| L64 | 4-F-pipe |
| L65 | 4-(tetrazol-5-yl)-pipe |
| L66 | 4-$H_2O_3P$—$(CH_2)_2$-pipe |
| L67 | 3-$H_2O_3P$—$CH_2$-pyrr |
| L68 | $H_2NO_2S$—$(CH_2)_2$—NH— |
| L69 | $H_2NO_2S$—$(CH_2)_3$—NH— |
| L70 | $H_2NO_2S$—$(CH_2)_2$—N(Me)— |
| L71 | $H_2NO_2S$—$(CH_2)_3$—N(Me)— |
| L72 | $HO_3S$—$(CH_2)_2$—NH— |
| L73 | $MsNH(CH_2)_3$—N(Me)— |
| L74 | $HO_3S$—$(CH_2)_3$—NH— |
| L75 | $HO_3S$—$(CH_2)_2$—N(Me)— |
| L76 | $HO_3S$—$(CH_2)_3$—N(Me)— |
| L77 | 3-THP-O— |
| L78 | 4-THP-O— |
| L79 | 2-THF-$CH_2$O— |

TABLE 39-continued

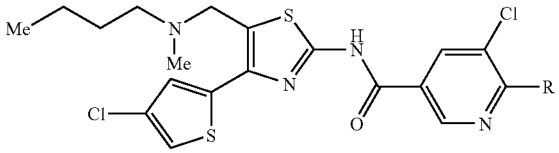

| No | R |
|---|---|
| L80 | 3-THF-$CH_2$O— |
| L81 | 3-THF-NH— |
| L82 | 4-THP-NH— |
| L83 | 2-THF-$CH_2$NH— |
| L84 | 3-THF-$CH_2$NH— |
| L85 | 3-THF-N(Me)— |
| L86 | 4-THP-N(Me)— |
| L87 | 2-THF-$CH_2$N(Me)— |
| L88 | 3-THF-$CH_2$N(Me)— |

TABLE 40

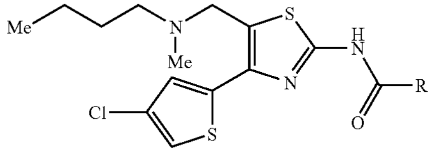

| No | R |
|---|---|
| M1 | quinolin-2-yl |
| M2 | quinolin-3-yl |
| M3 | quinolin-4-yl |
| M4 | quinolin-6-yl |
| M5 | quinolin-7-yl |
| M6 | 2-HO-quinolin-6-yl |
| M7 | 2-MeO-quinolin-6-yl |

TABLE 41

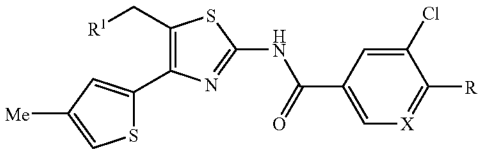

| No | $R^1$ | X | R |
|---|---|---|---|
| N1 | cBuN(Me)— | C—H | 4-HO-pipe |
| N2 | cBuN(Me)— | C—H | mor |
| N3 | cBuN(Me)— | C—H | 4-$H_2O_3P$-pipe |
| N4 | cBuN(Me)— | C—H | 4-NC-pipe |
| N5 | cBuN(Me)— | C—H | 3-oxo-pipa |
| N6 | cBuN(Me)— | N | 4-HO-pipe |
| N7 | cBuN(Me)— | N | mor |
| N8 | cBuN(Me)— | N | 4-$H_2O_3P$-pipe |
| N9 | cBuN(Me)— | N | 4-NC-pipe |
| N10 | cBuN(Me)— | N | 3-oxo-pipa |
| N11 | iBuN(Me)— | C—H | 4-HO-pipe |
| N12 | iBuN(Me)— | C—H | mor |
| N13 | iBuN(Me)— | C—H | 4-$H_2O_3P$-pipe |
| N14 | iBuN(Me)— | C—H | 4-NC-pipe |
| N15 | iBuN(Me)— | C—H | 3-oxo-pipa |
| N16 | iBuN(Me)— | N | 4-HO-pipe |
| N17 | iBuN(Me)— | N | mor |
| N18 | iBuN(Me)— | N | 4-$H_2O_3P$-pipe |
| N19 | iBuN(Me)— | N | 4-NC-pipe |
| N20 | iBuN(Me)— | N | 3-oxo-pipa |
| N21 | 2-Me-pyrr | C—H | 4-HO-pipe |
| N22 | 2-Me-pyrr | C—H | mor |

TABLE 41-continued

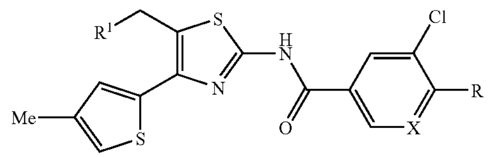

| No | $R^1$ | X | R |
|---|---|---|---|
| N23 | 2-Me-pyrr | C—H | 4-$H_2O_3P$-pipe |
| N24 | 2-Me-pyrr | C—H | 4-NC-pipe |
| N25 | 2-Me-pyrr | C—H | 3-oxo-pipa |
| N26 | 2-Me-pyrr | N | 4-HO-pipe |
| N27 | 2-Me-pyrr | N | mor |
| N28 | 2-Me-pyrr | N | 4-$H_2O_3P$-pipe |
| N29 | 2-Me-pyrr | N | 4-NC-pipe |
| N30 | 2-Me-pyrr | N | 3-oxo-pipa |
| N31 | iPrN(Me)— | C—H | 4-HO-pipe |
| N32 | iPrN(Me)— | C—H | mor |
| N33 | iPrN(Me)— | C—H | 4-$H_2O_3P$-pipe |
| N34 | iPrN(Me)— | C—H | 4-NC-pipe |
| N35 | iPrN(Me)— | C—H | 3-oxo-pipa |
| N36 | iPrN(Me)— | N | 4-HO-pipe |
| N37 | iPrN(Me)— | N | mor |
| N38 | iPrN(Me)— | N | 4-$H_2O_3P$-pipe |
| N39 | iPrN(Me)— | N | 4-NC-pipe |
| N40 | iPrN(Me)— | N | 3-oxo-pipa |

The invention claimed is:

1. A pharmaceutical composition comprising a 2-acylaminothiazole derivative represented by formula (I) or a pharmaceutically acceptable salt thereof as an active ingredient (I)

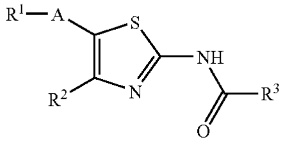

wherein

A is methylene;

$R^1$ is a group represented by the formula (II), or cyclic amino which may be substituted (II)

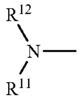

wherein $R^{11}$ is a hydrogen atom, a lower alkyl which may be substituted, or a cycloalkyl which may be substituted such that when A represents methylene, $R^{11}$ may be present as methylene which is bridged to thienyl or phenyl represented by $R^2$ or when A represents methylene, $R^{11}$ may be present as a lower alkylene which may be substituted and which forms a ring closed at the methylene represented by A; and $R^{12}$ is a lower alkyl, a cycloalkyl or a non-aromatic heterocycle, each of which may be substituted;

$R^2$ is thienyl or phenyl, each of which is substituted with one or more groups selected from the group consisting, of a lower alkyl which may be substituted with one or more halogens, and a halogen; and $R^3$ is an aromatic heterocycle, an aryl or cyclic amino, each of which may be substituted.

2. The pharmaceutical composition according to claim 1, which is a thrombocytopenia treating agent.

3. The pharmaceutical composition according to claim 1, which is a c-Mpl ligand.

4. A compound of formula (III) or a pharmaceutically acceptable salt thereof (III)

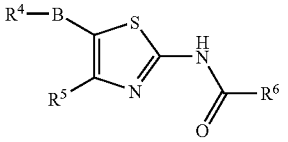

wherein

B is a lower alkylene;

$R^4$ is a group represented by the formula (II), or cyclic amino which may be substituted (II)

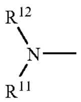

wherein $R^{11}$ is a hydrogen atom, a lower alkyl which may be substituted, or a cycloalkyl which may be substituted such that when B represents methylene, $R^{11}$ may be present as methylene which is bridged to thienyl or phenyl represented by $R^5$ or when B represents methylene, $R^{11}$ may be present as a lower alkylene which may be substituted and which forms a ring closed at the methylene represented by B; and $R^{12}$ is a lower alkyl, a cycloalkyl or a non-aromatic heterocycle, each of which may be substituted;

$R^5$ is thienyl or phenyl, each of which may be substituted; and $R^6$ is an aromatic heterocycle, an aryl or cyclic amino, each of which may be substituted provided that unsubstituted phenyl and indole which may be substituted are excluded.

5. The compound according to claim 4 or a pharmaceutically acceptable salt thereof, wherein B is methylene.

6. The compound according to claim 5 or a pharmaceutically acceptable salt thereof, wherein $R^5$ is thienyl or phenyl, each of which is substituted with one or more groups selected from the group consisting of a lower alkyl which may be substituted with one or more halogens, and a halogen.

7. The compound according to claim 6 or a pharmaceutically acceptable salt thereof, wherein $R^6$ is pyridyl which may be substituted, or phenyl which is substituted.

8. The compound according to claim 7 or a pharmaceutically acceptable salt thereof, wherein $R^6$ is pyridin-3-yl whose 5-position is substituted with a group selected from the group consisting of chloro and fluoro, and whose 6-position is substituted, or phenyl whose 3-position is substituted with a group selected from the group consisting of chloro and fluoro, whose 5-position is 5 substituted with a group selected from the member consisting of —H, chloro and fluoro, and whose 4-position is substituted.

9. The compound of claim 4, wherein the compound is

1-{3-chloro-5-[(4-(4-chlorothiophen-2-yl)-5-{[cyclobutyl(methyl)amino]methyl}thiazol-2-yl)carbamoyl]-2-pyridyl)piperidine-4-carboxylic acid, 1-(5-([5-{(butyl(methyl)amino]methyl}-4-(4-chlorothiophen-2-yl)thiazol-2-yl]carbamoyl}-3-chloro-2-pyridyl)piperidine-4-carboxylic acid, 1-{5-[(4-(4-chlorothiophen-2-yl)-5-{[(2R)-2-methylpyrrolidin-1-yl]methyl}thiazol-2yl)carbamoyl]-3-fluoro-2-pyridyl)piperidin-4-carboxylic acid, 1-{3-chloro-5-[(4-(4-chlorothiophen-2-yl)-5-{[(2S)-2-methylpyrrolidin-1yl]methyl}thiazol-2-yl)carbamoyl]-2-pyridyl}piperidine-4-carboxylic acid, 1-(3-chloro-5-{[4-(4-chlorothiophen-2-yl)-5-(dimethylaminomethyl)thiazol-2-yl]carbamoyl}-2-pyridyl)piperidine-4-carboxylic acid, 1-{3-chloro-5-[(4-(4-chlorothiophen-2-yl)-5-{[isopropyl (methyl)amino]methyl}thiazol-2-yl)carbamoyl]-2-pyridyl}piperidine-4-carboxylic acid, 4-[{3-chloro-5-[(4-(4-chlorothiophen-2-yl)-5-[isopropyl (methyl)amino]methyl}thiazol-2-yl)carbamoyl]-2-pyridyl}(methyl)amino]butyric acid, 1-{3-chloro-5-[(4-(4-chlorothiophen-2-yl)-5-{[(3S)-3-methylpyrrolidin-1-yl]methyl}thiazol-2-yl)carbamoyl]-2-pyridyl}piperidine-4-carboxylic acid, 1-{3-chloro-5-[(4-(4-chlorothiophen-2-yl)-5-{[[(2S)-2-methoxypropyl](methyl)amino]methyl}thiazol-2-yl) carbamoyl]-2-pyridyl)piperidine-4-carboxylic acid, N-[5-{[butyl(methyl)amino]methyl}-4-(4-chlorothiophen-2-yl)thiazol-2-yl]-5-chloro-6-[(3-hydroxypropyl)amino]nicotinamide, N-[5-{[butyl(methyl)amino]methyl}-4-(4-chlorothiophen-2-yl)thiazol-2-yl]-5-chloro-6-(3-oxopiperazin-1-yl)nicotinamide or N-[5-{[butyl(methyl)amino]methyl}-4-(4-chlorothiophen-2-yl)thiazol-2-yl]-5-chloro-6-[4-(hydroxymethyl)piperidino]nicotinamide, or a pharmaceutically acceptable salt thereof.

10. A pharmaceutical composition comprising the compound according to any one of claims 4 to 9 as an active ingredient.

11. The pharmaceutical composition according to claim 10, which is a platelet increasing agent.

12. The pharmaceutical composition according to claim 10, which is a thrombocytopenia treating agent.

13. The pharmaceutical composition according to claim 10, which is a c-Mpl ligand.

14. A method of increasing platelets in a patient comprising administering to the patient a pharmaceutical composition comprising a 2-acylaminothiazole derivative represented by formula (I) or a pharmaceutically acceptable salt thereof as an active ingredient (I)

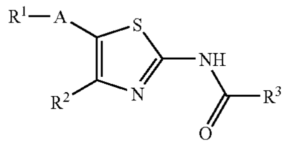

wherein

A: a lower alkylene;

$R^1$ is a group represented by the formula (II), or cyclic amino which may be substituted (II)

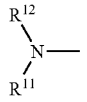

wherein $R^{11}$ is a hydrogen atom, a lower alkyl which may be substituted, or a cycloalkyl which may be substituted such that when A represents methylene, $R^{11}$ may be present as methylene which is bridged to thienyl or phenyl represented by $R^2$ or when A represents methylene, $R^{11}$ may be present as a lower alkylene which may be substituted and which forms a ring closed at the methylene represented by A; and $R^{12}$ is a lower alkyl, a cycloalkyl or a non-aromatic heterocycle, each of which may be substituted;

$R^2$ is thienyl or phenyl, each of which may be is substituted; and $R^3$ is an aromatic heterocycle, an aryl or cyclic amino, each of which may be substituted.

15. The method according to claim 14, wherein A is methylene.

16. The method according to claim 15, wherein $R^2$ is thienyl or phenyl, each of which is substituted with one or more groups selected from the group consisting, of a lower alkyl which may be substituted with one or more halogens, and a halogen.

17. The method according to claim 14, wherein the pharmaceutical composition is administered orally in a daily amount of 0.0001 mg/kg body weight to 50 mg/kg body weight, 0.001 mg/kg body weight to 10 mg/kg body weight, or 0.01 mg/kg body weight to 1 mg/kg body weight.

18. The method according to claim 17, wherein the daily amount is administered in one, two, three, or four doses.

19. The method according to claim 14, wherein the pharmaceutical composition is administered intravenously in a daily amount of 0.0001 mg/kg body weight to 1 mg/kg body weight or 0.0001 mg/kg body weight to 0.1 mg/kg body weight.

20. A method of treating thrombocytopenia in a patient comprising administering to the patient a pharmaceutical composition comprising a 2-acylaminothiazole derivative represented by formula (I) or a pharmaceutically acceptable salt thereof as an active ingredient (I)

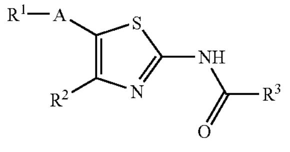

wherein

A: a lower alkylene;

$R^1$ is a group represented by the formula (II), or cyclic amino which may be substituted (II)

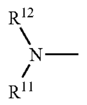

wherein $R^{11}$ is a hydrogen atom, a lower alkyl which may be substituted, or a cycloalkyl which may be substituted such that when A represents methylene, $R^{11}$ may be present as methylene which is bridged to thienyl or phenyl represented by $R^2$ or when A represents methylene, $R^{11}$ may be present as a lower alkylene which may be substituted and which forms a ring closed at the methylene represented by A; and $R^{12}$ is a lower alkyl, a cycloalkyl or a non-aromatic heterocycle, each of which may be substituted;

$R^2$ is thienyl or phenyl, each of which may be is substituted; and $R^3$ is an aromatic heterocycle, an aryl or cyclic amino, each of which may be substituted.

21. The method according to claim 20, wherein A is methylene.

22. The method according to claim 21, wherein $R^2$ is thienyl or phenyl, each of which is substituted with one or more groups selected from the group consisting, of a lower alkyl which may be substituted with one or more halogens, and a halogen.

23. The method according to claim 20, wherein the pharmaceutical composition is administered orally in a daily amount of 0.0001 mg/kg body weight to 50 mg/kg body weight, 0.001 mg/kg body weight to 10 mg/kg body weight, or 0.01 mg/kg body weight to 1 mg/kg body weight.

24. The method according to claim 23, wherein the daily amount is administered in one, two, three, or four doses.

25. The method according to claim 20, wherein the pharmaceutical composition is administered intravenously in a daily amount of 0.0001 mg/kg body weight to 1 mg/kg body weight or 0.0001 mg/kg body weight to 0.1 mg/kg body weight.

26. The method according to claim 20, wherein the thrombocytopenia is caused by one or more of anemia, myelodysplastic syndrome, chemotherapy, radiotherapy, idiopathic thrombocytopenic purpura, hepatic diseases, and human immunodeficiency virus (HIV).

27. A method of regulating c-Mpl activity for the treatment of thrombocytopenia comprising administering a c-Mpl ligand to a patient, wherein the c-Mpl ligand comprises a 2-acylaminothiazole derivative represented by formula (I) or a pharmaceutically acceptable salt thereof as an active ingredient (I)

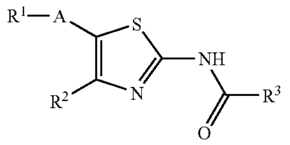

wherein

A: a lower alkylene;

$R^1$ is a group represented by the formula (II), or cyclic amino which may be substituted (II)

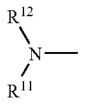

wherein $R^{11}$ is a hydrogen atom, a lower alkyl which may be substituted, or a cycloalkyl which may be substituted such that when A represents methylene, $R^{11}$ may be present as methylene which is bridged to thienyl or phenyl represented by $R^2$ or when A represents methylene, $R^{11}$ may be present as a lower alkylene which may be substituted and which forms a ring closed at the methylene represented by A; and $R^{12}$ is a lower alkyl, a cycloalkyl or a non-aromatic heterocycle, each of which may be substituted;

$R^2$ is thienyl or phenyl, each of which may be is substituted; and $R^3$ is an aromatic heterocycle, an aryl or cyclic amino, each of which may be substituted.

28. The method according to claim 27, wherein A is methylene.

29. The method according to claim 28, wherein $R^2$ is thienyl or phenyl, each of which is substituted with one or more groups selected from the group consisting, of a lower alkyl which may be substituted with one or more halogens, and a halogen.

30. The method according to claim 27, wherein the pharmaceutical composition is administered orally in a daily amount of 0.0001 mg/kg body weight to 50 mg/kg body weight, 0.001 mg/kg body weight to 10 mg/kg body weight, or 0.01 mg/kg body weight to 1 mg/kg body weight.

31. The method according to claim 30, wherein the daily amount is administered in one, two, three, or four doses.

32. The method according to claim 27, wherein the pharmaceutical composition is administered intravenously in a daily amount of 0.0001 mg/kg body weight to 1 mg/kg body weight or 0.0001 mg/kg body weight to 0.1 mg/kg body weight.

* * * * *